US008143411B2

(12) United States Patent
Bärfacker et al.

(10) Patent No.: US 8,143,411 B2
(45) Date of Patent: Mar. 27, 2012

(54) SUBSTITUTED 6-PHENYLNICOTINIC ACIDS AND THEIR USE

(75) Inventors: Lars Bärfacker, Oberhausen (DE); Barbara Albrecht-Küpper, Wülfrath (DE); Peter Kolkhof, Wuppertal (DE); Yolanda Cancho Grande, Leverkusen (DE); Adam Nitsche, Pulheim (DE); Heinrich Meier, Wuppertal (DE); Carsten Schmeck, Mülheim (DE); Jens Schamberger, Wuppertal (DE); Klemens Lustig, Wuppertal (DE)

(73) Assignee: Bayer Animal Health GmbH (DE)

( * ) Notice: Subject to any disclaimer, the term of this patent is extended or adjusted under 35 U.S.C. 154(b) by 0 days.

(21) Appl. No.: 12/676,568

(22) PCT Filed: Aug. 26, 2008

(86) PCT No.: PCT/EP2008/006969
§ 371 (c)(1),
(2), (4) Date: Apr. 22, 2010

(87) PCT Pub. No.: WO2009/033561
PCT Pub. Date: Mar. 19, 2009

(65) Prior Publication Data
US 2010/0234432 A1    Sep. 16, 2010

(30) Foreign Application Priority Data
Sep. 7, 2007 (DE) .......................... 10 2007 042 754

(51) Int. Cl.
*C07D 211/78* (2006.01)
*A61K 31/44* (2006.01)

(52) U.S. Cl. ........................................ 546/318; 514/356
(58) Field of Classification Search ........................ None
See application file for complete search history.

(56) References Cited

U.S. PATENT DOCUMENTS

| | | | |
|---|---|---|---|
| 3,655,679 A * | 4/1972 | Shen et al. ..................... | 546/298 |
| 5,217,982 A | 6/1993 | Fink et al. | |
| 5,889,002 A | 3/1999 | Nielsen et al. | |
| 6,225,310 B1 | 5/2001 | Nielsen et al. | |
| 6,380,218 B1 | 4/2002 | Marfat et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 6,995,263 B2 * | 2/2006 | Ackermann et al. .......... | 544/333 |
| 7,115,611 B2 | 10/2006 | Ackermann et al. | |
| 7,271,266 B2 | 9/2007 | Finke et al. | |
| 7,342,115 B2 | 3/2008 | Hutchison et al. | |
| 2004/0082798 A1 | 4/2004 | Alonso-Alija et al. | |
| 2004/0176446 A1 | 9/2004 | Alonso-Alija et al. | |
| 2005/0065144 A1 | 3/2005 | Feng et al. | |
| 2006/0052397 A1 | 3/2006 | Alonso-Alija et al. | |
| 2006/0063779 A1 | 3/2006 | Gunzner et al. | |
| 2006/0094769 A1 | 5/2006 | Alonso-Alija et al. | |
| 2008/0058314 A1 | 3/2008 | Alonso-Alija et al. | |
| 2008/0194598 A1 | 8/2008 | Woltering et al. | |
| 2009/0012126 A1 | 1/2009 | Lu et al. | |
| 2009/0062279 A1 | 3/2009 | Marsais et al. | |

FOREIGN PATENT DOCUMENTS

| | | |
|---|---|---|
| CA | 2662878 A1 | 3/2008 |
| CA | 2662879 A1 | 3/2008 |
| WO | 2006124874 A2 | 11/2006 |
| WO | WO 2008100715 A1 * | 8/2008 |

OTHER PUBLICATIONS

Vippagunta, S. et al., Adv. Drug Deliv Rev., vol. 48, 2001, pp. 3-26.*
Gadzhili, R. et al., Cehm Hetero Cpds., vol. 41, 2005, pp. 1009-1012.*
Patani, G. et al., Chem. Rev. 1996, vol. 96, pp. 3147-3176.*
Issemann I., et al., Activation of a Member of the Steroid Hormone Receptor Superfamily by Peroxisome Proliferators; Nature, (1980), pp. 645-650, vol. 347.
Hughes D.L., et al., The Mitsunobu Reaction, Organic Reactions; John-Wiley & Sons, Inc., (1992), pp. 335-338, vol. 42.
Hughes D.L., Progress in the Mitsunobu Reaction. A Review; Organic Preparations and Procedures Int., (1996), pp. 127-164, vol. 28, No. 2.
PCT International Search Report dated Dec. 10, 2008, 7 Pgs.
Ashton, M.J., et al., Synthesis of 6-Aryl-4-Hydroxypiperidin-2-Ones and a Possible Application to the Synthesis of a Novel HMG-COA Reductase Inhibitor; Heterocycles, (1989), pp. 1015-1035, vol. 28, No. 2.
Holz J., et al., Synthesis of a New Chiral Bisphospholane Ligand for the RH(I)-Catalyzed Enantioselective Hydrogenation of Isomeric β-Acylamido Acrylates; J. Org. Chem., (2003), pp. 1701-1707, vol. 68.
Pena D., et al., Highly Enantioselective Rhodium-Catalyzed Hydrogenation of β-Dehydroamino Acid Derivatives Using Monodentate Phos Phoramidites; J. Am. Chem. Soc., (2002), pp. 14552-14553, vol. 124.
Garber et al., A Sensitive and Convenient Method for Lipoprotein Profile Analysis of Individual Mouse Plasma Samples, Journal of Lipid Research, (2000), pp. 1020-1026, vol. 41.
Katsuyama et al., A Convenient and Regioselective Synthesis of 4-Trifluoromethylpuridines; Synthesis, (1997), pp. 1321-1324.
Tsuzuki et al., Synthesis and Structure—Activity Relationships of Novel 7-Substituted 1, 4-Dihydro-4-Oxo-1-(2-Thiazolyl)-1, 8-Naphthyridine-3-Carboxylic Acids as Antitumor Agents. Part 2; J. Med. Chem, (2004), pp. 2097-2109, vol. 47.
Makabe, O., et al., A Convenient Synthesis of 1, 4-Dihydro-4-Oxonicotinic Acid Derivatives, Heterocycles, (1979), pp. 239-246, vol. 13.
Clauss, A., Rapid Clotting Physiological Method for Determination of Fibrinogen, ACTA HAEMAT, (1957), pp. 234-246, vol. 17.
Makabe et al., A Convenient Synthesis of 1,4-Dihydro-4-Oxonicotinic Acid Derivatives: Heterocycles, (1979), pp. 239-246, vol. 13.
Tsuzuki T., et al., Synthesis and Structure—Activity Relationships of Novel 7-Substituted 1,4-Dihydro-4-Oxo-1-(2-Thiazolyl)-1,8-Naphthyridine-3-Carboxylic Acids as Antitumor Agents, Part 2, J. Med. Chem, (2004), pp. 2097-2109, vol. 47.
Katsuyama I., et al., A Convenient and Regioselective Synthesis of 4-Trifluoromethylpyridines; (1997), pp. 1321-1324, vol. 11.

* cited by examiner

*Primary Examiner* — Janet Andres
*Assistant Examiner* — Heidi Reese

(57) ABSTRACT

The present application relates to novel substituted 6-phenylnicotinic acid derivatives, to processes for their preparation, to their use for the treatment and/or prophylaxis of diseases and to their use for preparing medicaments for the treatment and/or prophylaxis of diseases, preferably for the treatment and/or prophylaxis of cardiovascular disorders, in particular dyslipidaemias, arteriosclerosis and heart failure.

7 Claims, No Drawings

SUBSTITUTED 6-PHENYLNICOTINIC ACIDS AND THEIR USE

The present invention relates to novel substituted 6-phenylnicotinic acid derivatives, to processes for their preparation, to their use for the treatment and/or prophylaxis of diseases and to their use for preparing medicaments for the treatment and/or prophylaxis of diseases, preferably for the treatment and/or prophylaxis of cardiovascular diseases, in particular dyslipidaemias, arteriosclerosis and heart failure.

In spite of many successful therapies, cardiovascular disorders remain a serious public health problem. Treatment with statins, which inhibit HMG-CoA reductase, very successfully lowers both LDL cholesterol (LDL-C) plasma concentrations and the mortality of patients at risk; however, convincing treatment strategies for the therapy of patients having an unfavourable HDL-C/LDL-C ratio and/or hypertriglyceridaemia are still not available to date.

Currently, in addition to niacin, fibrates are the only therapy option for patients of these risk groups. They lower elevated triglyceride levels by 20-50%, reduce LDL-C by 10-15%, change the LDL particle size of atherogenic LDL of low density to less atherogenic LDL of normal density and increase the HDL concentration by 10-15%.

Fibrates act as weak agonists of the peroxysome-proliferator-activated receptor (PPAR)-alpha (*Nature* 1990, 347, 645-50). PPAR-alpha is a nuclear receptor which regulates the expression of target genes by binding to DNA sequences in the promoter range of these genes [also referred to as PPAR response elements (PPRE)]. PPREs have been identified in a number of genes coding for proteins which regulate lipid metabolism. PPAR-alpha is highly expressed in the liver, and its activation leads inter alia to lower VLDL production/secretion and reduced apolipoprotein CIII (ApoCIII) synthesis. In contrast, the synthesis of apolipoprotein A1 (ApoA1) is increased.

A disadvantage of fibrates which have hitherto been approved is that their interaction with the receptor is only weak ($EC_{50}$ in the μM range), which in turn is responsible for the relatively small pharmacological effects described above.

WO 98/45268 claims nicotinamide derivatives having PDE 4D- and TNF-inhibitory activity for treating respiratory diseases and also allergic, inflammatory and rheumatoid disorders. U.S. Pat. No. 5,217,982 describes cyclopentyl-substituted pyridines for the treatment of hypertension. WO 2004/043925 discloses 2-arylpyridines with various substituents as C5a receptor ligands for treating inflammatory, immunological and cardiovascular disorders. WO 2005/030751 describes substituted pyridine derivatives as DPP-IV inhibitors for the treatment of diabetes. WO 2005/049573 and WO 2005/049606 describe substituted nicotinic esters as synthesis intermediates without biological action. The preparation of certain 2-methylpyridine derivatives is published in *Synthesis* 1997, 11: 1321-1324. The preparation of 1,4-dihydro-4-oxonicotinic acid derivatives is published in *Heterocycles* 1979, 13(1): 239-246. WO 2006/103120 discloses heterocyclic compounds and their use for treating Alzheimers disease. WO 2006/124874 describes inter alia substituted pyridines for the treatment of cancer. WO 2006/028958 claims 2-arylpyridines for the treatment of tumor disorders. WO 2006/097220 claims 4-phenoxy-2-phenylpyrimidinecarboxylic acids and WO 2008/031500 and WO 2008/031501 claim 4-phenoxy- and 2-phenoxynicotinic acids as PPAR-alpha modulators for the treatment of dyslipidemias and arteriosclerosis. WO 2008/016643 discloses substituted 2- and 4-aminopyridines for treating various disorders.

It was an object of the present invention to provide novel compounds which are suitable for use as PPAR-alpha modulators for the treatment and/or prophylaxis of in particular cardiovascular disorders and have an improved metabolic stability compared to compounds from the prior art.

The present invention provides compounds of the general formula (I)

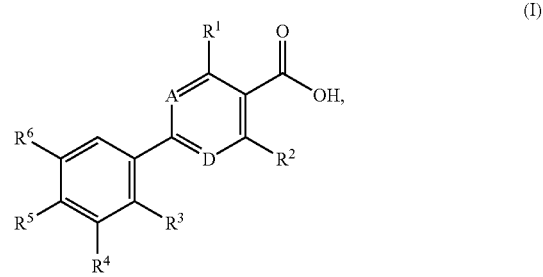

in which
one of the ring members A and D represents N and the other represents $CR^7$,
where
$R^7$ represents hydrogen, methyl or ethyl,
$R^1$ represents $(C_3-C_{10})$-alkyl, $(C_3-C_7)$-cycloalkyl, $—NR^A R^B$, $—OR^C$ or $—SR^D$,
where $(C_3-C_{10})$-alkyl may be substituted by one or two substituents independently of one another selected from the group consisting of fluorine, trifluoromethyl, hydroxyl, $(C_1-C_4)$-alkoxy, trifluoromethoxy and $(C_3-C_7)$-cycloalkyl,
where $(C_3-C_7)$-cycloalkyl may be substituted by one or two substituents independently of one another selected from the group consisting of fluorine, hydroxyl, oxo, trifluoromethyl, 2,2,2-trifluoroethyl, $(C_1-C_4)$-alkoxy and trifluoromethoxy,
and
where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
and
where
$R^A$ represents hydrogen or $(C_1-C_3)$-alkyl,
$R^B$ represents $(C_1-C_{10}$-alkyl or $(C_3-C_7)$-cycloalkyl,
where $(C_1-C_{10})$-alkyl may be substituted by a substituent selected from the group consisting of hydroxyl, $(C_1-C_4)$-alkoxy and $(C_3-C_7)$-cycloalkyl,
where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
and
where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
with the proviso that $R^B$ does not represent methyl if $R^A$ represents hydrogen, $R^C$ and $R^D$ represent $(C_2-C_{10})$-alkyl or $(C_3-C_7)$-cycloalkyl,
  where $(C_2-C_{10})$-alkyl may be substituted by a substituent selected from the group consisting of hydroxyl, $(C_1-C_4)$-alkoxy and $(C_3-C_7)$-cycloalkyl,
    where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
  and
  where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
or
$R^1$ represents methyl, ethyl, methoxy or methylthio,
  where methyl, ethyl, methoxy and methylthio are substituted by a substituent $(C_3-C_7)$-cycloalkyl,
    where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
and
where in all the cycloalkyl groups mentioned a $CH_{12}$ unit may be replaced by oxygen,
$R^2$ represents $(C_1-C_3)$-alkyl or cyclopropyl,
  where $(C_1-C_3)$-alkyl may be substituted by 1 to 3 fluorine substituents,
$R^3$ represents hydrogen or fluorine,
$R^4$ represents hydrogen, fluorine, chlorine or methyl,
$R^5$ represents hydrogen, halogen, nitro, cyano, trifluoromethyl, methyl, ethyl, trifluoromethoxy or methoxy,
$R^6$ represents hydrogen, fluorine, chlorine or methyl,
where at least one of the radicals $R^3$, $R^4$, $R^5$ and $R^6$ is different from hydrogen, and their salts, solvates and solvates of the salts.

Compounds according to the invention are the compounds of the formula (I) and their salts, solvates and solvates of the salts, the compounds, comprised by formula (I), of the formulae mentioned below and their salts, solvates and solvates of the salts and the compounds comprised by the formula (I), mentioned below as embodiments and their salts, solvates and solvates of the salts if the compounds, comprised by the formula (I), mentioned below are not already salts, solvates and solvates of the salts.

Depending on their structure, the compounds according to the invention can exist in stereoisomeric forms (enantiomers, diastereomers). Accordingly, the invention comprises the enantiomers or diastereomers and their respective mixtures. From such mixtures of enantiomers and/or diastereomers, it is possible to isolate the stereoisomerically uniform constituents in a known manner.

If the compounds according to the invention can be present in tautomeric forms, the present invention comprises all tautomeric forms.

In the context of the present invention, preferred salts are physiologically acceptable salts of the compounds according to the invention. The invention also comprises salts which for their part are not suitable for pharmaceutical applications, but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds according to the invention which, in solid or liquid state, form a complex by coordination with solvent molecules. Hydrates are a specific form of the solvates where the coordination is with water. In the context of the present invention, preferred solvates are hydrates.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In particular, the present invention also comprises hydrolyzable ester derivatives of the carboxylic acids of the formula (I). These are to be understood as being esters which can be hydrolyzed in physiological media and in particular in vivo by enzymatical or chemical means to give the free carboxylic acids. Such esters are preferably straight-chain or branched $(C_1-C_6)$-alkyl esters in which the alkyl group may be substituted by hydroxyl, $(C_1-C_4)$-alkoxy, amino, mono-$(C_1-C_4)$-alkylamino and/or di-$(C_1-C_4)$-alkylamino. Particular preference is given to the methyl or ethyl esters of the compounds of the formula (I).

In the context of the present invention, unless specified otherwise, the substituents have the following meanings:

In the context of the invention, alkyl represents a straight-chain or branched alkyl radical having the number of carbon atoms stated in each case. The following radicals may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 1,4-dimethylpentyl, 4,4-dimethylpentyl and 1,4,4-trimethylpentyl.

In the context of the invention, cycloalkyl represents a monocyclic saturated alkyl radical having 3 to 7 carbon atoms. The following radicals may be mentioned by way of example and by way of preference: cyclopropyl, cyclobutyl, cyclopentyl, cyclohexyl and cycloheptyl.

In the context of the invention, alkoxy represents a straight-chain or branched alkoxy radical having 1 to 4 carbon atoms. The following radicals may be mentioned by way of example and by way of preference: methoxy, ethoxy, n-propoxy, isopropoxy, 1-methylpropoxy, n-butoxy, isobutoxy and tert-butoxy.

In the context of the invention, halogen includes fluorine, chlorine, bromine and iodine. Preference is given to chlorine or fluorine.

In the context of the invention, monoalkylamino represents an amino group having a straight-chain or branched alkyl substituent having 1 to 6 carbon atoms. The following radicals may be mentioned by way of example and by way of preference: methylamino, ethylamino, n-propylamino, isopropylamino and tert-butylamino.

In the context of the invention, dialkylamino represents an amino group having two identical or different straight-chain or branched alkyl substituents having in each case 1 to 6 carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

If radicals in the compounds according to the invention are substituted, the radicals can, unless specified otherwise, be mono- or polysubstituted. In the context of the present invention, the meanings of all radicals which occur more than once are independent of one another. Substitution with one, two or three identical or different substituents is preferred. Very particular preference is given to substitution with one substituent.

In the context of the present invention, preference is given to compounds of the formula (I), in which
one of the ring members A and D represents N and the other represents $CR^7$,
where
$R^7$ represents hydrogen or methyl,
$R^1$ represents $(C_3-C_8)$-alkyl, cyclopropyl, $-NR^AR^B$ or $-OR^C$,
where $(C_3-C_8)$-alkyl may be substituted by one or two substituents selected from the group consisting of fluorine, trifluoromethyl, hydroxyl, methoxy, ethoxy and trifluoromethoxy,
and
where cyclopropyl may be substituted by a substituent selected from the group consisting of fluorine, methyl, ethyl, trifluoromethyl and methoxy,
where
$R^A$ represents hydrogen or $(C_1-C_3)$-alkyl,
$R^B$ represents $(C_1-C_8)$-alkyl, cyclopropyl, cyclopentyl or cyclohexyl,
where $(C_1-C_8)$-alkyl may be substituted by a substituent selected from the group consisting of methoxy, ethoxy, cyclopropyl, cyclopentyl and cyclohexyl,
where cyclopropyl, cyclopentyl and cyclohexyl may be substituted by a substituent selected from the group consisting of fluorine, methyl, ethyl, trifluoromethyl and methoxy,
and
where cyclopropyl, cyclopentyl and cyclohexyl may be substituted by a substituent selected from the group consisting of fluorine, methyl, ethyl, trifluoromethyl and methoxy,
with the proviso that $R^B$ does not represent methyl if $R^A$ represents hydrogen,
$R^C$ represents $(C_2-C_8)$-alkyl, cyclopropyl, cyclopentyl or cyclohexyl,
where $(C_2-C_8)$-alkyl may be substituted by a substituent selected from the group consisting of methoxy, ethoxy, cyclopropyl, cyclopentyl and cyclohexyl,
where cyclopropyl, cyclopentyl and cyclohexyl may be substituted by a substituent selected from the group consisting of fluorine, methyl, ethyl, trifluoromethyl and methoxy,
and
where cyclopropyl, cyclopentyl and cyclohexyl may be substituted by a substituent selected from the group consisting of fluorine, methyl, ethyl, trifluoromethyl and methoxy,
or
$R^1$ represents methyl, ethyl or methoxy,
where methyl, ethyl and methoxy are each substituted by cyclopropyl, cyclopentyl or cyclohexyl,
where cyclopropyl, cyclopentyl and cyclohexyl may be substituted by a substituent selected from the group consisting of fluorine, methyl, ethyl, trifluoromethyl and methoxy,
and
where in all the cyclopentyl and cyclohexyl groups mentioned a $CH_2$ unit may be replaced by oxygen,
$R^2$ represents ethyl, isopropyl or trifluoromethyl,
$R^3$ represents hydrogen,
$R^4$ represents hydrogen or fluorine,
$R^5$ represents hydrogen, fluorine, chlorine, trifluoromethyl or methyl,
$R^6$ represents hydrogen or fluorine,
where at least one of the radicals $R^4$, $R^5$ and $R^6$ is different from hydrogen, and their salts, solvates and solvates of the salts.

Particular preference is given to the compounds of the formula (I) in which
one of the ring members A and D represents N and the other represents CH,
$R^1$ represents n-propyl, isopropyl, n-butyl, isobutyl, 1-methylpropyl, $-NR^AR^B$ or $-OR^C$,
where
$R^A$ represents hydrogen, methyl or ethyl,
$R^B$ represents ethyl, n-propyl, isopropyl, n-butyl, isobutyl, 1-methylpropyl or cyclopropyl,
where cyclopropyl may be substituted by a substituent selected from the group consisting of fluorine, methyl and trifluoromethyl,
$R^C$ represents n-propyl, isopropyl, n-butyl, isobutyl, 1-methylpropyl, cyclopropyl, cyclopentyl or cyclohexyl,
where cyclopropyl, cyclopentyl and cyclohexyl may be substituted by a substituent selected from the group consisting of fluorine, methyl and trifluoromethyl,
or
$R^1$ represents methoxy or ethoxy,
where methoxy and ethoxy are each substituted by cyclopropyl, cyclopentyl or cyclohexyl,
where cyclopropyl, cyclopentyl and cyclohexyl may be substituted by a substituent selected from the group consisting of fluorine, methyl and trifluoromethyl,
$R^2$ represents ethyl or trifluoromethyl,
$R^3$ represents hydrogen,
$R^4$ represents hydrogen or fluorine,
$R^5$ represents hydrogen, chlorine or methyl,
$R^6$ represents hydrogen or fluorine,
where at least one of the radicals $R^4$, $R^5$ and $R^6$ is different from hydrogen, and their salts, solvates and solvates of the salts.

Particular preference is also given to the compounds of the formula (I) in which
one of the ring members A and D represents N and the other represents CH, R¹ represents n-propyl, isopropyl, n-butyl, isobutyl, 1-methylpropyl or —OR^C,
  where
    R^C represents n-propyl, isopropyl, n-butyl, isobutyl, 1-methylpropyl, cyclopropyl, cyclopentyl or cyclohexyl,
      where cyclopropyl, cyclopentyl and cyclohexyl may be substituted by a substituent selected from the group consisting of fluorine, methyl and trifluoromethyl,
or
R¹ represents methoxy or ethoxy,
  where methoxy and ethoxy are each substituted by cyclopropyl, cyclopentyl or cyclohexyl,
    where cyclopropyl, cyclopentyl and cyclohexyl may be substituted by a substituent selected from the group consisting of fluorine, methyl and trifluoromethyl,
R² represents ethyl or trifluoromethyl,
R³ represents hydrogen,
R⁴ represents hydrogen or fluorine,
R⁵ represents hydrogen, chlorine or methyl,
R⁶ represents hydrogen or fluorine,
where at least one of the radicals R⁴, R⁵ and R⁶ is different from hydrogen, and their salts, solvates and solvates of the salts.

In the context of the present invention, preference is also given to the compounds mentioned below
6-(3-fluoro-4-methylphenyl)-2-isobutyl-4-(trifluoromethyl)nicotinic acid
6-(3-fluoro-4-methylphenyl)-2-isobutyl-4-(trifluoromethyl)nicotinic acid sodium salt
2-ethyl-6-(3-fluoro-4-methylphenyl)-4-isobutylnicotinic acid
6-(4-methylphenyl)-4-isobutyl-2-(trifluoromethyl)nicotinic acid potassium salt
2-(isopropylamino)-6-(4-methylphenyl)-4-(trifluoromethyl)nicotinic acid
6-(4-chlorophenyl)-2-isobutyl-4-(trifluoromethyl)nicotinic acid
2-isobutyl-6-(4-methylphenyl)-4-(trifluoromethyl)nicotinic acid
2-ethoxy-6-(3-fluoro-4-methylphenyl)-4-(trifluoromethyl)nicotinic acid
6-(4-chlorophenyl)-2-ethyl-4-isobutyl-nicotinic acid
6-(4-chlorophenyl)-4-ethoxy-2-(1-methylethyl)nicotinic acid
6-(4-chlorophenyl)-2-isobutyl-4-(trifluoromethyl)nicotinic acid sodium salt
and their salts, solvates and solvates of the salts.

In the context of the present invention, preference is also given to the compounds of the formula (I) in which
R² represents trifluoromethyl.

In the context of the present invention, preference is also given to the compounds of the formula (I) in which
R² represents methyl or ethyl.

In the context of the present invention, preference is also given to the compounds of the formula (I) in which
R¹ represents n-propyl, isopropyl, n-butyl, isobutyl or 1-methylpropyl.

In the context of the present invention, preference is also given to the compounds of the formula (I) in which
R¹ represents $(C_3-C_8)$-alkyl or —OR^C,
  where $(C_3-C_8)$-alkyl may be substituted by one or two substituents selected from the group consisting of fluorine, trifluoromethyl, hydroxyl, methoxy, ethoxy and trifluoromethoxy,
  and
  where
    R^C represents $(C_2-C_8)$-alkyl, cyclopropyl, cyclopentyl or cyclohexyl,
      where $(C_2-C_8)$-alkyl may be substituted by a substituent selected from the group consisting of methoxy, ethoxy, cyclopropyl, cyclopentyl and cyclohexyl,
      and
    where cyclopropyl, cyclopentyl and cyclohexyl may be substituted by a substituent selected from the group consisting of fluorine, methyl, ethyl, trifluoromethyl and methoxy.

In the context of the present invention, preference is also given to the compounds of the formula (I) in which
R¹ represents methyl, ethyl or methoxy,
  where methyl, ethyl and methoxy are each substituted by cyclopropyl, cyclopentyl or cyclohexyl,
    where cyclopropyl, cyclopentyl and cyclohexyl may be substituted by a substituent selected from the group consisting of fluorine, methyl, ethyl, trifluoromethyl and methoxy.

The individual radical definitions given in the respective combinations or preferred combinations of radicals may, independently of the particular given combination of radicals, also be replaced by radical definitions of other combinations.

Very particular preference is given to combinations of two or more of the preferred ranges mentioned above.

The invention furthermore provides a process for preparing the compounds of the formula (I) according to the invention, characterized in that a compound of the formula (II)

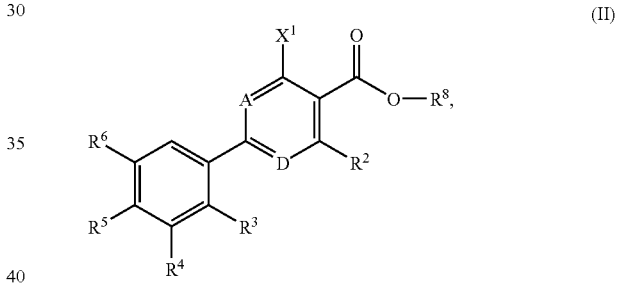

in which A, D, R², R³, R⁴, R⁵ and R⁶ each have the meanings given above,
X¹ represents a suitable leaving group, such as, for example, halogen, in particular chlorine,
and
R⁸ represents $(C_1-C_4)$-alkyl,
is either
[A] reacted in an inert solvent in the presence of a base and a suitable palladium catalyst with a compound of the formula (III-A)

$$R^{14}\text{—}X^2 \qquad (\text{III-A}),$$

in which
R¹⁴ represents methyl, ethyl, $(C_3-C_{10})$-alkyl or $(C_3-C_7)$-cycloalkyl,
  where methyl and ethyl are substituted by $(C_3-C_7)$-cycloalkyl,
  where $(C_3-C_{10})$-alkyl may be substituted by one or two substituents independently of one another selected from the group consisting of fluorine, trifluoromethyl, hydroxyl, $(C_1-C_4)$-alkoxy, trifluoromethoxy and $(C_3-C_7)$-cycloalkyl,
  where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
and
where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
and
where in all the cycloalkyl groups mentioned a $CH_2$ unit may be replaced by oxygen,
and
$X^2$ represents a croup of the formula —B(OR$^9$)$_2$ or —Zn-Hal,
where
Hal represents halogen, in particular chlorine, bromine or iodine,
and
$R^9$ represents hydrogen or $(C_1-C_4)$-alkyl
or
both radicals $R^9$ together form a —C(CH$_3$)$_2$—C(CH$_3$)$_2$ bridge,
to give compounds of the formula (IV-A)

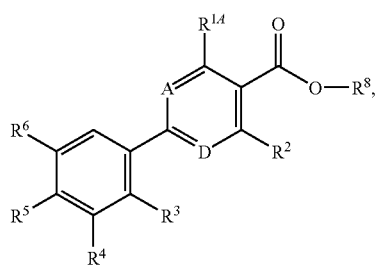

(IV-A)

in which A, D, R$^{1A}$, R$^2$, R$^3$, R$^4$, R$^5$, R$^6$ and R$^8$ each have the meanings given above,
and these are converted by basic or acidic hydrolysis into the carboxylic acids of the formula (I-A)

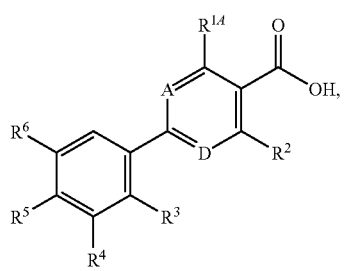

(I-A)

in which A, D, R$^{1A}$, R$^2$, R$^3$, R$^4$, R$^5$ and R$^6$ each have the meanings given above,
and the compounds of the formula (I-A) are, if appropriate, converted with the appropriate (i) solvents and/or (ii) bases or acids into their solvates, salts and/or solvates of the salts,
or
[B] reacted in an inert solvent in the presence of a base with a compound of the formula (III-B)

R$^{1B}$—H    (III-B), in which
R$^{1B}$ represents methoxy, methylthio, —NR$^A$R$^B$, —OR$^C$ or —SR$^D$,
where methoxy and methylthio are substituted by a substituent $(C_3-C_7)$-cycloalkyl,
where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy,
and
where in all the cycloalkyl groups mentioned a $CH_2$ unit may be replaced by oxygen,
and
where R$^A$, R$^B$, R$^C$ and R$^D$ have the meanings given above,
to give compounds of the formula (IV-B)

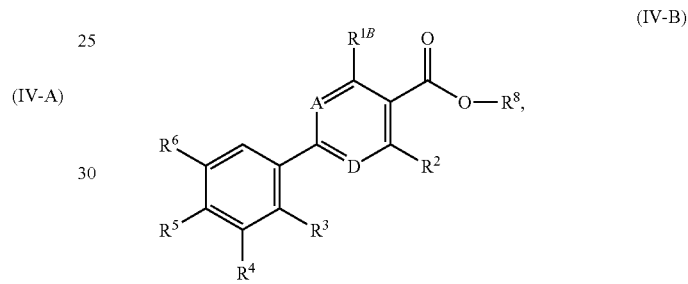

(IV-B)

in which A, D, R$^{1B}$, R$^2$, R$^3$, R$^4$, R$^5$, R$^6$ and R$^8$ each have the meanings given above,
and these are converted by basic or acidic hydrolysis into the carboxylic acids of the formula (I-B)

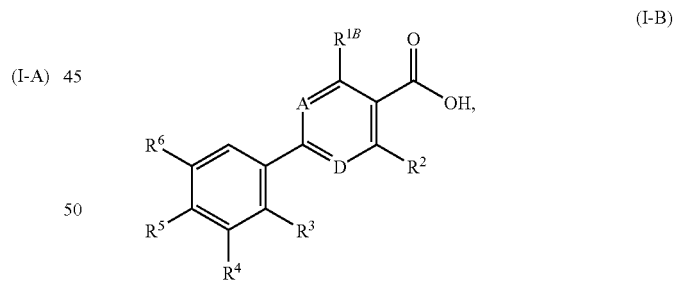

(I-B)

in which A, D, R$^{1B}$, R$^2$, R$^3$, R$^4$, R$^5$ and R$^6$ each have the meanings given above,
and the compounds of the formula (I-B) are, if appropriate, converted with the appropriate (i) solvents and/or (ii) bases or acids into their solvates, salts and/or solvates of the salts.

The compounds of the formulae (III-A) and (III-B) are commercially available, known from the literature or can be prepared analogously to processes known from the literature.

The compounds of the formula (II) in which A represents N and D represents CR$^7$ can be prepared by coupling compounds of the formula (V)

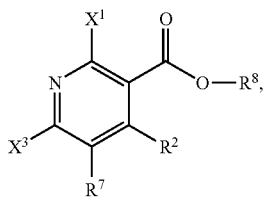
(V)

in which $R^2$, $R^7$, $R^8$ and $X^1$ have the meanings given above and
$X^3$ represents a suitable leaving group, such as, for example, halogen, in particular chlorine,
in an inert solvent in the presence of a suitable transition metal catalyst and, if appropriate, a base with a compound of the formula (VI)

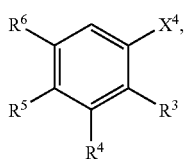
(VI)

in which $R^3$, $R^4$, $R^5$ and $R^6$ each have the meanings given above and
$X^4$ represents the group —B(OR$^9$)$_2$, —ZnHal or —MgHal, where Hal and $R^9$ have the meanings given above.

The compounds of the formulae (V) and (VI) are commercially available, known from the literature or can be prepared analogously to processes known from the literature.

The compounds of the formula (II) in which A represents CH and D represents N can be prepared by reacting compounds of the formula (VII)

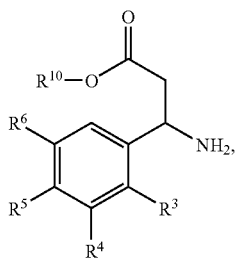
(VII)

in which $R^3$, $R^4$, $R^5$ and $R^6$ each have the meanings given above,
and
$R^{10}$ represents (C$_1$-C$_4$)-alkyl or benzyl,
initially in an inert solvent in the presence of an acid with a compound of the formula (VIII)

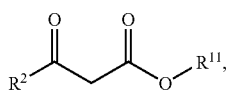
(VIII)

in which $R^2$ has the meaning given above,
and
$R^{11}$ represents (C$_1$-C$_4$)-alkyl or benzyl, to give a compound of the formula (IX)

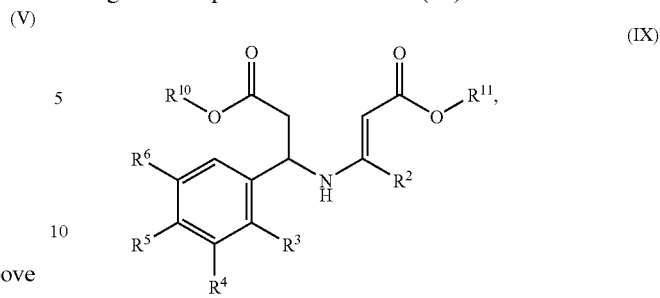
(IX)

in which $R^2$, $R^3$, $R^4$, $R^5$, $R^6$, $R^{10}$ and $R^{11}$ each have the meanings given above,
then cyclising this in an inert solvent in the presence of a base to give a compound of the formula (X)

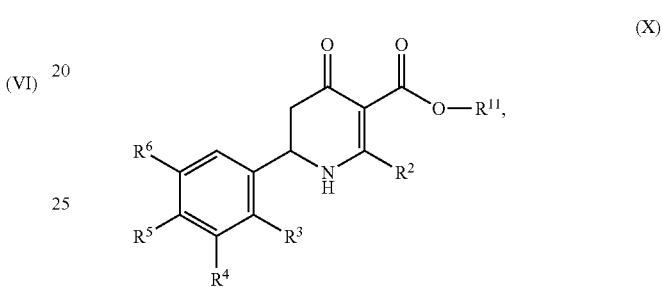
(X)

in which $R^2$, $R^3$, $R^4$, $R^5$, $R^6$ and $R^{11}$ each have the meanings given above,
and oxidizing this in an inert solvent with the aid of a suitable oxidizing agent, such as, for example, 2,3-dichloro-5,6-dicyano-1,4-benzoquinone, to give a compound of the formula (XI)

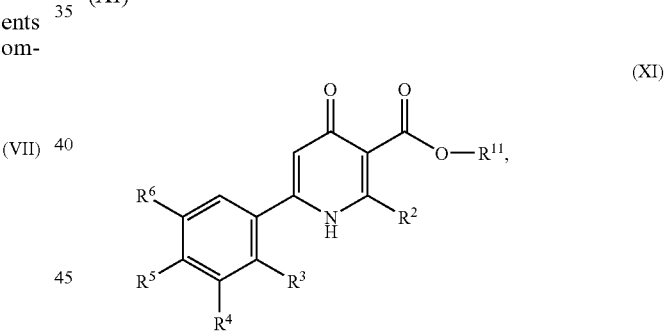
(XI)

in which $R^2$, $R^3$, $R^4$, $R^5$, $R^6$ and $R^{11}$ each have the meanings given above,
and then converting this with the aid of a suitable halogenating agent, such as, for example, phosphorus oxychloride, into a compound of the formula (II-A)

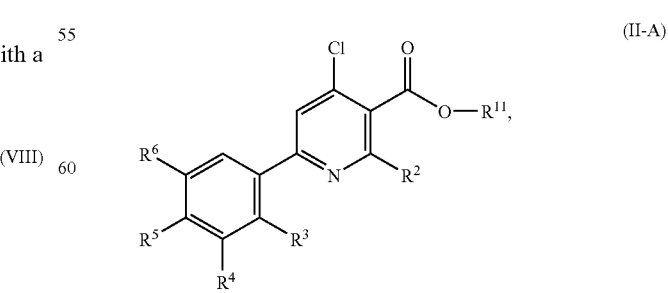
(II-A)

in which $R^2$, $R^3$, $R^4$, $R^5$, $R^6$ and $R^{11}$ each have the meanings given above.

The compounds of the formulae (VII) and (VIII) are commercially available, known from the literature or can be prepared analogously to processes known from the literature.

The compounds of the formula (II), in which A represents $CR^{7A}$ and D represents N, where $R^{7A}$ represents methyl or ethyl, can be prepared by converting compounds of the formula (X) in which the nitrogen atom is present in protected form in the presence of a base with a compound of the formula (XII)

in which $R^{7"}$ has the meaning given above, and $X^5$ represents a suitable leaving group, such as, for example, halogen, in particular bromine or iodine, into a compound of the formula (XIII)

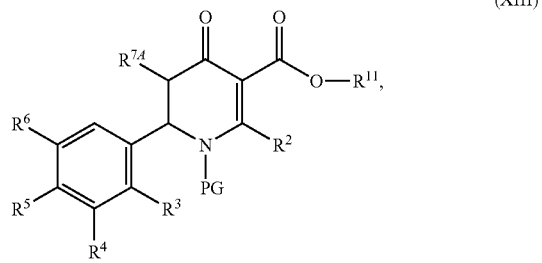

in which $R^2$, $R^3$, $R^4$, $R^5$, $R^6$, $R^{7A}$ and $R^{11}$ each have the meanings given above, and PG represents a temporary protective group, in particular p-methoxybenzyl, and reacting the compound of the formula (XIII) after removal of the protective group further according to standard methods analogously to process (X)→(XI)→(II-A).

The invention furthermore provides a process for preparing the compounds of the formula (I) according to the invention in which A represents CH and D represents N, characterized in that a compound of the formula (XI) is reacted in an inert solvent under Mitsunobu conditions with a compound of the formula (III-C)

in which $R^{1C}$ represents methoxy or $—OR^C$, where methoxy is substituted by a substituent $(C_3-C_7)$-cycloalkyl, where $(C_3-C_7)$-cycloalkyl may be substituted by one or two substituents independently of one another selected from the group consisting of fluorine, hydroxyl, oxo, $(C_1-C_4)$-alkyl, trifluoromethyl, 2,2,2-trifluoroethyl, $(C_1-C_4)$-alkoxy and trifluoromethoxy, and where in the cycloalkyl groups mentioned a $CH_2$ unit may be replaced by oxygen, and where $R^C$ has the meaning given above, to give compounds of the formula (IV-C)

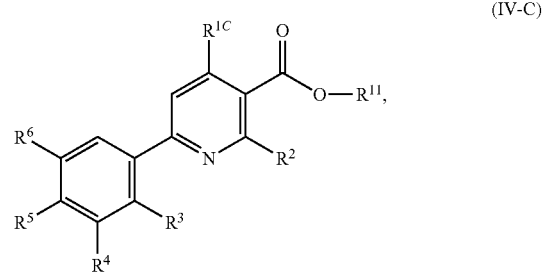

in which $R^{1C}$, $R^2$, $R^3$, $R^4$, $R^5$, $R^6$ and $R^{11}$ each have the meanings given above, and these are converted by basic or acidic hydrolysis into the carboxylic acids of the formula (I-C)

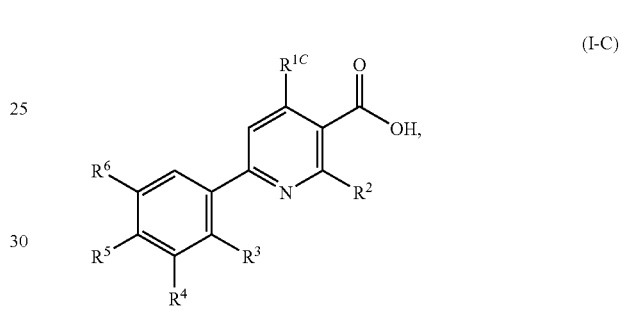

in which $R^{1C}$, $R^2$, $R^3$, $R^4$, $R^5$ and $R^6$ each have the meanings given above, and the compounds of the formula (I-C) are, if appropriate, converted with the appropriate (i) solvents and/or (ii) bases or acids into their solvates, salts and/or solvates of the salts.

The compounds of the formulae (III-C) are commercially available, known from the literature or can be prepared analogously to processes known from the literature.

The invention furthermore provides a process for preparing the compounds of the formula (I) according to the invention in which A represents $CR^7$ and D represents N, characterized in that a compound of the formula (XIV)

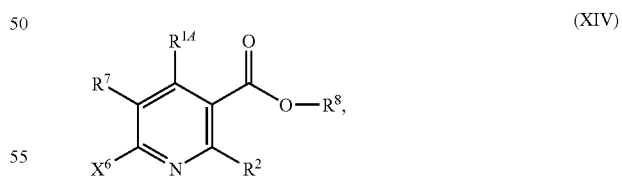

in which $R^{1A}$, $R^2$, $R^7$ and $R^8$ each have the meanings given above, and $X^6$ represents a suitable leaving group, such as, for example, halogen, in particular chlorine, is, in an inert solvent in the presence of a suitable transition metal catalyst and, if appropriate, a base, coupled with a compound of the formula (VI) to give compounds of the formula (IV-D)

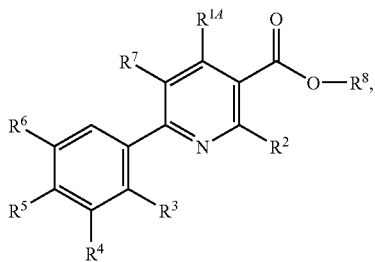

(IV-D)

in which $R^{14}$, $R^2$, $R^3$, $R^4$, $R^5$, $R^6$, $R^7$ and $R^8$ each have the meanings given above, and these are converted by basic or acidic hydrolysis into the carboxylic acids of the formula (I-D)

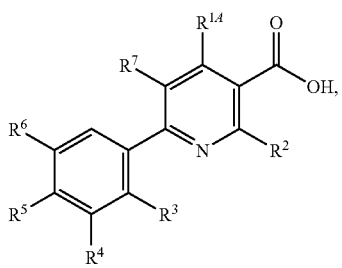

(I-D)

in which $R^{14}$, $R^2$, $R^3$, $R^4$, $R^5$, $R^6$ and $R^7$ each have the meanings given above, and the compounds of the formula (I-D) are, if appropriate, converted with the appropriate (i) solvents and/or (ii) bases or acids into their solvates, salts and/or solvates of the salts.

The compounds of the formula (XIV) can be prepared by reacting compounds of the formula (XV)

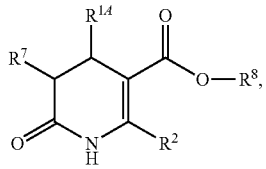

(XV)

in which $R^{14}$, $R^2$, $R^7$ and $R^8$ have the meanings given above, in an inert solvent with a suitable oxidizing agent, such as, for example, 2,3-dichloro-5,6-dicyano-1,4-benzoquinone, and a suitable halogenating agent, such as, for example, phosphorus oxychloride.

The compounds of the formula (XV) are commercially available, known from the literature or can be prepared analogously to processes known from the literature.

Compounds of the formula (XI) can also be prepared analogously to Makabe et al., *Heterocycles* 1979, 13(1), 239-246, as shown the synthesis scheme below:

Scheme 1

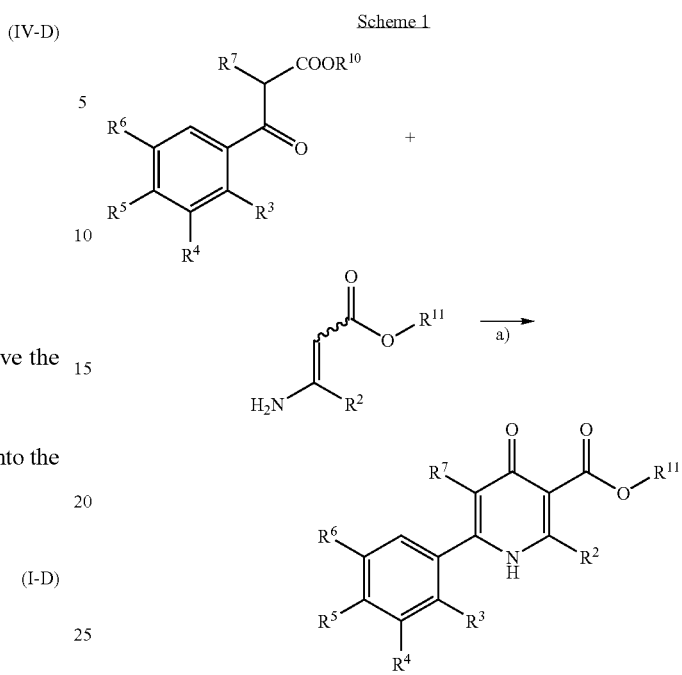

[a) xylene, 4 Å molecular sieve, reflux temperature]

Compounds of the formula (I), in which A represents N and D represents $CR^7$ can also be prepared analogously to Katsuyama et al., *Synthesis*, 239-246, 1997, as shown the synthesis scheme below:

Scheme 2

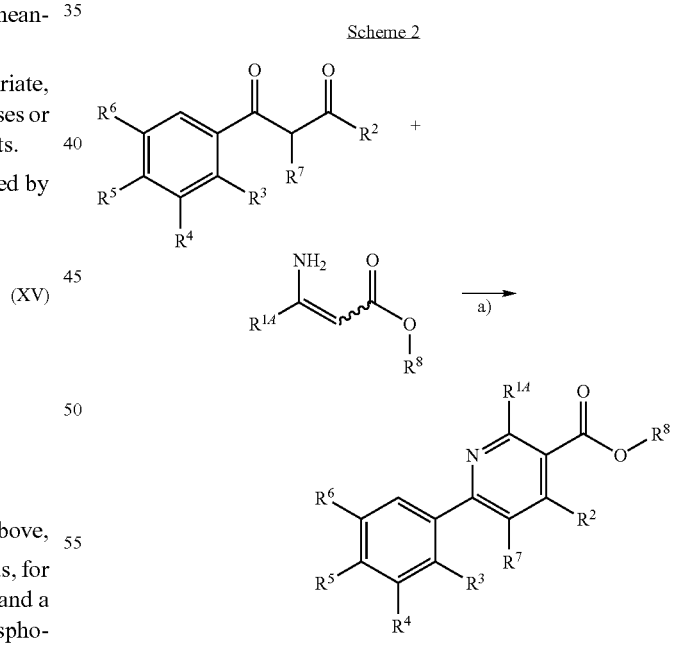

[a) acetonitrile or ethanol, reflux temperature]

Transition metal catalysts, catalyst ligands and auxiliary bases for the coupling reactions (II)+(III-A)→(IV-A), (V)+(VI)→(II) and (XIV)+(VI)→(IV-D) are known from the literature [cf., for example, J. Hassan et al., *Chem. Rev.* 102, 1359-1469 (2002)] and commercially available. Preference is given to using palladium or nickel catalysts.

In the case of the boronic acid couplings (II)+(III-A) [$X^2$=—B(OR$^9$)$_2$]→(IV-A), (V)+(VI)[$X^4$=—B(OR$^9$)$_2$]→(II) and (XIV)+(VI)[$X^4$=—B(OR$^4$)$_2$]→(IV-D) the reaction is carried out in the presence of an auxiliary base and, if appropriate, an additional catalyst ligand. Preference is given here to using bis(triphenylphosphine)palladium(II) chloride as catalyst, tris-(o-tolyl)phosphine as further ligand and aqueous potassium carbonate solution as auxiliary base. In the case of organozinc compounds [$X^2$=—ZnHal in (III-A) and $X^4$=—ZnHal in (VI)], the catalyst used is preferably tetrakis (triphenylphosphine)palladium(0).

Inert solvents for the boronic acid couplings (II)+(III-A) [$X^2$=—B(OR$^9$)$_2$]→(IV-A), (V)+(VI)[$X^4$=—B(OR$^9$)$_2$]→(II) and (XIV)+(VI)[$X^4$=—B(OR$^9$)$_2$](IV-D) are, for example, alcohols, such as methanol, ethanol, n-propanol, isopropanol, n-butanol or tert-butanol, ethers, such as diethyl ether, dioxane, tetrahydrofuran, glycol dimethyl ether or diethylene glycol dimethyl ether, hydrocarbons, such as benzene, toluene, xylene, hexane, cyclohexane or mineral oil fractions, or other solvents, such as dimethylformamide, dimethyl sulfoxide, N,N'-dimethylpropyleneurea (DMPU), N-methylpyrrolidone (NMP), pyridine, acetonitrile or else water. It is also possible to use mixtures of the solvents mentioned. Preference is given to using dimethylformamide or dioxane.

The coupling reactions (II)+(III-A)[$X^2$=—B(OR$^9$)$_2$]→(IV-A), (V)+(VI)[$X^4$=—B(OR$^9$)$_2$]→(II) and (XIV)+(VI) [$X^4$=—B(OR$^9$)$_2$]→(IV-D) are generally carried out in a temperature range of from −20° C. to +150° C., preferably at from 0° C. to +80° C., if appropriate in a microwave oven. The reactions can be carried out at atmospheric, elevated or reduced pressure (for example from 0.5 to 5 bar).

Inert solvents for the process step (II)+(III-B)→(IV-B) are, for example, ethers, such as diethyl ether, dioxane, tetrahydrofuran, glycol dimethyl ether or diethylene glycol dimethyl ether, hydrocarbons, such as benzene, toluene, xylene, hexane, cyclohexane or mineral oil fractionen, or other solvents, such as dimethylformamide, dimethyl sulfoxide, N,N'-dimethylpropyleneurea (DMPU), N-methylpyrrolidinone (NMP), pyridine, acetone, 2-butanone or acetonitrile. It is also possible to use mixtures of the solvents mentioned. Preference is given to using dimethylformamide or tetrahydrofuran.

Suitable bases for the process step (II)+(III-B)→(IV-B) are customary inorganic bases. These include in particular alkali metal hydroxides, such as, for example, lithium hydroxide, sodium hydroxide or potassium hydroxide, alkali metal or alkaline earth metal carbonates, such as lithium carbonate, sodium carbonate, potassium carbonate, calcium carbonate or cesium carbonate, alkali metal hydrides, such as sodium hydride or potassium hydride, or organometallic bases, such as n-butyllithium. Preference is given to sodium hydride and n-butyllithium. If $R^{1B}$=—NR$^A$R$^B$, it is also possible to use tert. organic amines as bases, in particular triethylamine. Here, the base is employed in an amount of from 1 to 5 mol, preferably in an amount of from 1.2 to 3 mol, based on 1 mol of the compound of the formula (III-B).

The reaction (II)+(Ill-B)→(IV-B) is generally carried out in a temperature range of from 0° C. to +150° C., preferably at from +20° C. to +120° C. The reaction can be carried out at atmospheric, elevated or reduced pressure (for example from 0.5 to 5 bar). In general, the reaction is carried out at atmospheric pressure.

The Mitsunobu reaction (XI)+(III-C)→(IV-C) [see: a) Hughes, D. L. "The Mitsunobu Reaction," *Organic Reactions*; John Wiley & Sons, Ltd, 1992, vol. 42, p. 335. b) Hughes, D. L. *Org. Prep. Proceed. Int.* 1996, 28, 127] is carried out using triphenylphosphine, or tri-n-butylphosphine, 1,2-bis(diphenylphosphino)ethane (DPPE), diphenyl (2-pyridyl)phosphine (Ph2P-Py), (p-dimethylaminophenyl) diphenylphosphine (DAP-DP), tris(4-dimethylaminophenyl)-phosphine (tris-DAP) and a suitable dialkyl azodicarboxylate, such as, for example, diethyl azodicarboxylate (DEAD), diisopropyl azodicarboxylate (DIAD), di-tert-butyl azodicarboxylate, N,N,N'N'-tetramethylazodicarboxamide (TMAD), 1,1'-(azodicarbonyl)dipiperidine (ADDP) or 4,7-dimethyl-3,5,7-hexahydro-1,2,4,7-tetrazocine-3,8-dione (DHTD). Preference is given to using triphenylphosphine and diisopropyl azodicarboxylate (DIAD).

Inert solvents for the Mitsunobu reaction (XI)+(III-C)→(IV-C) are, for example, ethers, such as tetrahydrofuran, diethyl ether, hydrocarbons, such as benzene, toluene, xylene, halogenated hydrocarbons, such as dichloromethane, dichloroethane or other solvents, such as acetonitrile. It is also possible to use mixtures of the solvents mentioned. Preference is given to using THF.

The Mitsunobu reaction (XI)+(Ill-C)→(IV-C) is generally carried out in a temperature range of from −78° C. to +180° C., preferably at from 0° C. to +50° C., if appropriate in a microwave oven. The reactions can be carried out at atmospheric, elevated or reduced pressure (for example from 0.5 to 5 bar).

The alkylation (X)+(XII)→(XIII) is generally carried out in a temperature range of from −78° C. to +50° C., preferably at from −78° C. to +20° C. The reactions can be carried out at atmospheric, elevated or reduced pressure (for example from 0.5 to 5 bar). In general, the reaction is carried out at atmospheric pressure.

Suitable bases for the alkylation (X)+(XII)→(XIII) are customary organic and inorganic bases. These include in particular alkali metal hydrides, such as sodium hydride or potassium hydride, and amides, such as sodium amide, lithium bis-(trimethylsilyl)amide, lithium diisopropylamide, or organometallic compounds, such as n-butyllithium or phenyllithium. Preference is given to lithium diisopropylamide and Lithium bis(trimethylsilyl)amide.

Inert solvents for the alkylation (X)+(XII)→(XIII) are, for example, ethers, such as tetrahydrofuran, diethyl ether, hydrocarbons, such as benzene, toluene, xylene, halogenated hydrocarbons, such as dichloromethane, dichloroethane, or other solvents, such as acetonitrile. It is also possible to use mixtures of the solvents mentioned. Preference is given to using THF.

The hydrolysis of the carboxylic esters in the process steps (IV-A)→(I-A), (IV-B)→(I-B), (IV-C)→(I-C) and (IV-D)→(I-D) is carried out by customary methods, if appropriate in a microwave oven, by treating the esters in inert solvents with acids or bases, where the salts initially formed are converted by subsequent treatment with acid into the free carboxylic acids. In the case of the tert-butyl esters, ester cleavage is preferably carried out using acids.

Suitable inert solvents for the hydrolysis of the carboxylic acids are water or the organic solvents customary for ester cleavage. These preferably include alcohols, such as methanol, ethanol, n-propanol, isopropanol, n-butanol or tert-butanol, or ethers, such as diethyl ether, tetrahydrofuran, dioxane or glycol dimethyl ether, or other solvents, such as acetone, acetonitrile, dichloromethane, dimethyl formamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol. In the case of reaction with trifluoroacetic acid, preference is given to using dichloromethane, and in the case of the reaction with hydrogen chloride, preference is given to using tetrahydrofuran, diethyl ether, dioxane or water.

Suitable bases for the ester hydrolysis are the customary inorganic bases. These preferably include alkali metal or alkaline earth metal hydroxides, such as, for example, sodium hydroxide, lithium hydroxide, potassium hydroxide or barium hydroxide, or alkali metal or alkaline earth metal carbonates, such as sodium carbonate, potassium carbonate or calcium carbonate. Particular preference is given to using sodium hydroxide or lithium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, if appropriate with addition of water. Preference is given to hydrogen chloride or trifluoroacetic acid in the case of the tort-butyl esters and to hydrochloric acid in the case of the methyl esters.

In the case of the benzyl esters, the cleavage is carried out under hydrogenolytic conditions in an inert solvent in the presence of a suitable catalyst, in particular 10% palladium on carbon. The hydrogen source used can also be ammonium formate.

Suitable inert solvents for the hydrogenolysis of the benzyl esters are water or the organic solvents customary for ester cleavage. These include in particular alcohols, such as methanol, ethanol, n-propanol, isopropanol, n-butanol or tert-butanol, ethers, such as diethyl ether, tetrahydrofuran, dioxane or glycol dimethyl ether, or other solvents, such as acetone, acetonitrile, dichloromethane, dimethylformamide or dimethyl sulfoxide. It is also possible to use mixtures of the solvents mentioned.

The ester cleavage is generally carried out in a temperature range of from 0° C. to +100° C., preferably at from 0° C. to +50° C. The reaction can be carried out at atmospheric, elevated or reduced pressure (for example from 0.5 to 5 bar).

The preparation of the compounds according to the invention can be illustrated by the synthesis schemes below:

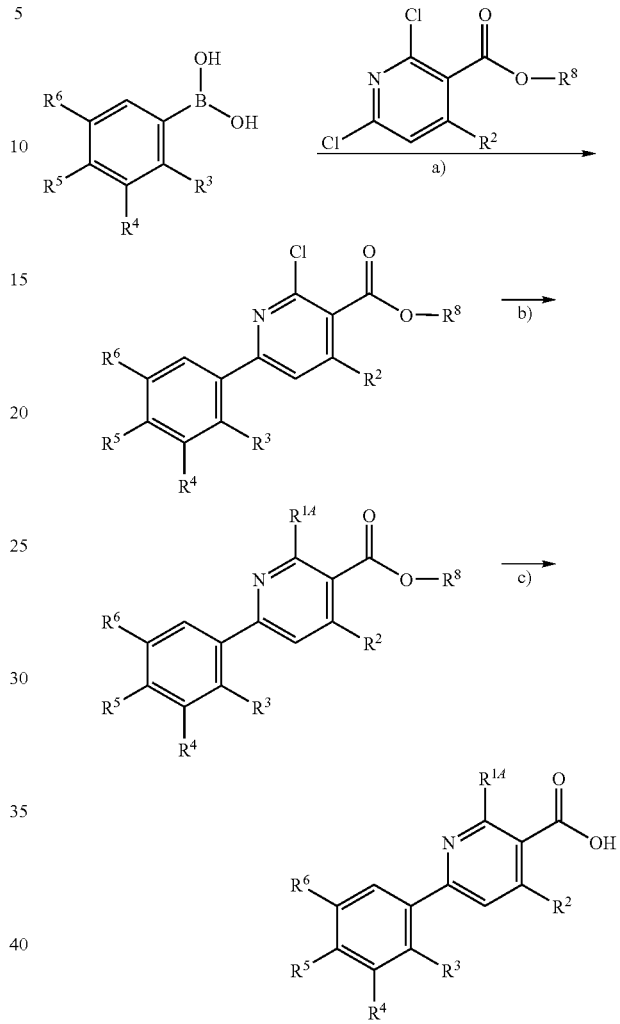

[a) Pd(PPh$_3$)$_2$Cl$_2$, tri-2-tolylphosphine, aq. K$_2$CO$_3$, DMF, RT; b) R$^{14}$—B(OH)$_2$ or R$^{14}$—ZnCl, K$_2$CO$_3$, Pd(PPh$_3$)$_4$, DMF, RT; c) KOH, isopropanol, RT—reflux temperature].

Scheme 4

-continued
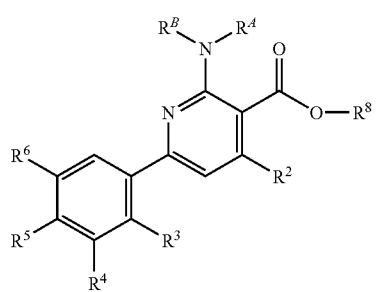
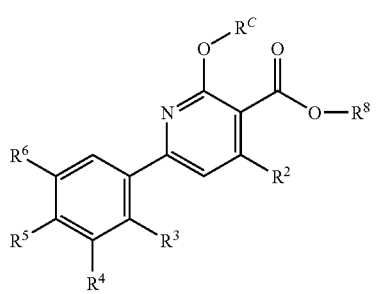
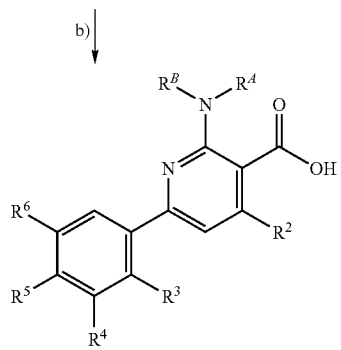
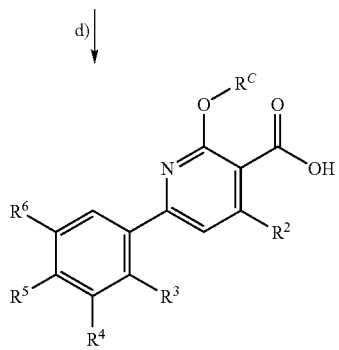
[a) triethylamine, THF, reflux temperature; b) KOH, isopropanol or ethanol, RT to 130° C.; c) n-BuLi or NaH, RT, then reflux temperature; d) aq. NaOH, ethanol, 90° C.].
Scheme 5
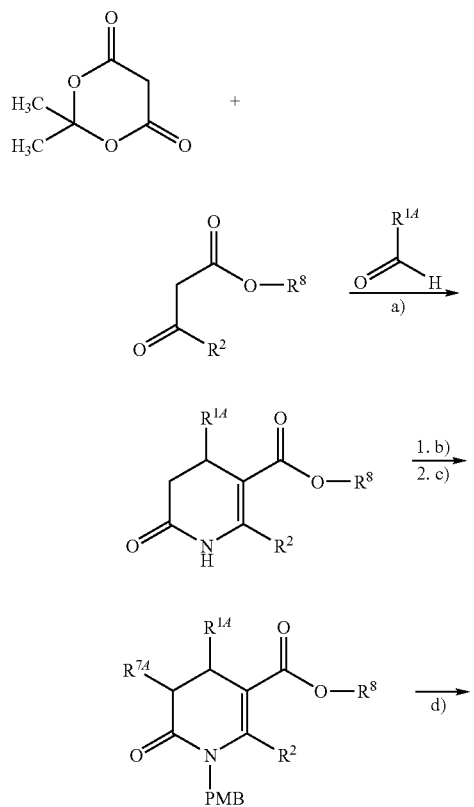
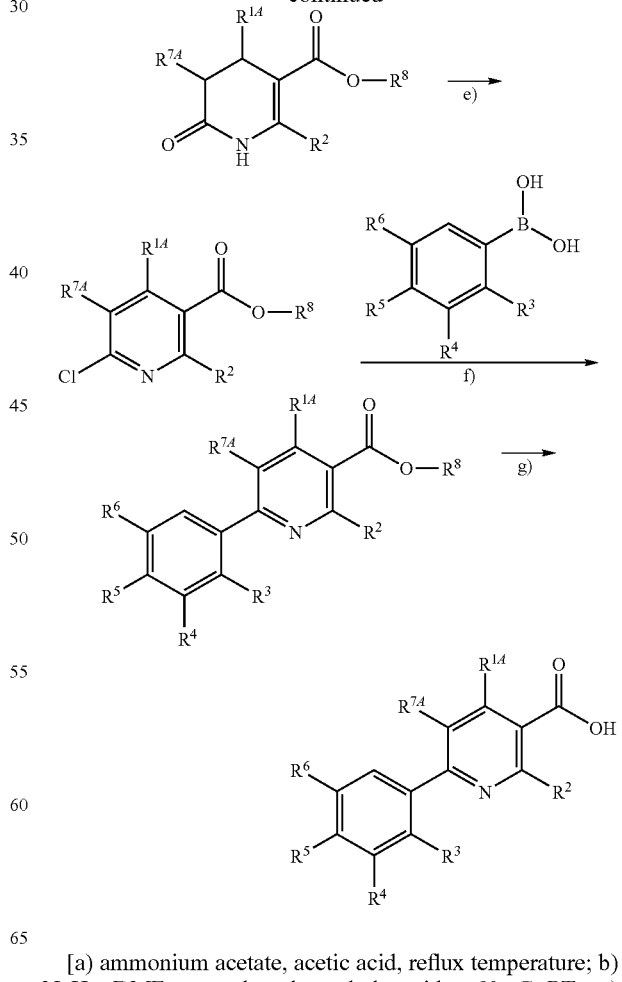
[a) ammonium acetate, acetic acid, reflux temperature; b) NaH, DMF, p-methoxybenzyl bromide, 0° C.-RT; c)

LHMDS, THF, −78° C.-RT; d): cerium ammonium nitrate, acetonitrile, RT e): DDQ, POCl₃, benzene reflux temperature; f) K₂CO₃, (PPh₃)₂PdCl₂, tri-2-tolylphosphine, dioxane, 60° C.; g) KOH. isopropanol or ethanol, RT to 160° C.].

for the primary and/or secondary prevention and treatment of cardiovascular disorders caused by disturbances in fatty acid glucose metabolism. Such disorders include dyslipidaemias (hypercholesterolaemia, hypertriglyceridaemia, elevated Scheme 6

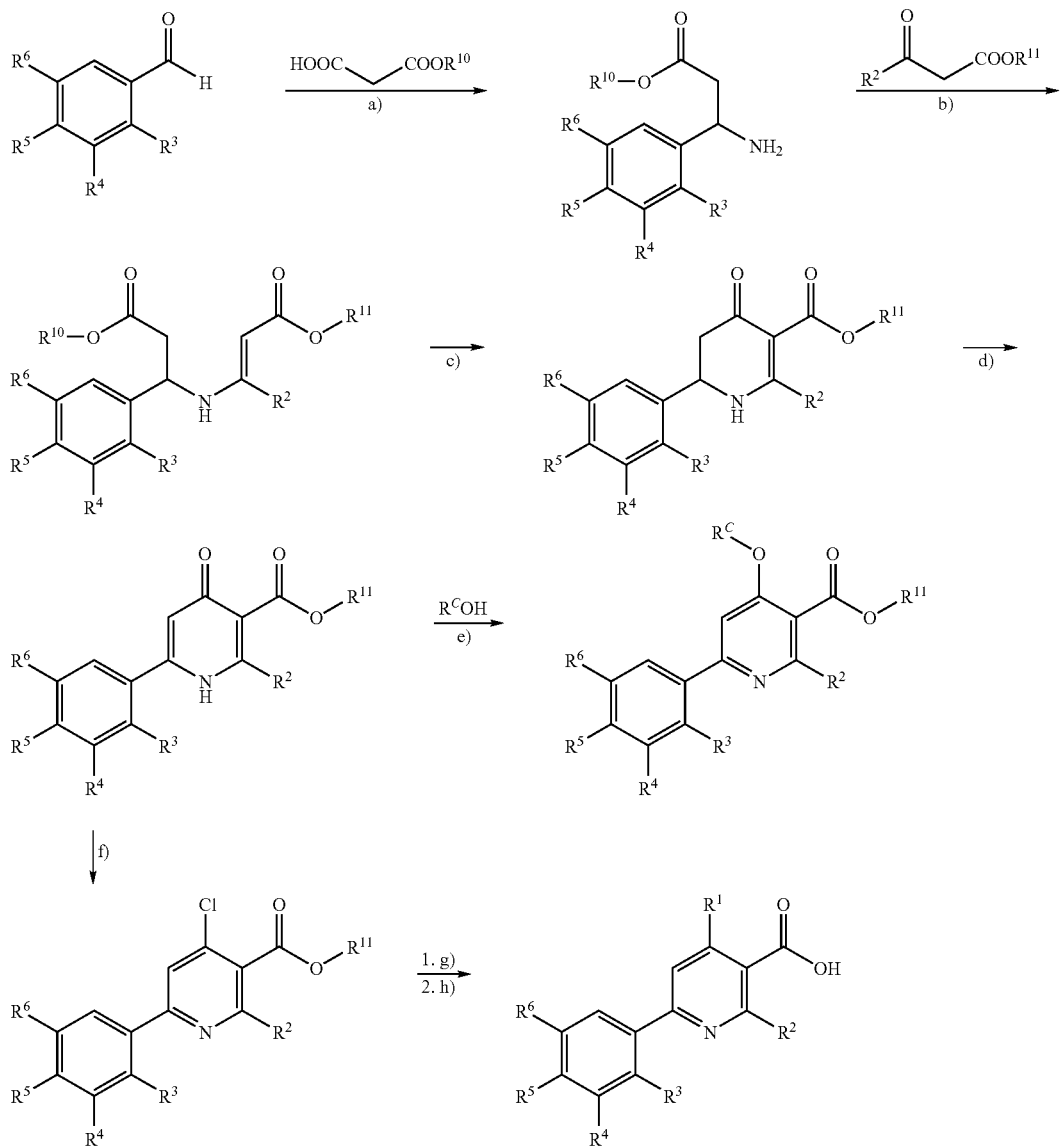

[a) ammonium acetate, ethanol, reflux temperature; b) acetic acid, benzene, reflux temperature, water separator; c) KOtBu, tBuOH, 60° C.; d) DDQ, benzene; e) DIAD, triphenylphosphine; f) POCl₃, DMF; g) for $R^1$=—$NR^AR^B$: $HNR^AR^B$, triethylamine, THF, reflux temperature, $R^1$=—$OR^C$: $HOR^C$, NaH, THF, reflux temperature, für $R^1$=$R^{1A}$: $R^{1A}$—B(OH)₂ or $R^{1A}$—ZnCl, K₂CO₃, Pd(PPh₃)₄, DMF, RT, h) KOH, isopropanol or ethanol, RT to 160° C.]

The compounds according to the invention have useful pharmacological properties and can be used for the prevention and treatment of disorders in humans and animals.

The compounds according to the invention are highly effective PPAR-alpha modulators and additionally have increased metabolic stability. They are suitable in particular concentrations of postprandial plasma triglycerides, hypoalphalipoproteinaemia, combined hyperlipidaemias), arteriosclerosis and metabolic disorders (metabolic syndrome, hyperglycaemia, insulin-dependent diabetes, non-insulin-dependent diabetes, gestation diabetes, hyperinsulinaemia, insulin resistance, glucose intolerance, obesity (adipositas) and late sequalae of diabetes, such as retinopathy, nephropathy and neuropathy).

As highly effective PPAR-alpha modulators, the compounds according to the invention are also particularly suitable for primary and/or secondary prevention and treatment of heart failure.

In the context of the present invention, the term heart failure includes both specific and related types of disease, such as right heart failure, left heart failure, global failure, heart failure induced by hypertension, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

Further independent risk factors for cardiovascular disorders which can be treaded by the compounds according to the invention are high blood pressure, ischaemia, myocardial infarction, angina pectoris, myocardial insufficiency, restenosis, pulmonary hypertension, elevated levels of fibrinogen and of LDL of low density and also elevated concentrations of plasminogen activator inhibitor 1 (PAI-1).

In addition, the compounds according to the invention can also be used for the treatment and/or prevention of cancerous diseases, such as, for example, skin cancer, breast cancer, brain tumors, head/neck tumors, liposarcomas, carcinomas of the eye, the gastrointestinal tract, the thyroid gland, the liver, the pancreas, the respiratory organs, the kidney, the ureter, the prostate, the genital tract and their distant metastases, and also lymphomas, sarcomas and leukemias.

In addition, the compounds according to the invention can also be used for the treatment and/or prevention of micro- and macrovascular damage (vasculitis), reperfusion damage, arterial and venous thromboses, oedema, of disorders of the central nervous system and neurodegenerative disorders (strokes, Alzheimer's disease, Parkinson's disease, dementia, epilepsy, depression, multiple sclerosis), of inflammatory disorders, immune disorders (Crohn's disease, ulcerative colitis, lupus erythematodes, rheumatoid arthritis, asthma), chronic obstructive pulmonary disease (chronic bronchitis, COPD), renal disorders (glomerulonephritis), disorders of the thyroid gland (hyperthyreosis), disorders of the pancreas (pancreatitis), fibrosis of the liver, skin disorders (psoriasis, acne, eczema, neurodermitis, dermatitis, keratitis, formation of scars, formation of warts, frostbites), sepsis, viral diseases (HPV, HCMV, HIV), cachexia, osteoporosis, gout, incontinence, and also for wound healing and angiogenesis.

The activity of the compounds according to the invention can be examined, for example, in vitro by the transactivation assay described in the experimental section.

The in vivo activity of the compounds according to the invention can be examined, for example, by the tests described in the experimental section.

The present invention furthermore provides the use of the compounds according to the invention for the treatment and/or prevention of disorders, in particular the disorders mentioned above.

The present invention also provides the use of the compounds according to the invention for preparing a medicament for the treatment and/or prevention of disorders, in particular the disorders mentioned above.

The present invention also provides a method for the treatment and/or prevention of disorders, in particular the disorders mentioned above, using an effective amount of at least one compound according to the invention.

The present invention also provides the compounds according to the invention for use in a process for the treatment and/or prophylaxis of dyslipidemias, arteriosclerosis and heart failure.

The compounds according to the invention can be used alone or, if required, in combination with other active compounds. The present invention furthermore provides medicaments comprising at least one compound according to the invention and one or more further active compounds, in particular for the treatment and/or prevention of the disorders mentioned above.

Suitable active compounds for combinations are, by way of example and by way of preference: substances which modulate lipid metabolism, antidiabetics, hypotensive agents, perfusion-enhancing and/or antithrombotic agents and also antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics (aspirin), antidepressants and other psychopharmaceuticals.

The present invention provides in particular combinations comprising at least one of the compounds according to the invention and at least one lipid metabolism-modulating active compound, an antidiabetic, a hypotensive compound and/or an antithrombotic agent.

Preferably, the compounds according to the invention can be combined with one or more lipid metabolism-modulating active compounds, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LPL activators, fibrates, niacin, CETP inhibitors, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers, antidiabetics mentioned in the Rote Liste 2004/11, chapter 12, and also, by way of example and by way of preference, those from the group of the sulphonylureas, biguanides, meglitinide derivatives, glucosidase inhibitors, oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861, hypotensive compounds, by way of example and by way of preference from the group of the calcium antagonists, angiotensin AII antagonists, ACE inhibitors, beta-receptor blockers, alpha-receptor blockers, ECE inhibitors and the vasopeptidase inhibitors;

antithrombotic agents, by way of example and by way of preference from the group of the platelet aggregation inhibitors or the anticoagulants;

diuretics;

aldosterone and mineralocorticoid receptor antagonists;

vasopressin receptor antagonists;

organic nitrates and NO donors;

positive-inotropic compounds;

compounds which inhibit the degradation of cyclic guanosine monophosphate (cGMP) and/or cyclic adenosine monophosphate (cAMP), such as, for example, inhibitors of phospho-diesterases (PDE) 1, 2, 3, 4 and/or 5, in particular PDE 5 inhibitors, such as sildenafil, vardenafil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

calcium sensitizers, such as, by way of example and by way of preference, levosimendan;

potassium supplements;

NO-independent, but heme-dependent stimulators of guanylate cyclase, such as, in particular, the compounds described in WO 00/06568, WO 00/06569, WO 02/42301 and WO 03/095451;

NO- and heme-independent activators of guanylate cyclase, such as, in particular, the compounds described in WO 01/19355, WO 01/19776, WO 01/19778, WO 01/19780, WO 02/070462 and WO 02/070510;

inhibitors of human neutrophil elastase (TINE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib; and/or compounds which modulate the energy metabolism of the heart, such as, for example, eto-moxir, dichloroacetate, ranolazine and trimetazidine.

Lipid metabolism-modifying active compounds are to be understood as meaning, preferably, compounds from the group of the HMG-CoA reductase inhibitors, squalene synthesis inhibitors, ACAT inhibitors, cholesterol absorption inhibitor, MTP inhibitors, lipase inhibitors, thyroid hormones and/or thyroid mimetics, niacin receptor agonists, CETP inhibitors. PPAR-gamma agonists, PPAR-delta agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705 or CETP vaccine (Avant).

In a preferred embodiment of the invention, the compounds according to the invention are administered in combination with a PPAR-gamma agonist, such as, by way of example and by way of preference, pioglitazone or rosiglitazone.

In a preferred embodiment of the invention, the compounds according to the invention are administered in combination with a PPAR-delta agonist, such as, by way of example and by way of preference, GW-501516.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with a antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycaemic active compounds. Here, insulin and insulin derivatives include both insulins of animal, human or biotechnological origin and also mixtures thereof. The orally effective hypoglycaemic active compounds preferably include sulphonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulphonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a PPAR-gamma agonist, for example from the class of the thiazolidinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a diuretic, such as; by way of example and by way of preference, a loop diuretic, such as furosemide, bumetanide or torsemide, or a thiazide diuretic or a thiazide-like diuretic, such as chlorothiazide or hydrochlorothiazide.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonists, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate. molsidomine or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan or telmisartan.

In a preferred embodiment of the invention, the compounds according to the invention are administered in combination with an ACE inhibitor, such as, by way of example and by way of preference, enalapril, captopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol oder bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with an antisympathotonic agent, such as, by way of example and by way of preference, reserpine, clonidine or alpha-methyl-dopa, or in combination with a potassium channel agonist, such as, by way of example and by way of preference, minoxidil, diazoxide, dihydralazine or hydralazine.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active compounds selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

The compounds according to the invention can be employed for the treatment and/or prophylaxis of cancerous diseases, alone or, if required, in combination with other antitumor agents. The present invention provides in particular combinations of at least one compound according to the invention with at least one other antitumor agent selected from the group consisting of alkylating agents, antimetabolites, antitumor agents derived from plants, active compounds for hormone therapy, topoisomerase inhibitors, camptothecin derivatives, kinase inhibitors, targeted medicaments, antibodies, immunoconjugates, interferon and/or immunomodulators, antiangiogen compounds, antisense-RNA and RNA interference, and other antitumor medicaments.

The following may be mentioned by way of example and by way of preference as suitable active compounds for combinations:

- alkylating agents, such as, for example, chlormethine N-oxide, cyclophosphamide, ifosfamide, thiotepa, ranimustine, nimustine, temozolomide, altretamine, apaziquone, brostallicin, bendamustin, carmustine, estramustin, fotemustine, glufosfamide, mafosfamide and mitolactol; platinum-coordinated alkylating agents, such as, by way of example, cisplatin, carboplatin, eptaplatin, lobaplatin, nedaplatin, oxaliplatin and satraplatin;
- antimetabolites, such as, for example, methotrexate, 6-mercaptopurin riboside, mercaptopurin, 5-fluorouracil alone or in combination with leucovorin, tegafur, doxifluridine, carmofur, cytarabine, cytarabine ocfosfate, enocitabine, gemcitabine, fludarabine, 5-azacitidine, capecitabine, cladribine, clofarabine, decitabine, eflornithine, ethynylcytidine, cytosine arabinoside, hydroxyurea, melphalan, nelarabine, nolatrexed, ocfosfat, disodium premetrexed, pentostatin, pelitrexol, raltitrexed, triapine, trimetrexate, vidarabine, vincristine, and vinorelbine;
- active compounds for hormone therapy, such as, for example, exemestane, Lupron, anastrozole, doxercalciferol, fadrozole, formestane, 11-beta hydroxysteroid dehydrogenase-1 inhibitors, 17-alpha hydroxylase/17, 20 lyase inhibitors, such as abiraterone acetate, 5-alpha-reductase inhibitors, such as, for example, finasterid and epristeride, anti-estrogens, such as tamoxifen citrate and fulvestrant, Trelstar, toremifene, raloxifene, lasofoxifen, letrozole, anti-androgens, such as bicalutamide, flutamide, mifepristone, nilutamide, Casodex and also anti-progesterones, and combinations thereof;
- antitumor agents derived from plants, such as, for example, mitosis inhibitors, such as epothilones (sagopilone, ixabepilone and epothilone B), vinblastine, vinflunine, docetaxel, and paclitaxel;
- cytotoxic topoisomerase inhibitors, such as, for example, aclarubicin, doxorubicin, amonafid, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposid, and combinations thereof;
- immunological active compounds, by way of example and by way of preference from the group of the interferons, such as, for example, interferon alpha, interferon alpha-2a, interferon alpha-2b, interferon beta, interferon gamma-1a and interferon gamma-n1, and other immunostimulants, such as, for example, L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonennin, teceleukin, thymafasin, tositumomab, Virulizin, cpratuzumab, mitumomab, oregovomab, pemtumomab and Provenge;
- immunomodulators, such as, for example, krestin, lentinan, sizofuran, picibanil, ProMun and ubenimex;
- antiangiogenic compounds, such as, for example, acitretin, aflibercept, angiostatin, Aplidin, Asentar, axitinib, Recentin, bevacizumab, brivanib alaninate, cilengitide, combretastatin, DAST, endostatin, fenretinide, halofuginone, pazopanib, ranibizumab, rebimastat, Removab, Revlimid, sorafenib, vatalanib, squalamine, sunitinib, telatinib, thalidomide, Ukrain and Vitaxin;
- VEGF inhibitors, such as, for example, sorafenib, DAST, bevacizumab, sunitinib, Recentin, axitinib, aflibercept, telatinib, brivanib alaninate, vatalanib, pazopanib and ranibizumab;
- antibodies, such as, for example, trastuzumab, cetuximab, bevacizumab, rituximab, ticilimumab, ipilimumab, lumiliximab, catumaxomab, atacicept, oregovomab and alemtuzumab;
- EGFR (HER1) inhibitors, such as, for example, cetuximab, panitumumab, vectibix, gefitinib, erlotinib and zactima;
- HER2 inhibitors, such as, for example, lapatinib, tratuzumab and pertuzumab;
- mTOR inhibitors, such as, for example, temsirolimus, sirolimus/rapamycin and everolimus;
- cMet inhibitors;
- PI3K and AKT inhibitors;
- CDK inhibitors, such as, for example, roscovitine and flavopiridol;
- spindle assembly checkpoint inhibitors and targeted mitosis inhibitors, such as PLK inhibitors, Aurora inhibitors (for example hesperadin), checkpoint kinase inhibitors and KSP inhibitors;
- HDAC inhibitors, such as, for example, panobinostat, vorinostat, MS275, belinostat and LBH589;
- inhibitors of histone methyltransferases, such as, for example, Vidaza;
- HSP90 and HSP70 inhibitors;
- proteasome inhibitors, such as bortezomib and carfilzomib;
- serine/threonine kinase inhibitors, such as, for example, MEK inhibitors and Raf inhibitors, such as sorafenib;
- farnesyl transferase inhibitors, such as, for example, tipifarnib;
- tyrosine kinase inhibitors, such as, for example, dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab and c-Kit inhibitors;
- vitamin D receptor agonists;
- corticoids, for example dexamethasone;
- thalidomide or thalidolide analogs, for example lenalidomid
- Bcl-2 protein inhibitors, such as, for example, obatoclax, oblimersen sodium and gossypol;
- CD20 receptor antagonists, such as, for example, rituximab;
- ribonucleotide reductase inhibitors, such as gemcitabine;
- tumor necrosis apoptosis-inducing ligand receptor 1 agonists, such as, for example, mapatumumab;
- 5-hydroxytryptamine receptor antagonists, such as, for example, rEV598, xaliproden, palonosetron hydrochloride, granisetron, Zindol and AB-1001;
- integrin inhibitors including alpha5-beta1 integrin inhibitors, for example E7820, JSM 6425, volociximab and endostatin;
- androgen receptor antagonists including, for example nandrolone decanoate, fluoxymesterone, Android, Prostaid, andromustine, bicalutamide, flutamide, apo-cyproterone, apo-flutamide, chlormadinone acetate, Androcur, tabi, cyproterone acetate and nilutamide;

aromatase inhibitors, such as for example, anastrozole, letrozole, testolactone, exemestane, aminoglutethimide and formestane;

matrix metalloproteinase inhibitors;

other active compounds used in the therapy of cancer including, for example, alitretinoin, Ampligen, atrasentan, bexarotene, bortezomib, boscentan, calcitriol, exisulind, fotemustine, brondonate, miltefosine, mitoxantrone, 1-asparaginase, procarbazine, dacarbazine, hydroxycarbamide, pegaspargase, pentostatin, tazaroten, Velcade, gallium nitrate, canfosfamide, darinaparsin and tretinoin.

The compounds according to the invention can also be used for treating cancerous diseases in combination with radiotherapy and/or surgical interventions.

The present invention furthermore provides medicaments comprising at least one compound according to the invention, usually together with one or more inert non-toxic pharmaceutically suitable auxiliaries, and their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, optically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compounds according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stems.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavour and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active compound, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

| Abbreviations and acronyms: | |
|---|---|
| abs. | absolute |
| Ac$_2$O | acetic anhydride |
| AcOH | acetic acid |
| aq. | aqueous |
| d | days |
| TLC | thin-layer chromatography |
| DCI | direct chemical ionization (in MS) |
| dd | doublet of doublets (in NMR) |
| DDQ | 2,3-dichloro-5,6-dicyano-1,4-benzoquinone |
| DIAD | diisopropyl azodicarboxylate |
| DMF | dimethylformamide |
| DMSO | dimethyl sulphoxide |
| dt | doublet of triplets (in NMR) |
| eq. | equivalent(s) |
| ESI | electrospray ionisation (in MS) |
| h | hour(s) |
| HPLC | high-pressure, high-performance liquid chromatography |
| LHMDS | lithium N,N-bistrimethylsilylamide |
| LC-MS | liquid chromatography-coupled mass spectroscopy |
| min | minute(s) |
| MPLC | medium-pressure chromatography |
| MS | mass spectroscopy |
| mz | multiplet, centered (in NMR) |
| n-Bu | n-butyl |
| NMR | nuclear magnetic resonance spectroscopy |
| o-Tol | ortho-tolyl |
| Ph | phenyl |
| RP | reversed phase (in HPLC) |
| RT | room temperature |
| $R_t$ | retention time (in HPLC) |
| sbr | singlet, broad (in NMR) |
| sept | septet (in NMR) |
| t-Bu | tert-butyl |
| THF | tetrahydrofuran |
| tt | triplet of triplets (in NMR) |
| UV | ultraviolet spectroscopy |
| v/v | volume ratio (of a mixture) |

LC-MS- and HPLC Methods:

Method 1 (LC-MS): MS instrument type: Micromass HPLC instrument type: HP 1100 series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS) MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 3 (LC-MS): MS instrument type: Micromass ZQ; HPLC instrument type: Waters Alliance 2795; column: Merck Chromolith SpeedROD RP-18e 100×4.6 mm; mobile phase A: 1 l of water+0.5 ml of 50% strength formic acid; mobile phase B: 1 l of acetonitrile+0.5 ml of 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm Method 4 (LC-MS): Instrument: Micromass Quattro LCZ with HPLC Agilent series 1100; column: Phenomenex Synergi 2.5μ MAX-RP 100A Mercury 20 min×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 5 (LC-MS): Instrument: Micromass Platform LCZ with HPLC Agilent series 1100; column: Thermo Hypersil GOLD 3μ 20×4 mm; mobile phase A: 1 l of water+0.5 ml of 50% strength formic acid, mobile phase B: 1 l of acetonitrile+ 0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS): Instrument: Micromass QuattroPremier with Waters HPLC Acquity; column: Thermo Hypersil GOLD 1.9μ 50×1 mm; mobile phase A: 1 l of water+0.5 ml of 50% strength formic acid, mobile phase B: 1 l of acetonitrile+ 0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 7 (LC-MS): Instrument: Micromass Quattro Micro MS with HPLC Agilent series 1100; column: Thermo Hypersil GOLD 3μ 20×4 mm; mobile phase A: 1 l of water+ 0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml)→5.00 min 100% A oven: 50° C.; flow rate: 2 ml/min; UV detection: 210 nm

STARTING MATERIALS AND INTERMEDIATES

Example 1A

Methyl 2,6-dichloro-4-(trifluoromethyl)nicotinate

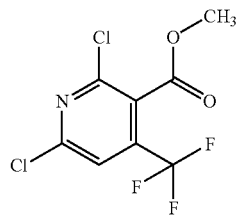

100 ml of methanol and 4.37 ml (53.9 mmol) of pyridine were cooled in an ice-bath. A solution of 10.0 g (35.9 mmol) of 2,6-dichloro-4-(trifluoromethyl)nicotinoyl chloride [Y. Tsuzuki et al., *J. Med. Chem.* 47, 2097-2109 (2004)] in 40 ml of dichloromethane was then added dropwise. The mixture was stirred with ice-cooling for one hour and then at room temperature for one hour. The reaction mixture was concentrated on a rotary evaporator. The residue was taken up in ethyl acetate and washed with saturated aqueous sodium bicarbonate solution and then with saturated aqueous sodium chloride solution. The organic phase was dried with magnesium sulfate and the solvent was removed by distillation under reduced pressure. The residue was purified by column chromatography (silica gel: isohexane/ethyl acetate=95/5). This gave 8.98 g (91% of theory) of the target compound.

LC-MS (method 1): $R_t$=2.62 min; MS (ESIpos): m/z=275 [M+H]$^+$.

$^1$H-NMR (400 MHz, DMSO-$d_6$): δ [ppm]=3.97 (s, 3H), 8.28 (s, 1H).

Example 2A

Methyl 2-chloro-6-(3-fluoro-4-methylphenyl)-4-(trifluoromethyl)nicotinate

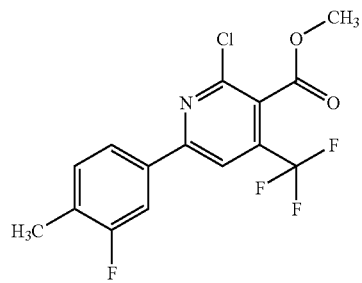

8.50 g (31.0 mmol) of Example 1A and 4.78 g (31.0 mmol) of 3-fluoro-4-methyl-phenylboronic acid were initially charged in 175 ml of dioxane. 93 ml (186 mmol) of a 2M aqueous potassium carbonate solution were then added, and the mixture was stirred at room temperature for 10 minutes. 2.18 g (3.10 mmol) of bis(triphenylphosphine)palladium(II) chloride and 0.944 (3.10 mmol) of tri-2-tolylphosphine were added. The mixture was then stirred at 60° C. overnight. After cooling, 250 ml of ethyl acetate were added, the aqueous phase was separated off and the organic phase was washed with water and with saturated aqueous sodium chloride solution. The organic phase was dried with magnesium sulfate and the solvent was removed by distillation under reduced pressure. The residue was purified by column chromatography (silica gel: isohexane/ethyl acetate=95/5). The product was crystallized from n-pentane and isolated by filtration. It was washed with a little n-pentane and dried under high vacuum. This gave 8.22 g (76% of theory) of the target compound.

LC-MS (method 2): $R_t$=2.64 min; MS (ESIpos): m/z=348 [M+H]$^+$.

$^1$H-NMR (400 MHz, DMSO-$d_6$): δ [ppm]=2.32 (s, 3H), 3.98 (s, 3H), 7.48 (t, 1H), 7.94-8.05 (m, 2H), 8.50 (s, 1H).

Example 3A

Methyl 6-(3-fluoro-4-methylphenyl)-2-isobutyl-4-(trifluoromethyl)nicotinate

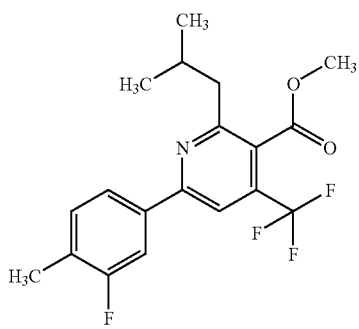

5.00 g (14.4 mmol) of Example 2A were initially charged in 100 ml abs. DMF. 57.5 ml (28.8 mmol) of isobutylzinc bromide as a 0.5M solution in TI-IF were then quickly added dropwise, and 0.831 g (0.719 mmol) of tetrakis(triphenylphosphine)palladium(0) were added. After the start of the reaction (slightly exothermal reaction), the mixture was stirred at room temperature for another two hours and then taken up in water and ethyl acetate. The reaction mixture was filtered through Celite. The organic phase was separated off and washed with water and then with saturated aqueous sodium chloride solution. After drying with magnesium sulfate, the solvent was removed by distillation under reduced pressure. The residue was purified by column chromatography (silica gel: cyclohexane–>cyclohexane/ethyl acetate=10/1). The slightly contaminated product fractions obtained in this manner were combined and, after removal of the volatile components on a rotary evaporator, purified once more by preparative HPLC (mobile phase: acetonitrile/water with 0.1% formic acid, gradient 20:80→95:5). Drying under high vacuum gave 3.14 g (59% of theory) of the target compound.

LC-MS (method 1): $R_t$=3.43 min; MS (ESIpos): m/z=370 [M+H]$^+$.

$^1$H-NMR (400 MHz, DMSO-d$_6$): δ [ppm]=0.92 (d, 6H), 2.25 (mz, 1H), 2.31 (s, 3H), 2.71 (d, 2H), 3.95 (s, 3H), 7.44 (t, 1H), 7.95-8.04 (m, 2H), 8.25 (s, 1H).

Example 4A

Methyl 6-(3-fluoro-4-methylphenyl)-2-isopropoxy-4-(trifluoromethyl)nicotinate

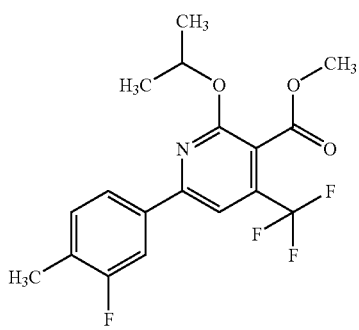

200 mg (0.575 mmol) of Example 2A were initially charged in 7 ml of tetrahydrofuran, and 0.863 ml (1.76 mmol) of lithium isopropoxide solution (2M in THF) was added. The mixture was then stirred at room temperature overnight. After removal of the volatile components on a rotary evaporator, the product was purified by preparative HPLC (mobile phase: acetonitrile/water with 0.1% formic acid, gradient 20:80→95:5). Drying under high vacuum gave 172 mg (81% of theory) of the target compound.

MS (EIpos): m/z=372 [M+H]$^+$.

$^1$H-NMR (400 MHz, DMSO-d$_6$): δ [ppm]=1.36 (d, 6H), 2.31 (s, 3H), 3.88 (s, 3H), 5.48 (sept, 1H), 7.45 (t, 1H), 7.94-8.01 (m, 3H).

Example 5A

Ethyl 4-isobutyl-2-methyl-6-oxo-1,4,5,6-tetrahydropyridine-3-carboxylate

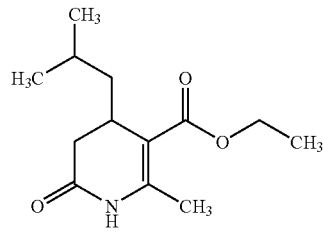

6.13 g (47.1 mmol) of ethyl acetoacetate, 6.79 g (47.1 mmol) of 2,2-dimethyl-1,3-dioxane-4,6-dione and 3.99 g (51.8 mmol) of ammonium acetate were initially charged in 50 ml of acetic acid, and 5.053 ml (47.1 mmol) of 3-methylbutyraldehyde were added. The mixture was then stirred at an oil bath temperature of 130° C. overnight. After removal of the volatile components on a rotary evaporator, the residue was taken up in 100 ml of ethyl acetate and 100 ml of water were added. The aqueous phase was extracted with ethyl acetate. The combined organic phases were then washed with aqueous 2M sodium carbonate solution and then with concentrated aqueous sodium chloride solution. After drying with magnesium sulfate, the solvent was removed on a rotary evaporator. The crude product was taken up in 25 ml of diisopropyl ether and dissolved in the hot solvent. Crystallisation was then initiated with 3 ml of n-pentane. The precipitated solid was isolated by filtration and then washed with 2 ml of diisopropyl ether. Drying under high vacuum gave 1.40 g (12% of theory) of the target compound.

LC-MS (method 3): $R_t$=1.76 min; MS (ESIpos): m/z=240 [M+H]$^+$.

$^1$H-NMR (400 MHz, DMSO-d$_6$): δ [ppm]=0.84 (d, 3H), 0.86 (d, 3H), 1.14 (t, 2H), 1.21 (t, 3H), 1.52 (sept, 1H), 2.17 (s, 3H), 2.21 (d, 1H), 2.86 (q, 1H), 4.07 (mz, 2H), 9.69 (s, 1H).

Example 6A

Ethyl 6-chloro-4-isobutyl-2-methylnicotinate

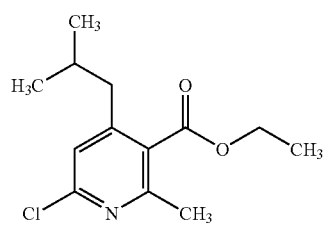

975 mg (4.07 mmol) of Example 5A, 924 mg (4.07 mmol) of DDQ and 1.90 ml (20.4 mmol) of phosphorus oxychloride were dissolved in 40 ml of benzene and stirred at reflux temperature overnight. After cooling, the mixture was taken up in 100 ml of water, made basic with 1N aqueous sodium hydroxide solution and extracted with 100 ml of ethyl acetate (3×). The organic phases were combined, dried and concentrated. Work-up was carried out by column chromatography (silica gel: cyclohexane/ethyl acetate=7/3). Drying under high vacuum gave 549 mg (53% of theory) of the target compound.

LC-MS (method 2): $R_t$=2.31 min; MS (ESIpos): m/z=256 [M+H]$^+$.

$^1$H-NMR (400 MHz, DMSO-d$_6$): δ [ppm]=0.84 (d, 6H), 1.32 (t, 3H), 1.84 (sept, 1H), 2.42 (s, 3H), 2.47 (d, 2H), 4.37 (q, 2H), 7.34 (s, 1H).

Example 7A

Ethyl 6-(3-fluoro-4-methylphenyl)-4-isobutyl-2-methylnicotinate

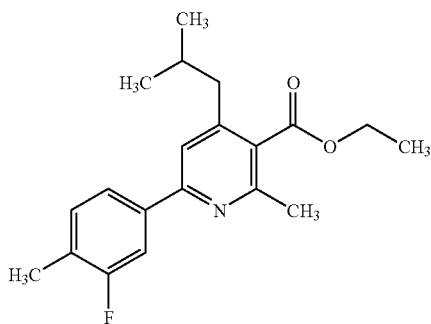

100.0 mg (0.391 mmol) of Example 6A and 60.2 mg (0.391 mmol) of 3-fluoro-4-methyl-phenylboronic acid were initially charged in 5 ml of dioxane. 1.17 ml (2.34 mmol) of a 2M aqueous potassium carbonate solution were then added, and the mixture was stirred at room temperature for 10 minutes. 27.4 mg (0.039 mmol) of bis(triphenylphosphine)palladium (II) chloride and 11.9 mg (0.039 mmol) of tri-2-tolylphosphine were added. The mixture was then stirred at 60° C. overnight. After cooling, 20 ml of ethyl acetate and 20 ml of water were added. The aqueous phase was extracted with 10 ml of ethyl acetate. The organic phases were combined and dried with magnesium sulfate. After removal of the volatile components on a rotary evaporator, the product was purified by preparative HPLC (mobile phase: acetonitrile/water with 0.1% formic acid, gradient 20:80→95:5). This gave 72 mg (56% of theory) of the target compound.

LC-MS (method 1): $R_t$=3.35 min; MS (ESIpos): m/z=330 [M+H]$^+$.

$^1$H-NMR (400 MHz, DMSO-d$_6$): δ [ppm]=0.87 (d, 6H), 1.33 (t, 3H), 1.93 (sept, 1H), 2.29 (s, 3H), 3.32 (s, 3H), 4.38 (q, 2H), 7.41 (t, 1H), 7.77 (s, 1H), 7.85-7.92 (m, 2H).

Example 8A

Ethyl 6-(3,5-difluorophenyl)-4-isobutyl-2-methylnicotinate

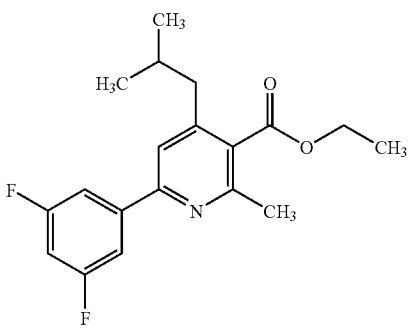

100.0 mg (0.391 mmol) of Example 6A and 60.2 mg (0.391 mmol) of 3,5-difluorophenylboronic acid were initially charged in 5 ml of dioxane. 1.17 ml (2.34 mmol) of a 2M aqueous potassium carbonate solution were then added, and the mixture was stirred at room temperature for 10 minutes. 27.4 mg (0.039 mmol) of bis(triphenylphosphine)palladium (II) chloride and 11.9 mg (0.039 mmol) of tri-2-tolylphosphine were added. The mixture was then stirred at 60° C. overnight. After cooling, 20 ml of ethyl acetate and 20 ml of water were added. The aqueous phase was extracted with 10 ml of ethyl acetate. The organic phases were combined and dried with magnesium sulfate. After removal of the volatile components on a rotary evaporator, the product was purified by preparative HPLC (mobile phase: acetonitrile/water with 0.1% formic acid, gradient 20:80→95:5). This gave 90 mg (69% of theory) of the target compound.

LC-MS (method 1): $R_t$=3.34 min; MS (ESIpos): m/z=334 [M+H]$^+$.

$^1$H-NMR (400 MHz, DMSO-d$_6$): δ [ppm]=0.87 (d, 6H), 1.34 (t, 3H), 1.96 (sept, 1H), 4.39 (q, 2H), 7.34 (tt, 1H), 7.81-7.92 (m, 3H).

Example 9A

Ethyl 6-(3-fluorophenyl)-4-isobutyl-2-methylnicotinate

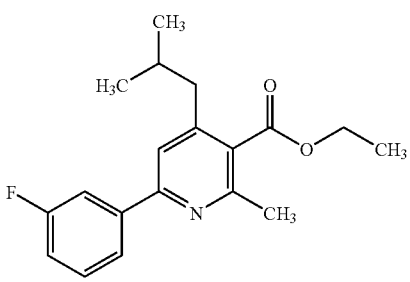

100.0 mg (0.391 mmol) of Example 6A and 54.7 mg (0.391 mmol) of 3-fluorophenylboronic acid were initially charged in 5 ml of dioxane. 1.17 ml (2.34 mmol) of a 2M aqueous potassium carbonate solution were then added, and the mixture was stirred at room temperature for 10 minutes. 27.4 ma (0.039 mmol) of bis(triphenylphosphine)palladium(II) chloride and 11.9 mg (0.039 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 64 mg (52% of theory) of the target compound.

LC-MS (method 1): $R_t$=3.24 min; MS (ESIpos): m/z=316 [M+H]$^+$.

$^1$H-NMR (400 MHz, DMSO-d$_6$): δ [ppm]=0.88 (d, 6H), 1.34 (t, 3H), 1.94 (sept, 1H), 3.32 (s, 3H), 4.39 (q, 2H), 7.30 (dt, 1H), 7.54 (mz, 1H), 7.81 (s, 1H), 7.93 (mz, 1H), 7.98 (d, 1H).

Example 10A

Methyl 6-(3-fluoro-4-methylphenyl)-2-(isopropylamino)-4-(trifluoromethyl)nicotinate

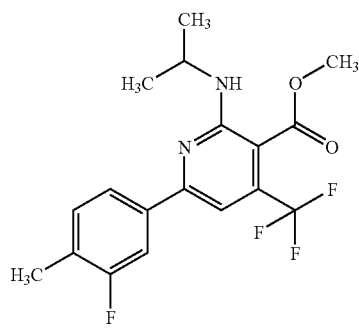

150.0 mg (0.431 mmol) of Example 2A and 0.055 ml (0.647 mmol) of isopropylamine were initially charged in 3 ml of THF. 0.150 ml (1.08 mmol) of triethylamine was then added, and the mixture was reacted in a closed vessel at 70° C. overnight. After removal of the volatile components on a rotary evaporator, the product was purified by preparative HPLC (mobile phase: acetonitrile/water with 0.1% formic acid, gradient 20:80→95:5). This gave 95 mg (59% of theory) of the target compound.

LC-MS (method 2): $R_t$=2.99 min; MS (ESIpos): m/z=371 [M+H]$^+$.

$^1$H-NMR (400 MHz, DMSO-d$_6$): δ [ppm]=1.25 (d, 6H), 2.30 (s, 3H), 3.88 (s, 3H), 4.40 (mz, 1H), 6.67 (d, 1H), 7.41 (d, 1H), 7.44 (s, 1H), 7.87-7.95 (m, 2H).

Example 11A

Methyl 6-(3-fluoro-4-methylphenyl)-2-[isopropyl(methyl)amino]-4-(trifluoromethyl)nicotinate

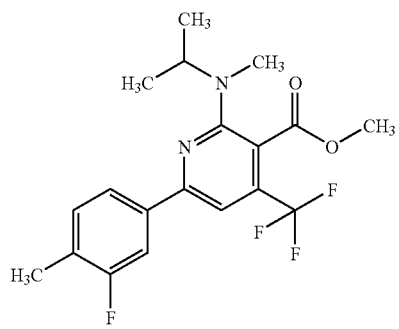

150.0 mg (0.431 mmol) of Example 2A and 0.067 ml (0.647 mmol) of N-methylpropan-2-amine were initially charged in 3 ml of THF. 0.150 ml (1.08 mmol) of triethylamine was then added, and the mixture was reacted in a closed vessel at 70° C. overnight. After removal of the volatile components on a rotary evaporator, the product was purified by preparative HPLC (mobile phase: acetonitrile/water with 0.1% formic acid, gradient 20:80→95:5). This gave 96 mg (58% of theory) of the target compound.

LC-MS (method 2): $R_t$=2.93 min; MS (ESIneg): m/z=385 [M+H]$^+$.

$^1$H-NMR (400 MHz, DMSO-d$_6$): δ [ppm]=1.20 (d, 6H), 2.30 (s, 3H), 2.79 (s, 3H), 3.87 (s, 3H), 4.71 (sept, 1H), 7.42 (t, 1H), 7.57 (s, 1H), 7.87-7.95 (m, 2H).

Example 12A

Methyl 2-ethyl-4-isobutyl-6-oxo-1,4,5,6-tetrahydropyridine-3-carboxylate

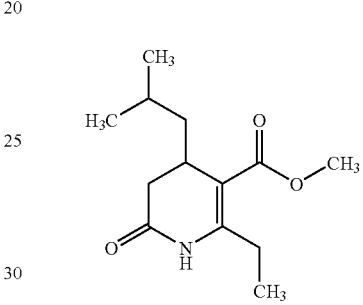

500 mg (5.81 mmol) of methyl 3-oxopentanoate, 755 mg (5.81 mmol) of 2,2-dimethyl-1,3-dioxane-4,6-dione and 492 mg (6.39 mmol) of ammonium acetate were initially charged in 5 ml of acetic acid, and 0.623 ml (5.81 mmol) of 3-methylbutyraldehyde was added. The mixture was then stirred for 14 h each at room temperature and at 130° C. After removal of the volatile components on a rotary evaporator, the residue was purified by preparative HPLC (mobile phase: acetonitrile/water with 0.1% formic acid, gradient 20:80→95:5). Drying under high vacuum gave 390 mg (28% of theory) of the target compound.

LC-MS (method 4): $R_t$=1.91 min; MS (ESIpos): m/z=238 [M−H]$^+$.

$^1$H-NMR (400 MHz, DMSO-d$_6$): δ [ppm]=0.84 (d, 3H), 0.86 (d, 3H), 1.04 (t. 3H), 1.13 (t, 2H), 1.51 (sept, 1H), 2.21 (d, 1H), 2.38-2.57 (m, 2H), 2.67 (mz, 1H), 2.86 (q, 1H), 3.63 (s, 3H), 9.70 (s, 1H).

Example 13A

Methyl 6-chloro-2-ethyl-4-isobutylnicotinate

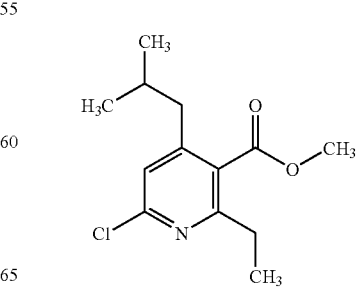

1160 mg, (4.85 mmol) of Example 12A, 1100 mg (4.85 mmol) of DDQ and 2.26 ml (24.2 mmol) of phosphorus oxychloride were dissolved in 40 ml of benzene and stirred at reflux temperature overnight. After cooling, the mixture was taken up in 100 ml of water, made basic with 1N aqueous sodium hydroxide solution and extracted with 100 ml of ethyl acetate (3×). The organic phases were combined, dried with magnesium sulfate and concentrated. Work-up was carried out by column chromatography (silica gel: cyclohexane/ethyl acetate=9/1). Drying under high vacuum gave 584 mg (42% of theory) of the target compound in a purity of 90% (LC-MS).

LC-MS (method 4): $R_t$=2.55 min; MS (ESIpos): m/z=256 [M+H]$^+$.

$^1$H-NMR (400 MHz, DMSO-d$_6$): δ [ppm]=0.83 (d, 6H), 1.17 (t, 3H), 1.83 (sept, 1H), 2.45 (d, 2H), 2.66 (q, 2H), 3.89 (s, 3H), 7.35 (s, 1H).

Example 14A

Methyl 2-ethyl-6-(3-fluoro-4-methylphenyl)-4-isobutylnicotinate

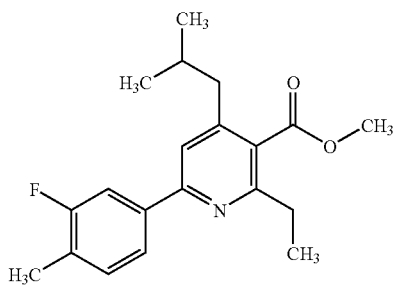

149.0 mg (0.583 mmol) of Example 13A and 89.7 mg (0.583 mmol) of 3-fluoro-4-methylphenylboronic acid were initially charged in 5 ml of dioxane. 1.75 ml (3.50 mmol) of a 2M aqueous potassium carbonate solution were then added, and the mixture was stirred at room temperature for 10 minutes. 40.9 mg (0.058 mmol) of bis(triphenylphosphine)palladium(II) chloride and 17.7 mg (0.058 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 137 mg (64% of theory) of the target compound.

LC-MS (method 2): $R_t$=2.92 min; MS (ESIpos): m/z=330 [M+H]$^+$.

$^1$H-NMR (400 MHz, DMSO-d$_6$): δ [ppm]=0.87 (d, 6H), 1.26 (t, 3H), 1.92 (sept, 1H), 2.29 (s, 3H), 2.74 (q, 2H), 3.89 (s, 3H), 7.41 (t, 1H), 7.77 (s, 1H), 7.87-7.93 (m, 2H).

Example 15A

Methyl 2-ethyl-6-(3-fluorophenyl)-4-isobutylnicotinate

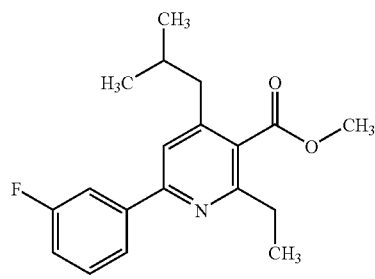

100.0 mg (0.352 mmol) of Example 13A and 49.2 mg (0.352 mmol) of 3-fluorophenylboronic acid were initially charged in 5 ml of dioxane. 1.06 ml (2.11 mmol) of a 2M aqueous potassium carbonate solution were then added, and the mixture was stirred at room temperature for 10 minutes. 24.7 mg (0.035 mmol) of bis(triphenylphosphine)palladium (II) chloride and 10.7 mg (0.035 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 56 mg (50% of theory) of the target compound.

LC-MS (method 4): $R_t$=2.95 min; MS (ESIpos): m/z=316 [M+H]$^+$.

$^1$H-NMR (400 MHz, DMSO-d$_6$): δ [ppm]=0.87 (d, 6H), 1.27 (t, 3H), 1.93 (sept, 1H), 2.76 (q, 2H), 3.90 (s, 3H), 7.30 (dt, 1H), 7.55 (mz, 1H), 7.82 (s, 1H), 7.95 (mz, 1H), 8.00 (d, 1H).

Example 16A

Methyl 2-ethyl-6-(3,5-difluorophenyl)-4-isobutylnicotinate

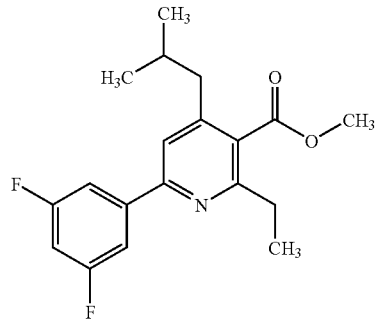

100.0 mg (0.352 mmol) of Example 13A and 55.6 mg (0.352 mmol) of 3,5-difluorophenylboronic acid were initially charged in 5 ml of dioxane. 1.06 ml (2.11 mmol) of a 2M aqueous potassium carbonate solution were then added, and the mixture was stirred at room temperature for 10 minutes. 24.7 mg (0.035 mmol) of bis(triphenylphosphine)palladium (II) chloride and 10.7 mg (0.035 mmol) of tri-2-tolylphosphine were added. The mixture was then stirred at 60° C.

overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 73 mg (62% of theory) of the target compound.

LC-MS (method 1): $R_t$=3.37 min; MS (ESIpos): m/z=334 [M+H]$^+$.

$^1$H-NMR (400 MHz, DMSO-d$_6$): δ [ppm]=0.87 (d, 6H), 1.26 (t, 3H), 1.95 (sept, 1H), 2.76 (q, 2H), 3.91 (s, 3H), 7.35 (tt, 1H), 7.84-7.93 (m, 3H).

Example 17A

Ethyl 4-isobutyl-6-oxo-2-(trifluoromethyl)-1,4,5,6-tetrahydropyridine-3-carboxylate

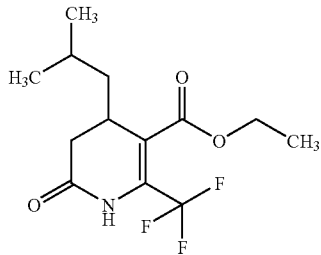

2.00 g (23.2 mmol) of ethyl-4,4,4-trifluoro-3-oxobutanoate, 3.35 g (23.2 mmol) of 2,2-dimethyl-1,3-dioxane-4,6-dione and 1.97 g (25.5 mmol) of ammonium acetate were initially charged in 20 ml of acetic acid, and 2.49 ml (23.2 mmol) of 3-methylbutyraldehyde were added. The mixture was then stirred at reflux temperature overnight. After removal of the volatile components on a rotary evaporator, another 8.95 g (116.1 mmol) of ammonium acetate were added to the residue, and the mixture was stirred at 180° C. overnight. After cooling, the mixture was taken up in 200 ml of ethyl acetate/water (1/1), and the aqueous phase was extracted with ethyl acetate (2×). The combined organic phases were dried with magnesium sulfate and the solvent was removed on a rotary evaporator. Work-up was carried out by column chromatography (silica gel: cyclohexane/ethyl acetate=4/1). Drying under high vacuum gave 1.40 g (19% of theory) of the target compound.

LC-MS (method 5): $R_t$=3.56 min; MS (ESIneg): m/z=292 [M–H]$^+$.

Example 18A

Ethyl 6-chloro-4-isobutyl-2-(trifluoromethyl)nicotinate

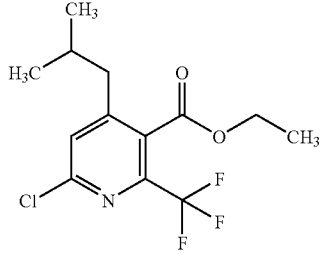

1.40 g (4.77 mmol) of Example 17A, 1.084 g (4.77 mmol) of DDQ and 2.25 ml (23.87 mmol) of phosphorus oxychloride were dissolved in 40 ml of benzene and stirred at reflux temperature overnight. After cooling, the mixture was taken up in 100 ml of water, made basic with 1N aqueous sodium hydroxide solution and extracted with 100 ml of ethyl acetate (3×). The organic phases were combined, dried with magnesium sulfate and concentrated. Work-up was carried out by column chromatography (silica gel: cyclohexane/ethyl acetate=9/1). Drying under high vacuum gave 700 mg (45% of theory) of the target compound.

LC-MS (method 1): $R_t$=3.08 min; MS (ESIpos): m/z=310 [M+H]$^+$.

$^1$H-NMR (400 MHz, DMSO-d$_6$): δ [ppm]=0.87 (d, 6H), 1.31 (t, 3H), 1.93 (sept, 1H), 2.57 (d, 2H), 4.41 (q, 2H), 7.95 (s, 1H).

Example 19A

Ethyl 6-(3-fluoro-4-methylphenyl)-4-isobutyl-2-(trifluoromethyl)nicotinate

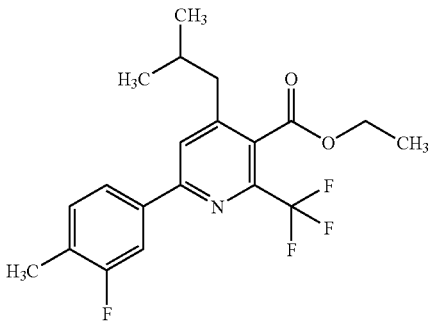

100.0 mg (0.323 mmol) of Example 18A and 49.7 mg (0.323 mmol) of 3-fluoro-4-methyl-phenylboronic acid were initially charged in 4 ml of dioxane. 0.969 ml (1.97 mmol) of a 2M aqueous potassium carbonate solution was then added, and the mixture was stirred at room temperature for 10 minutes. 22.7 mg (0.032 mmol) of bis(triphenylphosphine)palladium(II) chloride and 9.8 mg (0.032 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 73 mg (59% of theory) of the target compound.

LC-MS (method 2): $R_t$=3.00 min; MS (ESIpos): m/z=384 [M+H]$^+$.

$^1$H-NMR (400 MHz, DMSO-d$_6$): δ [ppm]=0.90 (d, 6H), 1.32 (t, 3H), 2.02 (sept, 1H), 2.32 (s, 3H), 2.61 (d, 2H), 4.41 (q, 2H), 7.48 (t, 1H), 7.94 (mz, 1H), 7.96 (s, 1H), 8.32 (s, 1H).

Example 20A

Ethyl 6-(3,5-difluorophenyl)-4-isobutyl-2-(trifluoromethyl)nicotinate

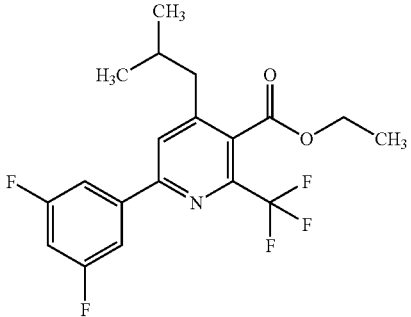

100.0 mg (0.323 mmol) of Example 18A and 51.0 mg (0.323 mmol) of 3,5-difluorophenylboronic acid were initially charged in 4 ml of dioxane. 0.969 ml (1.97 mmol) of a 2M aqueous potassium carbonate solution was then added, and the mixture was stirred at room temperature for 10 minutes. 22.7 mg (0.032 mmol) of bis(triphenylphosphine)palladium(II) chloride and 9.8 mg (0.032 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 57 mg (46% of theory) of the target compound.

LC-MS (method 2): $R_t$=2.94 min; MS (ESIpos): m/z=388 [M+H]$^+$.

$^1$H-NMR (400 MHz, DMSO-d$_6$): δ [ppm]=0.90 (d, 6H), 1.32 (t, 3H), 2.05 (sept, 1H), 2.62 (d, 2H). 4.42 (q, 2H), 7.46 (tt, 1H), 7.92 (mz, 2H), 8.43 (s, 1H).

Example 21A

Ethyl 4-isobutyl-6-(4-methylphenyl)-2-(trifluoromethyl)nicotinate

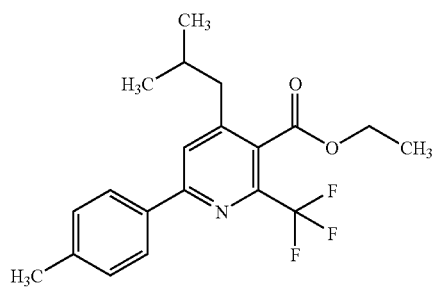

100.0 mg (0.323 mmol) of Example 18A and 43.9 mg (0.323 mmol) of 4-methylphenylboronic acid were initially charged in 4 ml of dioxane. 0.969 ml (1.97 mmol) of a 2M aqueous potassium carbonate solution was then added, and the mixture was stirred at room temperature for 10 minutes. 22.7 mg (0.032 mmol) of bis(triphenylphosphine)palladium (II) chloride and 9.8 mg (0.032 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 54 mg (46% of theory) of the target compound.

LC-MS (method 1): $R_t$=3.42 min; MS (ESIpos): m/z=366 [M+H]$^+$.

$^1$H-NMR (400 MHz, DMSO-d$_6$): δ [ppm]=0.90 (d, 6H), 1.32 (t, 3H), 2.00 (sept, 1H), 2.39 (s, 3H), 2.61 (d, 2H), 4.40 (q, 2H), 7.37 (d, 2H), 8.07 (d, 2H), 8.24 (s, 1H).

Example 22A

Ethyl 4-isobutyl-2-(trifluoromethyl)-6-[4-(trifluoromethyl)phenyl]nicotinate

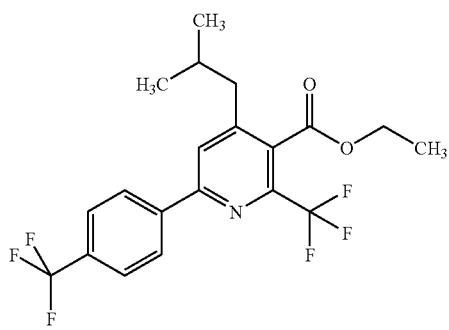

100.0 mg (0.323 mmol) of Example 18A and 61.3 mg (0.323 mmol) of 4-(trifluoromethyl)-phenylboronic acid were initially charged in 4 ml of dioxane. 0.969 ml (1.97 mmol) of a 2M aqueous potassium carbonate solution were then added, and the mixture was stirred at room temperature for 10 minutes. 22.7 mg (0.032 mmol) of bis(triphenylphosphine)palladium(II) chloride and 9.8 mg (0.032 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 57 mg (42% of theory) of the target compound.

LC-MS (method 1): $R_t$=3.44 min; MS (ESIpos): m/z=420 [M+H]$^+$.

$^1$H-NMR (400 MHz, DMSO-d$_6$): δ [ppm]=0.91 (d, 6H), 1.33 (t, 3H), 2.03 (sept, 1H), 2.65 (d, 2H), 4.42 (q, 2H), 7.94 (d, 2H), 8.39 (d, 2H), 8.42 (s, 1H).

Example 23A

Ethyl 4-isobutyl-6-(3-methylphenyl)-2-(trifluoromethyl)nicotinate

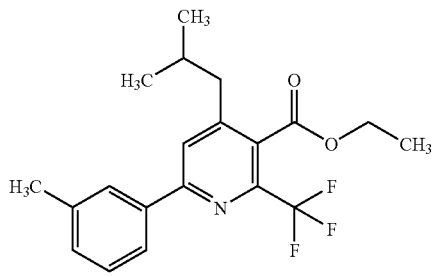

100.0 mg (0.323 mmol) of Example 18A and 43.9 mg (0.323 mmol) of 3-methylphenylboronic acid were initially charged in 4 ml of dioxane. 0.969 ml (1.97 mmol) of a 2M aqueous potassium carbonate solution were then added, and the mixture was stirred at room temperature for 10 minutes. 22.7 mg (0.032 mmol) of bis(triphenylphosphine)palladium (II) chloride and 9.8 mg (0.032 mmol) of tri-2-tolylphosphine were added. The mixture was then stirred at 60° C. overnight. After cooling, 20 ml of ethyl acetate and 20 ml of water were added. The organic phase was dried with magnesium sulfate.

After removal of the volatile components on a rotary evaporator, the product was purified by preparative HPLC (mobile phase: acetonitrile/water with 0.1% formic acid, gradient 20:80→95:5). This gave 53 mg (45% of theory) of the target compound.

LC-MS (method 1): $R_t$=3.42 min; MS (ESIpos): m/z=366 [M+H]$^+$.

$^1$H-NMR (400 MHz, DMSO-d$_6$): δ [ppm]=0.90 (d, 6H), 1.32 (t, 3H), 2.01 (sept, 1H), 2.42 (s, 3H), 2.62 (d, 2H), 4.41 (q, 2H), 7.35 (d, 1H), 7.45 (t, 1H), 7.96 (d, 1H), 7.99 (s, 1H), 8.26 (s, 1H).

Example 24A

Methyl 2-chloro-6-(4-chlorophenyl)-4-(trifluoromethyl)nicotinate

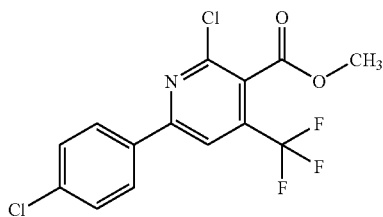

3.00 g (10.9 mmol) of Example 1A and 1.71 g (10.9 mmol) of 4-chlorophenylboronic acid were initially charged in 100 ml of dioxane. 32.8 ml (65.6 mmol) of a 2M aqueous potassium carbonate solution were then added, and the mixture was stirred at room temperature for 10 minutes. 0.768 g (1.10 mmol) of bis(triphenylphosphine)palladium(II) chloride and 0.333 (1.10 mmol) of tri-2-tolylphosphine were added. The mixture was then stirred at 60° C. for 1 h. After cooling, 250 ml of ethyl acetate/water (1/1) were added, the aqueous phase was removed and the organic phase was washed with water and with saturated aqueous sodium chloride solution. After drying with magnesium sulfate, the solvent was removed by distillation under reduced pressure. The residue was then purified by preparative HPLC (mobile phase: acetonitrile/water with 0.1% formic acid, gradient 20:80→95:5). This gave 3.29 g (86% of theory) of the target compound.

LC-MS (method 2): $R_t$=2.65 min; MS (ESIpos): m/z=350 [M+H]$^+$.

$^1$H-NMR (400 MHz, DMSO-d$_6$): δ [ppm]=3.97 (s, 3H), 7.64 (d, 2H), 8.26 (d, 2H), 8.52 (s, 1H).

Example 25A

Methyl 2-chloro-6-(4-methylphenyl)-4-(trifluoromethyl)nicotinate

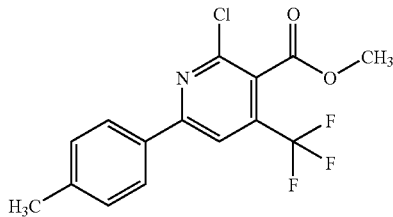

3.00 g (10.9 mmol) of Example 1A and 1.49 g (10.9 mmol) of 4-methylphenylboronic acid were initially charged in 100 ml of dioxane. 32.8 ml (65.6 mmol) of a 2M aqueous potassium carbonate solution were then added, and the mixture was stirred at room temperature for ten minutes. 0.768 g (1.10 mmol) of bis(triphenylphosphine)palladium(II) chloride and 0.333 (1.10 mmol) of tri-2-tolylphosphine were added. The mixture was then stirred at 60° C. for 1 h. After cooling, 250 ml of ethyl acetate/water (1/1) were added, the aqueous phase was removed and the organic phase was washed with water and with saturated aqueous sodium chloride solution. After drying with magnesium sulfate, the solvent was removed by distillation under reduced pressure. The residue was then purified by preparative HPLC (mobile phase: acetonitrile/water with 0.1% formic acid, gradient 20:80→95:5). This gave 2.79 g (76% of theory) of the target compound.

LC-MS (method 2): $R_t$=2.61 min; MS (ESIpos): m/z=330 [M+H]$^+$.

$^1$H-NMR (400 MHz, DMSO-d$_6$): δ [ppm]=2.40 (s, 3H), 3.97 (s, 3H), 7.38 (d, 2H), 8.13 (d, 2H), 8.43 (s, 1H).

Example 26A

Methyl 6-(4-chlorophenyl)-2-isobutyl-4-(trifluoromethyl)nicotinate

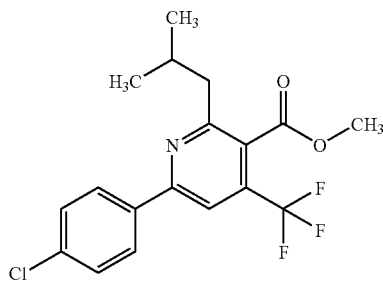

81.5 mg (0.800 mmol) of isobutylboronic acid, 317.7 mg (1.371 mmol) of silver(I) oxide, 42.0 mg (0.051 mmol) of 1,1'-bis(diphenylphosphino)ferrocenepalladium(II) chloride/dichloromethane complex and 237 mg (1.714 mmol) of potassium carbonate were initially charged under a dynamic argon atmosphere. 10 ml of tetrahydrofuran and 200.0 mg (0.571 mmol) of Example 24A were then added, and the mixture was then stirred at reflux temperature for 2 d. After cooling, the reaction mixture was filtered through kieselguhr and partitioned between water and ethyl acetate. The organic phase separated off and dried with magnesium sulfate. The solvent was then removed by distillation under reduced pressure. The residue was purified by preparative HPLC (mobile phase: acetonitrile/water with 0.1% formic acid, gradient 20:80→95:5). This gave 106 mg (50% of theory) of the target compound.

LC-MS (method 2): $R_t$=2.99 min; MS (ESIpos): m/z=372 [M+H]$^+$.

$^1$H-NMR (400 MHz, DMSO-d$_6$): δ [ppm]=0.92 (d, 6H), 2.25 (sept, 1H), 2.71 (d, 2H), 3.94 (s, 3H), 7.62 (d, 2H), 8.24-8.30 (m, 3H).

Example 27A

Methyl 2-isobutyl-6-(4-methylphenyl)-4-(trifluoromethyl)nicotinate

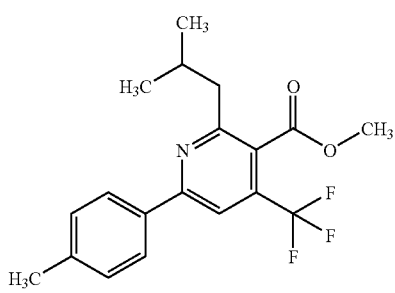

86.6 mg (0.849 mmol) of isobutylboronic acid, 337.4 mg (1.456 mmol) of silver(I) oxide, 44.6 mg (0.055 mmol) of 1,1'-bis(diphenylphosphino)ferrocenepalladium(II) chloride/dichloromethane complex and 251 mg (1.820 mmol) of potassium carbonate were initially charged under a dynamic argon atmosphere. 10 ml of tetrahydrofuran and 200.0 mg (0.607 mmol) of Example 25A were then added, and the mixture was then stirred at reflux temperature for 2 d. After cooling, the reaction mixture was filtered through kieselguhr and partitioned between water and ethyl acetate. The organic phase was separated off and dried with magnesium sulfate. The solvent was then removed by distillation under reduced pressure. The residue was purified by preparative HPLC (mobile phase: acetonitrile/water with 0.1% formic acid, gradient 20:80→95:5). This gave 61 mg (29% of theory) of the target compound.

LC-MS (method 2): $R_t$=2.96 min; MS (ESIpos): m/z=352 [M+H]$^+$.

$^1$H-NMR (400 MHz, DMSO-d$_6$): δ [ppm]=0.92 (d, 6H), 2.25 (sept, 1H), 2.39 (s, 3H), 2.70 (d, 2H), 3.93 (s, 3H), 7.36 (d, 2H), 8.13 (d, 2H), 8.18 (s, 1H).

Example 28A

Methyl 2-isobutoxy-6-(4-methylphenyl)-4-(trifluoromethyl)nicotinate

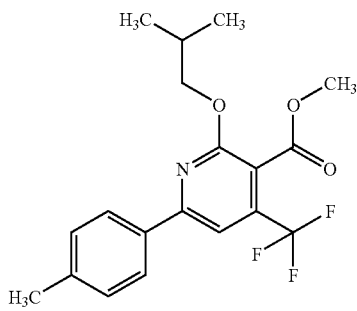

50.6 mg (0.682 mmol) of 2-methylpropan-1-ol were initially charged in 2 ml of tetrahydrofuran, and 27.3 mg (0.682 mmol) of sodium hydride (60% in paraffin oil) were added. 150 mg (0.455 mmol) of Example 25A were then added as a solution in 2 ml of tetrahydrofuran, and the mixture was stirred at reflux temperature for 2 d. After removal of the volatile components on a rotary evaporator, the residue was taken up in water and extracted with ethyl acetate (2×10 ml). The combined organic phases were dried with magnesium sulfate. The solvent was removed by distillation under reduced pressure, and the product was then purified by preparative HPLC (mobile phase: acetonitrile/water with 0.1% formic acid, gradient 20:80→95:5). Drying under high vacuum gave 29 mg (17% of theory) of the target compound.

LC-MS (method 6): $R_t$=1.75 min; MS (ESIpos): m/z=368 [M+H]$^+$.

$^1$H-NMR (400 MHz, DMSO-d$_6$): δ [ppm]=0.98 (d, 6H), 2.06 (sept, 1H), 2.38 (s, 3H), 3.88 (s, 3H). 4.29 (d, 2H), 7.35 (d, 2H), 7.90 (s, 1H), 8.11 (d, 2H).

Example 29A

Methyl 6-(4-chlorophenyl)-2-isopropoxy-4-(trifluoromethyl)nicotinate

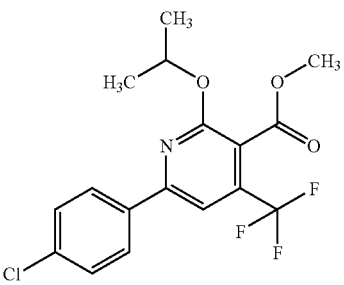

38.6 mg (0.643 mmol) of propan-2-ol were initially charged in 2 ml of tetrahydrofuran, and 25.7 mg (0.643 mmol) of sodium hydride (60% in paraffin oil) were added. 150 mg (0.428 mmol) of Example 24A were then added as a solution in 2 ml of tetrahydrofuran, and the mixture was stirred at reflux temperature for 2 d. After removal of the volatile components on a rotary evaporator, the residue was taken up in water and the mixture was extracted with ethyl acetate (2×10 ml). The combined organic phases were dried with magnesium sulfate. The solvent was removed by distillation under reduced pressure, and the product was then purified by preparative HPLC (mobile phase: acetonitrile/water with 0.1% formic acid, gradient 20:80→95:5). Drying under high vacuum gave 49 mg (31% of theory) of the target compound.

LC-MS (method 6): $R_t$=1.69 min; MS (ESIpos): m/z=374 [M+H]$^+$.

$^1$H-NMR (400 MHz, DMSO-d$_6$): δ [ppm]=1.35 (d, 6H), 3.88 (s, 3H), 5.48 (sept, 1H), 7.61 (d, 2H), 7.97 (s, 1H), 8.23 (d, 2H).

Example 30A

Methyl 6-(4-chlorophenyl)-2-isobutoxy-4-(trifluoromethyl)nicotinate

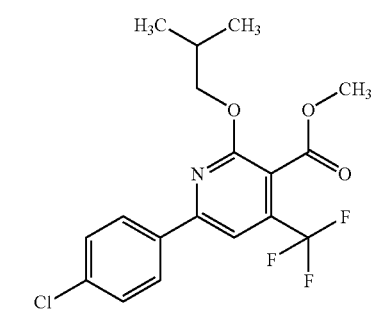

47.6 mg (0.643 mmol) of 2-methylpropan-1-ol were initially charged in 2 ml of tetrahydrofuran, and 25.7 mg (0.643 mmol) of sodium hydride (60% in paraffin oil) were added. 150 mg (0.428 mmol) of Example 24A were then added as a solution in 2 ml of tetrahydrofuran, and the mixture was stirred at reflux temperature for 2 d. After removal of the volatile components on a rotary evaporator, the residue was taken up in water and the mixture was extracted with ethyl acetate (2×10 ml). The combined organic phases were dried with magnesium sulfate. The solvent was removed by distillation under reduced pressure, and the product was then purified by preparative HPLC (mobile phase: acetonitrile/water with 0.1% formic acid, gradient 20:80→95:5). Drying under high vacuum gave 52 mg (31% of theory) of the target compound.

LC-MS (method 6): $R_t$=1.77 min; MS (ESIpos): m/z=388 [M+H]$^+$.

$^1$H-NMR (400 MHz, DMSO-d$_6$): δ [ppm]=0.98 (d, 6H), 2.06 (sept, 1H), 3.89 (s, 3H), 4.29 (d, 2H), 7.61 (d, 2H), 7.99 (s, 1H), 8.25 (d, 2H).

Example 31A

Methyl 2-ethyl-4-isobutyl-6-(4-methylphenyl)nicotinate

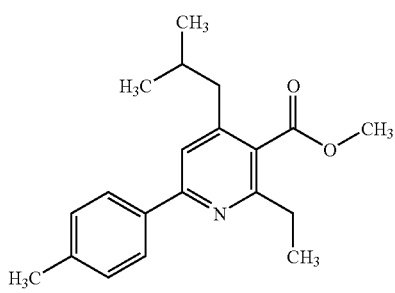

200.0 mg (0.782 mmol) of Example 13A and 106 mg (0.782 mmol) of 4-methyl-phenylboronic acid were initially charged in 6 ml of dioxane. 2.35 ml (4.69 mmol) of a 2M aqueous potassium carbonate solution were then added, and the mixture was stirred at room temperature for 10 minutes. 54.9 mg (0.078 mmol) of bis(triphenylphosphine)palladium (II) chloride and 23.8 mg (0.078 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 83 mg (34% of theory) of the target compound.

LC-MS (method 1): $R_t$=3.15 min; MS (ESIpos): m/z=312 [M+H]$^+$.

$^1$H-NMR (400 MHz, DMSO-d$_6$): δ [ppm]=0.87 (d, 6H), 1.26 (t, 3H), 1.90 (sept, 1H), 2.37 (s, 3H), 2.74 (q, 2H). 3.89 (s, 3H), 7.31 (d. 2H). 7.68 (s, 1H), 8.03 (d, 2H).

Example 32A

Methyl 6-(4-chlorophenyl)-2-ethyl-4-isobutylnicotinate

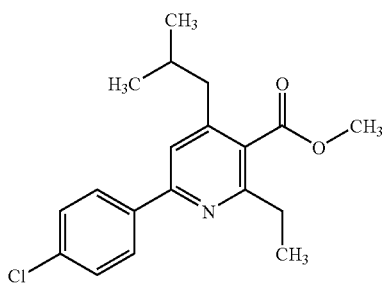

200.0 mg (0.782 mmol) of Example 13A and 122 mg (0.782 mmol) of 4-chloro-phenylboronic acid were initially charged in 6 ml of dioxane. 2.35 ml (4.69 mmol) of a 2M aqueous potassium carbonate solution were then added, and the mixture was stirred at room temperature for 10 minutes. 54.9 mg (0.078 mmol) of bis(triphenylphosphine)palladium (II) chloride and 23.8 mg (0.078 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 146 mg (56% of theory) of the target compound.

LC-MS (method 1): $R_t$=3.26 min; MS (ESIpos): m/z=332 [M+H]$^+$.

$^1$H-NMR (400 MHz, DMSO-d$_6$): δ [ppm]=0.87 (d, 6H), 1.26 (t, 3H), 1.92 (sept, 1H), 2.75 (q, 2H), 3.90 (s, 3H), 7.57 (d, 2H), 7.77 (s, 1H), 8.17 (d, 2H).

Example 33A

Ethyl 4-isobutyl-1-(4-methoxybenzyl)-5-methyl-6-oxo-2-(trifluoromethyl)-1,4,5,6-tetrahydro-pyridine-3-carboxylate

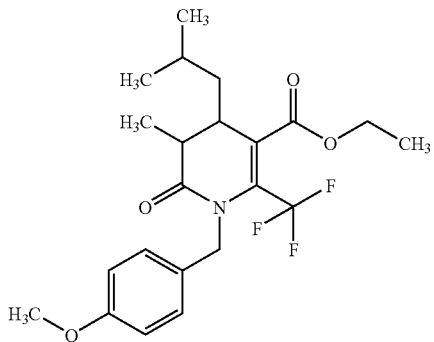

1.60 g (5.45 mmol) of Example 17A were initially charged in 12 ml DMF, and 0.262 g (6.54 mmol) of sodium hydride (60% in paraffin oil) were added a little at a time. The mixture was cooled to 0° C., and 1.11 g (5.51 mmol) of p-methoxybenzyl bromide were then added. The ice-bath was then removed, and the mixture was stirred at RT overnight. The solvent was distilled off and the residue was partitioned between ethyl acetate and water. The organic phase was dried with magnesium sulfate and the solvent was removed by distillation under reduced pressure. The crude product was purified by preparative HPLC: (mobile phase: acetonitrile/water with 0.1% formic acid, gradient 20:80→95:5). Drying under high vacuum gave 1.42 g (63% of theory) of ethyl 4-isobutyl-1-(4-methoxybenzyl)-6-oxo-2-(trifluoromethyl)-1,4,5,6-tetrahydropyridine-3-carboxylate. The identity of the intermediate was checked by LC-MS {(method 1): $R_t$=3.06 min; MS (ESIpos): m/z=414 [M+H]$^+$}. 987 mg (2.39 mmol) of the compound obtained in this manner were taken up in 12 ml of THF and cooled to −78° C. 3.58 ml (3.58 mmol) of lithium hexamethyldisilazide solution (1M in THF) were then added dropwise. After ten minutes of stirring, methyl iodide was added dropwise and the reaction mixture was slowly warmed to RT over a period of 2 h. The reaction was hydrolyzed with water and extracted with diethyl ether. The organic phase was washed with saturated aqueous ammonium chloride solution and dried with magnesium sulfate. The solvent was removed on a rotary evaporator. The crude product was purified by preparative HPLC (mobile phase: acetonitrile/water with 0.1% formic acid, gradient 20:80→95:5). Drying under high vacuum gave 910 mg (56% of theory based on Example 17A) of the target compound in diastereomerically pure form.

LC-MS (method 1): $R_t$=2.97 min; MS (ESIpos): m/z=428 [M+H]$^+$.

$^1$H-NMR (400 MHz, CDCl$_3$): δ [ppm]=0.65 (d, 3H), 0.72 (d, 3H), 0.85 (m, 1H), 0.95 (m, 1H), 1.22 (d, 3H), 1.32 (t, 3H), 1.47 (mz, 1H), 2.44-2.52 (2H), 3.78 (s, 3H), 4.20-4.31 (m, 3H), 5.28 (d, 1H), 6.83 (d, 2H), 7.26 (d, 2H).

Example 34A

Ethyl 4-isobutyl-5-methyl-6-oxo-2-(trifluoromethyl)-1,4,5,6-tetrahydropyridine-3-carboxylate

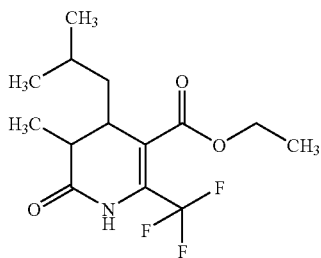

427 mg (1.00 mmol) of Example 33A were initially charged in 6 ml of acetonitrile. The mixture was cooled in an ice-bath, and 3.19 ml (6.39 mmol) of ammonium cerium(IV) nitrate solution (2M in THF) were then added dropwise. Ice-cooling was removed, and the mixture was then stirred at room temperature overnight. 20 ml of water were added, and the mixture was then extracted three times with 25 ml of dichloromethane. The combined organic phases were washed with water and dried with magnesium sulfate. The solvent was removed on a rotary evaporator. The crude product was purified by preparative HPLC (mobile phase: acetonitrile/water with 0.1% formic acid, gradient 20:80→95:5). Drying under high vacuum gave 170 mg (55% of theory) of the target compound.

LC-MS (method 1): $R_t$=2.60 min; MS (ESIpos): m/z=308 [M+H]$^+$.

$^1$H-NMR (400 MHz, CDCl$_3$): δ [ppm]=0.86-0.95 (m, 6H), 1.21 (d, 3H), 1.28-1.37 (m, 4H), 1.44 (mz, 1H), 1.68 (sept, 1H). 2.58 (q, 2H), 2.67 (dd, 2H), 7.13 (sbr, 1H).

Example 35A

Ethyl 6-chloro-4-isobutyl-5-methyl-2-(trifluoromethyl)nicotinate

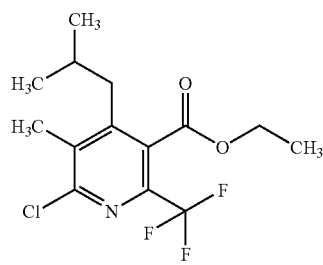

210 mg (0.683 mmol) of Example 34A, 155 mg (0.683 mmol) of DDQ and 0.32 ml (3.42 mmol) of phosphorus oxychloride were dissolved in 5 ml of benzene and stirred at reflux temperature overnight. After cooling, the mixture was taken up in 10 ml of water, made basic with 1N aqueous sodium hydroxide solution and extracted with 10 ml of ethyl acetate (3×). The organic phases were combined, dried with magnesium sulfate and concentrated. Work-up was carried out by column chromatography (silica gel: cyclohexane/ethyl acetate=9/1). Drying under high vacuum gave 84 mg (38% of theory) of the target compound.

LC-MS (method 1): $R_t$=2.97 min; MS (ESIpos): m/z=324 [M+H]$^+$.

$^1$H-NMR (400 MHz, CDCl$_3$): δ [ppm]=0.92 (d, 6H), 1.38 (t, 3H), 1.93 (sept, 1H), 2.46 (s, 3H), 2.66 (d, 2H), 4.41 (q, 2H).

Example 36A

Ethyl 6-(4-chlorophenyl)-4-isobutyl-5-methyl-2-(trifluoromethyl)nicotinate

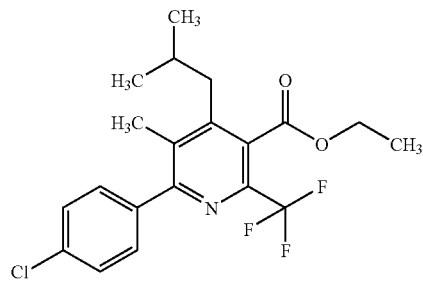

84 mg (0.259 mmol) of Example 35A and 43 mg (0.272 mmol) of 4-chlorophenylboronic acid were initially charged in 4 ml of dioxane. 0.778 ml (1.56 mmol) of a 2M aqueous potassium carbonate solution was then added, and the mixture was stirred at room temperature for 10 minutes. 18.2 mg (0.026 mmol) of bis(triphenylphosphine)palladium(II) chloride and 7.9 mg (0.026 mmol) of tri-2-tolylphosphine were added. The mixture was then stirred at 60° C. overnight. After cooling, 20 ml of ethyl acetate and 20 ml of water were added. The organic phase was dried with magnesium sulfate. After removal of the volatile components on a rotary evaporator, the product was purified by preparative HPLC (mobile phase: acetonitrile/water with 0.1% formic acid, gradient 20:80→95:5). This gave 80 mg (77% of theory) of the target compound.

LC-MS (method 1): $R_t$=3.26 min; MS (ESIpos): m/z=400 [M+H]$^+$.

$^1$H-NMR (400 MHz, CDCl$_3$): δ [ppm]=0.96 (d, 6H), 1.41 (t, 3H), 1.99 (sept, 1H), 2.35 (s, 3H), 2.70 (d, 2H), 4.43 (q, 2H), 7.44 (s, 4H).

Example 37A

Methyl 6-(3-fluoro-4-methylphenyl)-2-isobutoxy-4-(trifluoromethyl)nicotinate

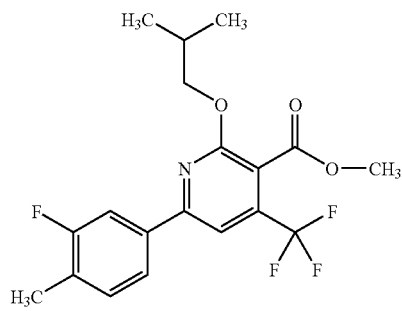

32 mg (0.431 mmol) of 2-methylpropanol and 34 mg (0.803 mmol) of sodium hydride (60% strength dispersion in mineral oil) were initially charged in 5 ml of tetrahydrofuran. The reaction mixture was stirred at room temperature for 30 minutes. 100 mg (0.288 mol) of Example 2A were then added as a solution in 2 ml of tetrahydrofuran. The mixture was then stirred at reflux temperature overnight. For work-up, the reaction mixture was adjusted to 1 using 1N hydrochloric acid. After removal of the volatile components on a rotary evaporator, the product was purified by preparative HPLC (mobile phase: acetonitrile/water, gradient 10:90→90:10). This gave 55 mg (50% of theory) of the target compound.

LC-MS (method 2): $R_t$=3.16 min; MS (ESIpos): m/z=386 [M+H]$^+$.

Example 38A

Methyl 2-ethoxy-6-(3-fluoro-4-methylphenyl)-4-(trifluoromethyl)nicotinate

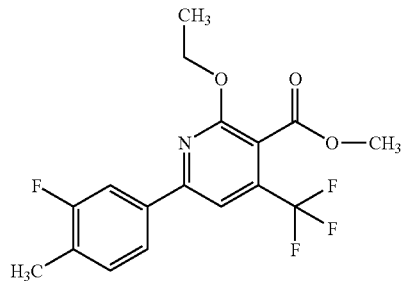

20 mg (0.431 mmol) of ethanol and 17 mg (0.431 mmol) of sodium hydride (60% strength dispersion in mineral oil) were initially charged in 5 ml of tetrahydrofuran. The reaction mixture was stirred at room temperature for 30 minutes. 100 mg (0.288 mol) of Example 2A were then added as a solution in 2 ml of tetrahydrofuran, and the mixture was stirred at reflux temperature overnight. For work-up, water was added to the reaction mixture. After removal of the volatile components on a rotary evaporator, the product was purified by preparative HPLC (mobile phase: acetonitrile/water, gradient 10:90→90:10). This gave 28 mg (28% of theory) of the target compound.

LC-MS (method 1): $R_t$=3.30 min; MS (ESIpos): m/z=358 [M+H]$^+$.

Example 39A

Methyl 2-(cyclopentylamino)-6-(3-fluoro-4-methylphenyl)-4-(trifluoromethyl)nicotinate

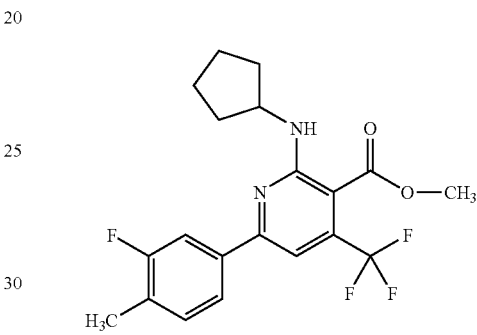

100 mg (0.288 mmol) of Example 2A and 37 mg (0.431 mmol) of cyclopentylamine in 2 ml 1,2-ethandiol were stirred at 120° C. for 3 days. Without any further work-up, the reaction mixture was purified by preparative HPLC (mobile phase: acetonitrile/water, gradient 10:90→90:10). This gave 42 mg (37% of theory) of the target compound.

LC-MS (method 1): $R_t$=3.59 min; MS (ESIpos): m/z=397 [M+H]$^+$.

Example 40A

Methyl 2-(diethylamino)-6-(3-fluoro-4-methylphenyl)-4-(trifluoromethyl)nicotinate

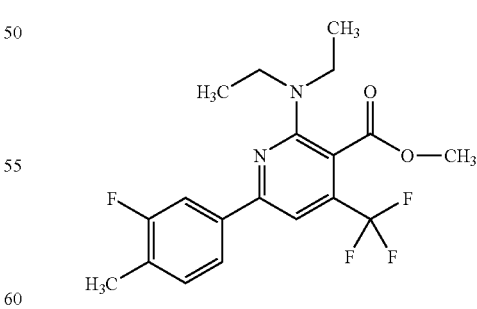

100 mg (0.288 mmol) of Example 2A and 32 mg (0.431 mmol) of diethylamine in 2 ml 1,2-ethandiol were stirred at 120° C. for 3 days. Without any further work-up, the reaction mixture was purified by preparative HPLC (mobile phase: acetonitrile/water, gradient 10:90→90:10). This gave 32 mg (29% of theory) of the target compound.

Example 41A

Methyl 6-(3-fluoro-4-methylphenyl)-2-(3-methylbutyl)-4-(trifluoromethyl)nicotinate

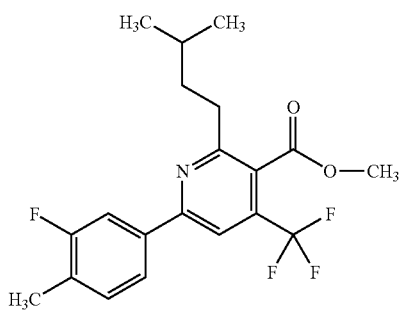

Under an atmosphere of argon, 100 mg (0.288 mmol) of Example 2A were initially charged in 2 ml DMF. 1.15 ml (0.575 mmol) of isobutylzinc bromide solution (0.5M in THF) were then added dropwise. 17 mg (0.014 mmol) of tetrakis(triphenylphosphine)palladium(0) were then added, and the mixture was stirred at room temperature for 72 h. Without any further work-up, the reaction mixture was purified by preparative HPLC (mobile phase: acetonitrile/water, gradient 10:90→90:10). This gave 33 mg (30% of theory) of the target compound.

LC-MS (method 1): $R_t$=3.53 min; MS (ESIpos): m/z=384 [M+H]$^+$.

Example 42A

Methyl 2-butyl-6-(3-fluoro-4-methylphenyl)-4-(trifluoromethyl)nicotinate

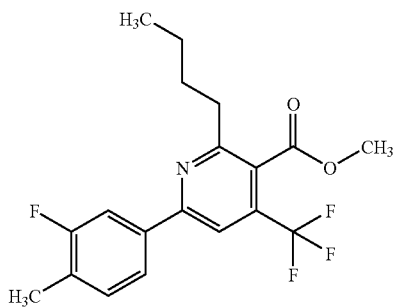

100 mg (0.288 mmol) of Example 2A were dissolved in 2 ml DMF. 1.15 ml (0.575 mmol) of butylzinc bromide solution (0.5M in THF) and 17 mg (0.014 mmol) of tetrakis(triphenylphosphine)-palladium(0) were then added. The reaction mixture was stirred at room temperature overnight. Ethyl acetate/water (1/1) were then added, the mixture was filtered through kieselguhr and the organic phase was evaporated to dryness under reduced pressure. The residue was purified by preparative HPLC (mobile phase: acetonitrile/water, gradient 10:90→90:10). This gave 49 mg (46% of theory) of the target compound.

LC-MS (method 1): $R_t$=3.44 min; MS (ESIpos): m/z=385 [M+H]$^+$.

Example 43A

Methyl 2-(cyclopropylmethoxy)-6-(3-fluoro-4-methylphenyl)-4-(trifluoromethyl)nicotinate

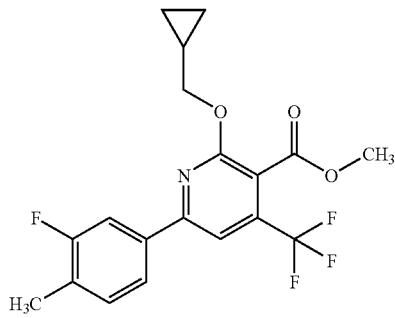

31 mg (0.431 mmol) of cyclopropylmethanol and 34 mg (0.863 mmol) of sodium hydride (60% strength dispersion in mineral oil) were initially charged in 5 ml of tetrahydrofuran. The reaction mixture was stirred at room temperature for 30 minutes. 100 mg (0.288 mol) of Example 2A were then added as a solution in 2 ml of tetrahydrofuran, and the mixture was stirred at reflux temperature overnight. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 37 mg (34% of theory) of the target compound.

LC-MS (method 4): $R_t$=3.02 min; MS (ESIpos): m/z=384 [M+H]$^+$.

Example 44A

Methyl 2-[(cyclopropylmethyl)amino]-6-(3-fluoro-4-methylphenyl)-4-(trifluoromethyl)nicotinate hydrochloride

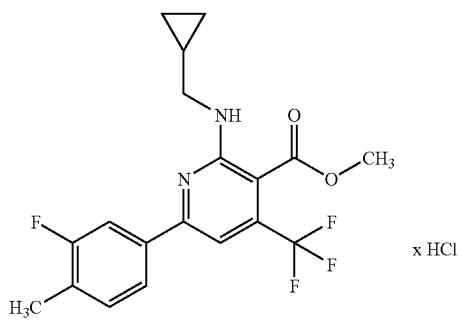

50 mg (0.144 mmol) of Example 2A, 15 mg (0.216 mmol) of 1-cyclopropylmethanamine and 37 mg (0.360 mmol) of triethylamine as a solution in 2 ml of THF were stirred at room temperature for 72 h. The reaction was checked, showing incomplete conversion. Thus, another 10 mg (0.144 mmol) of cyclopropylmethanamine and 29 mg (0.288 mmol) of triethylamine were added. The solution was then again stirred at 80° C. overnight. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave the target compound in quantitative yield.

LC-MS (method 6): $R_t$=1.75 min; MS (ESIpos): m/z=383 [M+H]$^+$–HCl.

Example 45A

Methyl 6-(3-fluoro-4-methylphenyl)-2-[(2-methoxyethyl)(methyl)amino]-4-(trifluoromethyl)-nicotinate

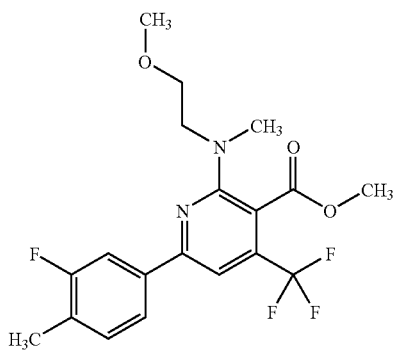

50 mg (0.144 mmol) of Example 2A, 20 mg (0.216 mmol) of 2-methoxy-N-methylethanamine and 37 mg (0.360 mmol) of triethylamine were stirred in 2 ml of THF at room temperature for 72 h. The reaction was checked, showing incomplete conversion. Thus, another 13 mg (0.144 mmol) of 2-methoxy-N-methylethanamine and 29 mg (0.288 mmol) of triethylamine were added. The mixture was then stirred at 80° C. overnight. For work-up, the reaction mixture was adjusted to pH 1 with 1 N hydrochloric acid. After removal of the volatile components on a rotary evaporator, the product was purified by preparative HPLC (mobile phase: acetonitrile/water, gradient 10:90→90:10). This gave 30 mg (52% of theory) of the target compound.

LC-MS (method 6): $R_t$=1.59 min; MS (ESIpos): m/z=400 [M+H]$^+$.

Example 46A

Methyl 2-chloro-6-(3,5-difluorophenyl)-4-(trifluoromethyl)nicotinate

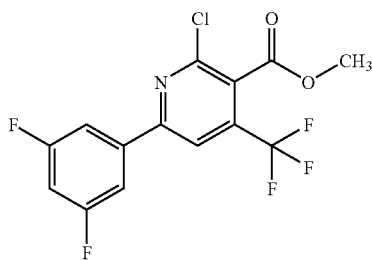

4.0 g (14.60 mmol) of Example 1A were initially charged in 80 ml of dioxane. Under argon, 2.31 g (14.60 mmol) of (3,5-difluorophenyl)boronic acid and 43.8 ml (87.60 mmol) of a 2M aqueous potassium carbonate solution were added. The mixture was stirred for 10 min. 1.03 g (1.46 mmol) of bis(triphenylphosphine)palladium(II) chloride and 0.44 g (1.460 mmol) of tri-2-tolylphosphine were then added. The reaction mixture was then heated at 60° C. overnight. After cooling, ethyl acetate/water (1/1) was added to the reaction mixture. The organic phase was separated off and washed with saturated aqueous sodium bicarbonate solution and then with saturated aqueous sodium chloride solution. It was then dried with sodium sulfate. The solvent was distilled off under reduced pressure, and the residue was subjected to column chromatography on silica gel (mobile phase: cyclohexane/ethyl acetate 30/1). This gave 4.76 g (58% of theory) of the target compound.

LC-MS (method 1): $R_t$=3.09 min; MS (ESIpos): m/z=352 [M+H]$^+$.

Example 47A

Methyl 2-(cyclopentylamino)-6-(3,5-difluorophenyl)-4-(trifluoromethyl)nicotinate

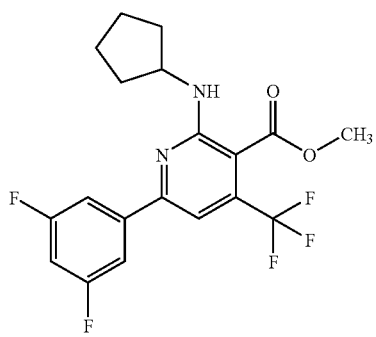

50 mg (0.142 mmol) of Example 46A, 18 mg (0.213 mmol) of cyclopentylamine and 37 mg (0.360 mmol) of triethylamine were stirred in 2 ml of THF at room temperature for 72 h. The reaction was checked, showing only incomplete conversion. Thus, another 12 mg (0.142 mmol) of cyclopentylamine and 29 mg (0.284 mmol) of triethylamine were added and the mixture was again stirred at 80° C. for 36 h. After removal of the volatile components on a rotary evaporator, the residue was purified by preparative HPLC (mobile phase: acetonitrile/water, gradient 10:90→90:10). This gave 56 mg (99% of theory) of the target compound.

LC-MS (method 1): $R_t$=3.55 min; MS (ESIpos): m/z=401 [M+H].

Example 48A

Methyl 2-chloro-6-(3,4-dichlorophenyl)-4-(trifluoromethyl)nicotinate

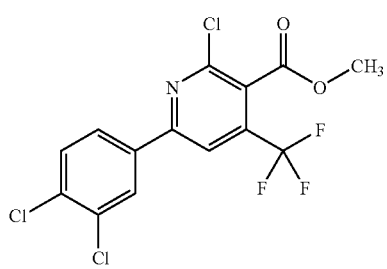

1.0 g (3.649 mmol) of Example 1A were initially charged in 11 ml of dioxane. Under argon, 0.70 g (3.649 mmol) of (3,4-dichlorophenyl)boronic acid and 10.9 ml (21.896 mmol) of a 2M aqueous potassium carbonate solution were added. The mixture was stirred at room temperature for 10 min. 0.26 g (0.365 mmol) of bis(triphenylphosphine)palladium(II) chloride and 0.11 mg (0.365 mmol) of tri-2-tolylphosphine were then added, and the reaction mixture was stirred at 60° C. for 1 h. After cooling, the volatile components were removed on a rotary evaporator. Ethyl acetate/water (1/1) was added to the residue, the aqueous phase was separated off and the organic phase was washed with saturated aqueous sodium bicarbonate solution. After washing with saturated aqueous sodium chloride solution, the organic phase was dried with sodium sulfate. The solvent was removed by distillation under reduced pressure. The residue was then subjected to column chromatography on silica gel (mobile phase: cyclohexane/ethyl acetate 40/1). This gave 1.12 g (67% of theory) of the target compound.

LC-MS (method 2): $R_t$=2.78 min; MS (ESIpos): m/z=386 [M+H]$^+$.

Example 49A

Methyl 2-chloro-6-(4-chloro-3-fluorophenyl)-4-(trifluoromethyl)nicotinate

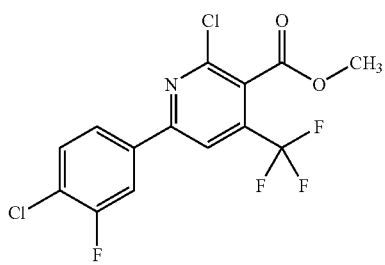

3.0 g (10.948 mmol) of Example 1A were initially charged in 32 ml of dioxane. Under argon, 1.90 g (10.948 mmol) of (4-chloro-3-fluorophenyl)boronic acid and 32.8 ml (65.687 mmol) of a 2M aqueous potassium carbonate solution were then added. The mixture was stirred for 10 min. 0.77 g (1.095 mmol) of bis(triphenylphosphine)palladium(II) chloride and 0.33 g (1.095 mmol) of tri-2-tolylphosphine were then added. The reaction mixture was then stirred at 60° C. for 2 h. After cooling, the volatile components were removed on a rotary evaporator. Ethyl acetate/water (1/1) was added to the residue, and the aqueous phase was separated off. The organic phase was washed with saturated aqueous sodium bicarbonate solution and with saturated aqueous sodium chloride solution. After drying over sodium sulfate, the solvent was removed on a rotary evaporator. The residue was then subjected to column chromatography on silica gel (mobile phase: cyclohexane/ethyl acetate 40/1). This gave 3.72 g (81% of theory) of the target compound.

LC-MS (method 1): $R_t$=3.07 min; MS (ESIpos): m/z=370 [M+H]$^+$.

Example 50A

Methyl 2-(diethylamino)-6-(3,5-difluorophenyl)-4-(trifluoromethyl)nicotinate

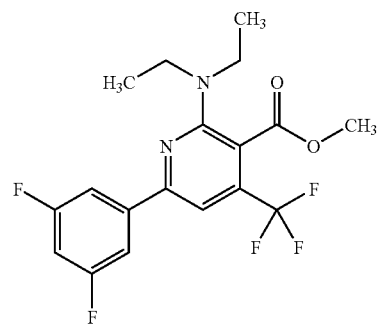

50 mg (0.142 mmol) of Example 46A, 16 mg (0.213 mmol) of diethylamine and 36 mg (0.355 mmol) of triethylamine were stirred in 2 ml of THF initially at 80° C. overnight and then at 60° C. for a further two days. However, when the reaction was checked only incomplete conversion was found. Thus, another 10 mg (0.142 mmol) of diethylamine and 29 mg (0.248 mmol) of triethylamine were added, and the mixture was again stirred at 80° C. for 36 h. After removal of the volatile components on a rotary evaporator, the crude product was purified by preparative HPLC (mobile phase: acetonitrile/water, gradient 10:90→90:10). This gave 21 mg (39% of theory) of the target compound.

LC-MS (method 7): $R_t$=3.10 min; MS (ESIpos): m/z=389 [M+H]$^+$.

Example 51A

Methyl 2-chloro-4-(trifluoromethyl)-6-[4-(trifluoromethyl)phenyl]nicotinate

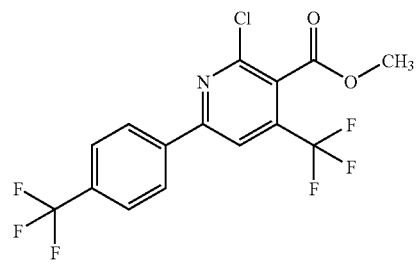

1.0 g (3.649 mmol) of Example 1A were initially charged in 11 ml of dioxane. Under argon, 0.693 g (3.649 mmol) of (4-trifluoromethylphenyl)boronic acid and 10.9 ml (21.896 mmol) of a 2M aqueous potassium carbonate solution were then added. The mixture was stirred for 10 min. 0.26 g (0.365 mmol) of bis(triphenylphosphine)palladium(II) chloride and 0.11 g (0.365 mmol) of tri-2-tolylphosphine were then added. The reaction mixture was then stirred at 60° C. for 1 h. After cooling, the reaction mixture was concentrated on a rotary evaporator. Ethyl acetate/water (1/1) was added to the residue, and the aqueous phase was separated off. The organic phase was then washed with saturated aqueous sodium bicarbonate solution and with saturated aqueous sodium chloride solution. After drying over sodium sulfate, the solvent was removed by distillation under reduced pressure and the crude product was subjected to column chromatography on silica gel (mobile phase: cyclohexane/ethyl acetate 40/1). This gave 1.46 g (78% of theory) of the target compound.

LC-MS (method 2): $R_t$=2.65 min; MS (ESIpos): m/z=384 [M+H]$^+$.

$^1$H-NMR (400 MHz, DMSO-d$_6$): δ [ppm]=3.99 (s, 3H), 7.91 (d, 2H), 8.44 (d, 2H), 8.62 (s, 1H).

Example 52A

Methyl 6-(4-chlorophenyl)-2-(3-methoxy-1-methyl-propoxy)-4-(trifluoromethyl)nicotinate

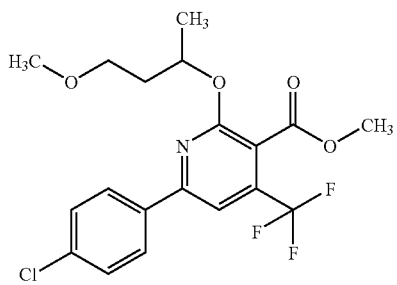

44 mg (0.440 mmol) of 4-methoxybutan-2-ol and 34 mg (0.857 mmol) of sodium hydride (60% strength dispersion in mineral oil) were initially charged in 5 ml of tetrahydrofuran. The reaction mixture was stirred at room temperature for 30 minutes. 100 mg (0.286 mol) of Example 24A were then added as a solution in 2 ml of tetrahydrofuran. The mixture was stirred at 80° C. overnight. The solvent was removed on a rotary evaporator and the mixture was purified by preparative HPLC (mobile phase: acetonitrile/water, gradient 10:90→90:10). This gave 37 mg (31% of theory) of the target compound.

LC-MS (method 1): $R_t$=3.23 min; MS (ESIpos): m/z=418 [M+H]$^+$.

$^1$H-NMR (400 MHz, CDCl$_3$): δ [ppm]=1.36 (d, 3H), 1:85-1.95 (m, 1H), 3.10 (s, 3H), 3.41 (t, 2H), 3.88 (s, 3H), 5.41-5.49 (m, 1H), 7.61 (d, 2H), 7.98 (s, 1H), 8.23 (d, 2H).

Example 53A

Benzyl 4-methyl-3-oxopentanoate

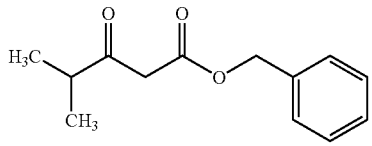

3 g of molecular sieve (4 Å) were activated in a microwave oven at 100 W for 5 min. The molecular sieve obtained in this manner was then initially charged, and 200 ml of anhydrous toluene were added. 4.9 g (30.97 mmol) of ethyl isobutyrylacetate and 4.02 g (37.2 mmol) of benzyl alcohol were then added. The reaction mixture was heated at reflux temperature for 6 h. After cooling, the molecular sieve was filtered off and the solvent was distilled off under reduced pressure. The residue was chromatographed on silica gel (mobile phase: cyclohexane/ethyl acetate 10/1). This gave 4.70 g (65% of theory) of the target compound.

LC-MS (method 2): $R_t$=1.87 min; MS (ESIpos): m/z=221 [M+H]$^+$.

$^1$H-NMR (400 MHz, DMSO-d$_6$): δ [ppm]=1.02 (d, 6H), 2.69 (sept, 1H), 3.74 (s, 2H), 5.13 (s, 2H), 7.30-7.41 (5H).

Example 54A

Ethyl 3-amino-3-(4-chlorophenyl)propanoate

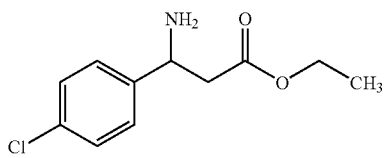

10 g (71.1 mmol) of 4-chlorobenzaldehyde, 9.40 g (71.1 mmol) of monoethyl malonate and 10.9 g (142.3 mmol) of ammonium acetate were taken up in 60 ml of ethanol, and the mixture was stirred at reflux temperature overnight. After cooling, 50 ml 1N hydrochloric acid were added to the residue and the mixture was washed with ethyl acetate. The aqueous phase was made basic with potassium carbonate and then extracted with dichloromethane (2×). The organic phase was dried with magnesium sulfate and the solvent was removed on a rotary evaporator. The residue was purified by preparative HPLC (mobile phase: acetonitrile/water, gradient 10:90→90:10). This gave 1.80 g (11% of theory) of the target compound.

MS (EIpos): m/z=228 [M+H]$^+$

LC-MS (method 6): $R_t$=0.66 min

Example 55A

Benzyl 3-{[1-(4-chlorophenyl)-3-ethoxy-3-oxopropyl]amino}-4-methylpent-2-enoate

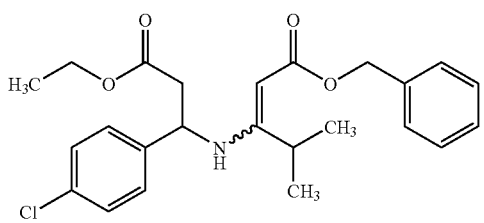

1.80 g (7.91 mmol) of Example 54A, 1.92 g (8.70 mmol) of Example 53A and 0.905 ml (15.8 mmol) of acetic acid were taken up in 30 ml of benzene and stirred at reflux on a water separator overnight. After cooling, the mixture was washed with saturated aqueous sodium bicarbonate solution, the aqueous phase was dried with magnesium sulfate and the solvent was distilled off under reduced pressure. The residue was purified by preparative MPLC (Biotage 40M cartridge; mobile phase: isohexane/ethyl acetate 9/1). This gave 2.06 g (52% of theory) of the target compound.

LC-MS (method 1): R$_t$=3.20 min; MS (ESIpos): m/z=430 [M+H]$^+$.

Example 56A

Benzyl 6-(4-chlorophenyl)-2-(1-methylethyl)-4-oxo-1,4,5,6-tetrahydropyridine-3-carboxylate

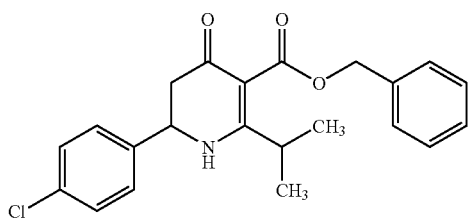

2.00 g (4.65 mmol) of Example 55A were taken up in 15 ml tert-butanol, and 0.626 g (5.58 mmol) of potassium tort-butoxide was added a little at a time. The mixture was stirred at room temperature for 1 h and then cooled in an ice-bath. The mixture was acidified with 15 ml 1N hydrochloric acid and then diluted with 20 ml of water. The mixture was then extracted with chloroform (3×). The organic phases were combined and dried with magnesium sulfate, and the solvent was removed on a rotary evaporator. The residue was purified by preparative MPLC (Biotage 40M cartridge; mobile phase: isohexane/ethyl acetate 9/1). This gave 0.90 g (50% of theory) of the target compound.

LC-MS (method 1): R$_t$=2.42 min; MS (ESIpos): m/z=384 [M+H]$^+$.

$^1$H-NMR (400 MHz, DMSO-d$_6$): δ [ppm]=1.15 (d, 3H), 1.19 (d, 3H), 2.66 (dd, 1H), 3.07 (sept, 1H), 4.82 (dt, 1H), 5.09 (d, 1H), 5.12 (d, 1H), 7.29 (m, 1H), 7.33-7.38 (m, 4H), 7.41 (d, 2H), 7.44 (d, 2H), 8.30 (d, 1H).

Example 57A

Benzyl 6-(4-chlorophenyl)-2-(1-methylethyl)-4-oxo-1,4-dihydropyridine-3-carboxylate

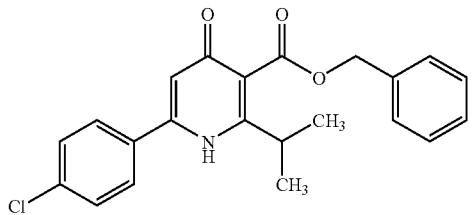

276 mg (0.719 mmol) of Example 56A and 228 mg (1.007 mmol) of DDQ were taken up in 15 ml of benzene and stirred at room temperature for 2 h. The volatile components were removed on a rotary evaporator and the residue was suspended in a little acetonitrile. The residue was isolated by filtration and again taken up in a little acetonitrile. The residue was suspended finely in an ultrasonic bath and again purified by filtration. Drying under high vacuum then gave 264 mg (96% of theory) of the target compound as a solid.

LC-MS (method 1): R$_t$=2.75 min; MS (ESIpos): m/z=382 [M+H]$^+$.

$^1$H-NMR (400 MHz, DMSO-d$_6$): δ [ppm]=1.18 (d, 6H), 2.93 (sept, 1H), 5.35 (s, 2H), 7.19 (s, 1H), 7.32-7.49 (m, 5H), 7.56 (d, 2H), 8.00 (d, 2H), 11.27 (s, 1H).

Example 58A

Benzyl 6-(4-chlorophenyl)-4-(1-methylethoxy)-2-(1-methylethyl)nicotinate

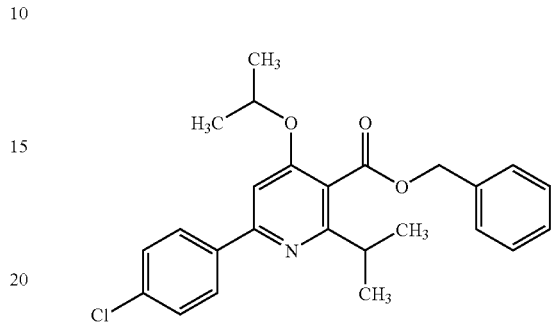

90 mg (0.236 mmol) of Example 57A, 19 µl (0.247 mmol) of 2-propanol and 64.9 mg (0.247 mmol) of triphenylphosphine were initially charged in 3 ml of THF. After 20 min, 4.8 µl (0.247 mmol) of DIAD were added dropwise. The reaction mixture was then reacted at room temperature overnight. The volatile components were removed on a rotary evaporator. The residue was purified by preparative HPLC (mobile phase: acetonitrile/water, gradient 10:90→90:10). This gave 67 mg (67% of theory) of the target compound.

LC-MS (method 6): R$_t$=1.83 min; MS (ESIpos): m/z=424 [M+H]$^+$.

$^1$H-NMR (400 MHz, DMSO-d$_6$): δ [ppm]=1.21 (d, 6H), 1.23 (d, 6H), 2.91 (sept, 1H), 5.01 (sept, 1H), 5.36 (s, 2H), 7.33-7.48 (m, 5H), 7.52 (s, 1H), 7.56 (d, 2H), 8.18 (d, 2H).

Example 59A

Methyl 2-chloro-4-(trifluoromethyl)-6-(4-bromophenyl)nicotinate

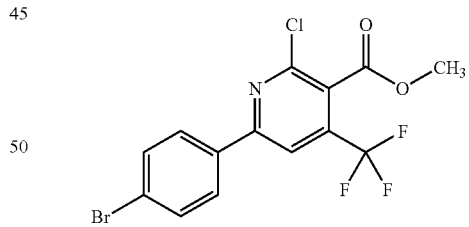

1.0 g (3.649 mmol) of Example 1A were initially charged in 10 ml of dioxane. Under Argon, 0.733 g (3.649 mmol) of 4-bromophenylboronic acid and 10.9 ml (21.896 mmol) of a 2M aqueous potassium carbonate solution were then added. The mixture was stirred for 10 min. 0.26 g (0.365 mmol) of bis(triphenylphosphine)palladium(II) chloride and 0.11 g (0.365 mmol) of tri-2-tolylphosphine were then added, and the reaction mixture was stirred at 60° C. overnight. After cooling, the volatile components were removed on a rotary evaporator. Ethyl acetate/water (1/1) was added to the residue that remained, and the aqueous phase was separated off. The organic phase was washed with saturated aqueous sodium bicarbonate solution and with saturated aqueous sodium chloride solution. After drying over sodium sulfate, the solvent was removed by distillation under reduced pressure. The residue was then subjected to column chromatography on silica gel (mobile phase: cyclohexane/ethyl acetate 40/1). Further work-up was then carried out by preparative HPLC (mobile phase: acetonitrile/water, gradient 10:90→90:10). This gave 271 mg (19% of theory) of the target compound.

LC-MS (method 6): $R_t$=1.59 min; MS (ESIpos): m/z=395 [M+H]$^+$.

$^1$H-NMR (400 MHz, DMSO-d$_6$): δ [ppm]=3.97 (s, 3H), 7.78 (d, 2H), 8.18 (d, 2H), 8.53 (s, 1H).

Example 60A

Ethyl 3-{[1-(4-chlorophenyl)-3-methoxy-3-oxopropyl]amino}-4,4,4-fluorobut-2-enoate

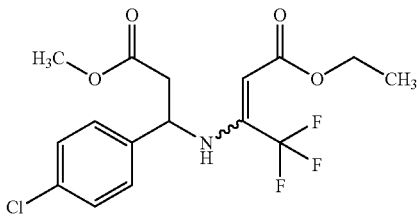

9.17 g (42.9 mmol) of methyl-3-amino-3-(4-chlorophenyl)propanoate [obtainable by release from the hydrochloride, see M. Y. Ashton et al., *Heterocycles* 28, 1015-1035 (1989)], 6.90 ml (47.2 mmol) of ethyl-4,4,4-trifluoro-3-oxobutanoate and 5.04 ml (88.0 mmol) of acetic acid were taken up in 200 ml of benzene and stirred at reflux on a water separator overnight. After cooling, the mixture was washed with saturated aqueous sodium bicarbonate solution, the organic phase was dried with magnesium sulfate and the solvent was distilled off under reduced pressure. This gave 14.89 g (82% of theory) of the target compound in a purity of 90%. Without any further purification, this was used for the subsequent reactions.

LC-MS (method 6): $R_t$=1.54 min; MS (ESIpos): m/z=380 [M+H]$^+$.

Example 61A

Ethyl 6-(4-chlorophenyl)-4-oxo-2-(trifluoromethyl)-1,4,5,6-tetrahydropyridine-3-carboxylate

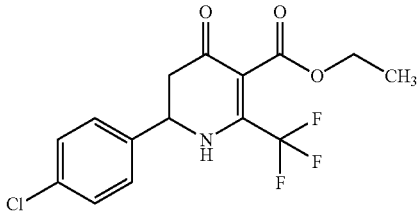

14.60 g (34.6 mmol) of Example 60A were taken up in 100 ml tert-butanol, and 4.66 g (41.5 mmol) of potassium tert-butoxide were added a little at a time. The mixture was stirred at room temperature for 2 h and then cooled in an ice-bath. The mixture was acidified with 120 ml 1N hydrochloric acid and then diluted with 20 ml of water. The mixture was then extracted with chloroform (3×). The organic phases were combined and dried with magnesium sulfate, and the solvent was removed on a rotary evaporator. The residue was purified by column chromatography (silica gel, mobile phase: cyclohexane/ethyl acetate=10/1−>5/1). This gave 11.39 g (~70% of theory) of a fraction which contained the target compound in a purity of 70-80%. Without any further purification steps, this fraction was used for the subsequent reactions.

LC-MS (method 2): $R_t$=1.82 min; MS (ESIpos): m/z=348 [M+H]$^+$.

Example 62A

Ethyl 6-(4-chlorophenyl)-4-oxo-2-(trifluoromethyl)-1,4-dihydropyridine-3-carboxylate

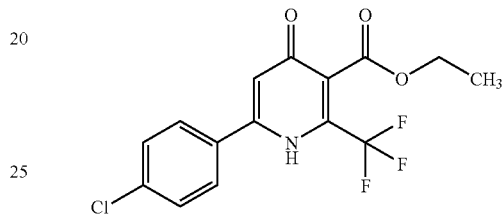

6.41 g (18.43 mmol) of Example 61A and 5.89 g (25.81 mmol) of DDQ were taken up in 230 ml of benzene and stirred at room temperature overnight. The volatile components were removed on a rotary evaporator and the residue was suspended in acetonitrile. The residue was isolated by filtration and again taken up in a little acetonitrile. The residue was suspended finely in an ultrasonic bath and again purified by filtration. Drying under high vacuum then gave 3.86 g (96% of theory) of the target compound.

LC-MS (method 1): $R_t$=2.81 min; MS (ESIpos): m/z=346 [M+H]$^+$.

$^1$H-NMR (400 MHz, DMSO-d$_6$): δ [ppm]=1.29 (t, 3H), 4.34 (q, 2H), 7.58 (s, 1H), 7.62 (d, 2H), 8.02 (d, 2H), 12.30 (s, 1H).

Example 63A

Ethyl 4-chloro-6-(4-chlorophenyl)-2-(trifluoromethyl)nicotinate

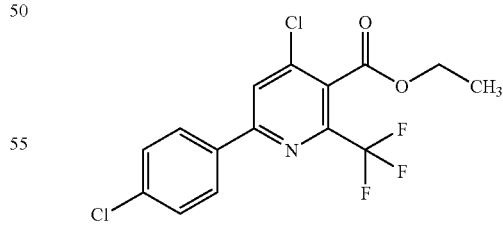

400 mg (1.16 mmol) of Example 62A were initially charged in 0.5 ml of DMF. The mixture was cooled in an ice-bath, and 2.0 ml of phosphorus oxychloride were then added dropwise. The mixture was then stirred at reflux temperature for 3 h. After cooling, the volatile components were removed on a rotary evaporator and the residue was taken up in dichloromethane. The mixture was washed with water and 2N aqueous sodium carbonate solution. After drying with magnesium sulfate, the solvent was removed on a rotary evaporator and purified by column chromatography on silica gel using dichloromethane. This gave 419 mg (99% of theory) of the target compound.

LC-MS (method 2): $R_t$=2.74 min; MS (ESIpos): m/z=364 [M]+.

$^1$H-NMR (400 MHz, DMSO-$d_6$): δ [ppm]=1.34 (t, 3H), 4.46 (q, 2H), 7.65 (d, 2H), 8.23 (d, 2H), 8.71 (s, 1H).

Example 64A

Ethyl 6-(4-chlorophenyl)-4-[(1-methylethyl)amino]-2-(trifluoromethyl)nicotinate

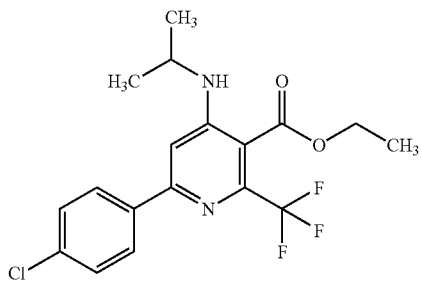

117 mg (0.321 mmol) of Example 63A and 112 μl (0.803 mmol) of triethylamine were initially charged in 3 ml of THF, 109 μl (0.803 mmol) of isopropylamine were added and the mixture was reacted at 40° C. for 12 h. TLC showed incomplete conversion. Thus, the mixture was heated at 70° C. for another 24 h. The mixture was then suspended in water, extracted with ethyl acetate and dried with magnesium sulfate, and the solvent was removed on a rotary evaporator. The crude product was then purified by preparative HPLC (mobile phase: acetonitrile/water, gradient 10:90→90:10). This gave 56 mg (45% of theory) of the target compound.

LC-MS (method 1): $R_t$=3.33 min; MS (ESIpos): m/z=387 [M+H]+.

$^1$H-NMR (400 MHz, DMSO-$d_6$): δ [ppm]=1.22 (d, 6H), 1.29 (t, 3H), 4.10 (mz, 4.35 (q, 2H), 6.43 (d, 1H), 7.39 (s, 1H), 7.58 (d, 2H), 8.15 (d, 2H).

Example 65A

Methyl 3-{[1-(4-chlorophenyl)-3-ethoxy-3-oxopropyl]amino}-4-methylpent-2-enoate

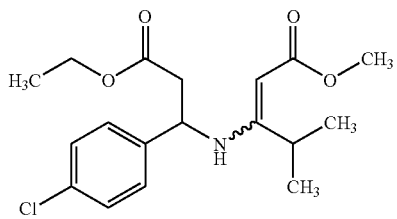

5.70 g (25.0 mmol) of ethyl-3-amino-3-(4-chlorophenyl)propanoate [V. Wehner et al., Synthesis 14, 2023-2036 (2002)], 3.993 ml (27.5 mmol) of methyl 4-methyl-3-oxopentanoate and 2.87 ml (50.1 mmol) of acetic acid were taken up in 70 ml of benzene and reacted at reflux on a water separator overnight. After cooling, the mixture was washed with saturated aqueous sodium bicarbonate solution, the organic phase was dried with magnesium sulfate and the solvent was destilled off under reduced pressure. This gave 8.57 g (68% of theory) of the target compound in a purity of 70%. The fraction was used without further work-up for the subsequent steps.

LC-MS (method 6): $R_t$=1.48 min; MS (ESIpos): m/z=354 [M+H]+.

Example 66A

Methyl 6-(4-chlorophenyl)-2-(1-methylethyl)-4-oxo-1,4,5,6-tetrahydropyridine-3-carboxylate

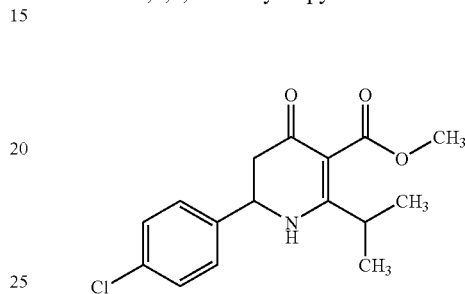

8.57 g (24.2 mmol) of Example 65A were taken up in 90 ml of tert-butanol, and 3.26 g (29.1 mmol) of potassium tert-butoxide were added a little at a time. The mixture was stirred at room temperature for 2 h and then cooled in an ice-bath. The mixture was hydrolyzed with 50 ml of water and acidified with 50 ml of 1N hydrochloric acid. The mixture was then extracted with chloroform (3×). The organic phases were combined and dried with magnesium sulfate, and the solvent was removed on a rotary evaporator. This gave 7.07 g (87% of theory) of the target compound in a purity of 93% (LC-MS).

LC-MS (method 6): $R_t$=0.99 min; MS (ESIpos): m/z=38 [M+H]+.

Example 67A

Methyl 6-(4-chlorophenyl)-2-(1-methylethyl)-4-oxo-1,4-dihydropyridine-3-carboxylate

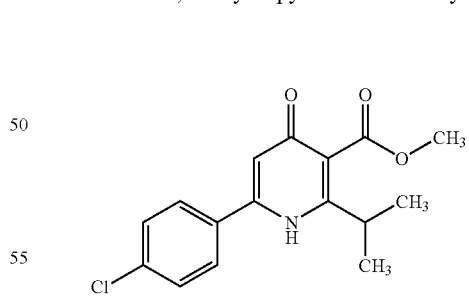

7.07 g (22.97 mmol) of Example 66A and 7.30 g (32.16 mmol) of DDQ were taken up in 150 ml of benzene and stirred at room temperature overnight. The volatile components were removed on a rotary evaporator. The residue was purified by preparative MPLC (Biotage 40M cartridge; mobile phase: isohexane/ethyl acetate 4/1). This gave 2.15 g (23% of theory) of the target compound in a purity of 90%.

LC-MS (method 1): $R_t$=2.19 min; MS (ESIpos): m/z=306 [M+H]+.

$^1$H-NMR (400 MHz, DMSO-$d_6$): δ [ppm]=1.24 (d, 6H), 2.97 (sept, 1H), 3.84 (s, 3H), 7.21 (s, 1H), 7.56 (d, 2H), 8.02 (d, 2H), 11.21 (s, 1H).

Example 68A

Methyl 6-(4-chlorophenyl)-4-ethoxy-2-(1-methylethyl)nicotinate

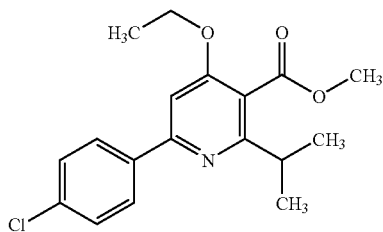

1.90 g (6.21 mmol) of Example 67A, 380 µl (6.53 mmol) of ethanol and 1.71 g (6.53 mmol) of triphenylphosphine were initially charged in 80 ml of THF. After 20 mitt, 1.26 ml (6.53 mmol) of DIAD were added dropwise. The reaction mixture was then reacted at room temperature overnight. The volatile components were then removed on a rotary evaporator. The residue was purified by preparative MPLC (Biotage 40M cartridge; mobile phase: isohexane/ethyl acetate 4/1). This gave 1.77 g (85% of theory) of the target compound.

LC-MS (method 6): $R_t$=1.83 min; MS (ESIpos): m/z=424 [M+H]$^+$.

$^1$H-NMR (400 MHz, DMSO-$d_6$): δ [ppm]=1.24 (d, 6H), 1.32 (t, 3H), 2.93 (sept, 1H), 3.85 (s, 3H), 4.29 (q, 2H), 7.51 (s, 1H), 7.57 (d, 2H), 8.20 (d, 2H).

Example 69A

Methyl 6-(4-chlorophenyl)-2-(1-methylethyl)-4-(trifluoromethyl)nicotinate

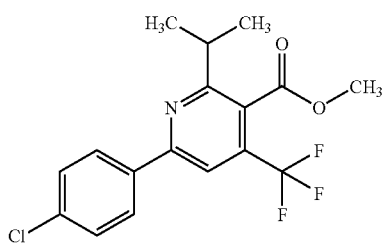

150 mg (0.599 mmol) of 1-(4-chlorophenyl)-4,4,4-trifluorobutane-1,3-dione [Katsuyama et al., *Synthesis*, 1321-1324 (1997)] and 171 mg (1.20 mmol) of methyl 3-amino-4-methylpent-2-enoate [Holz et al., *J. Org. Chem.* 68., 1701-1707 (2003)] in 2 ml of acetonitrile were reacted at reflux temperature overnight. The volatile components were then removed on a rotary evaporator. The residue was purified by preparative HPLC (mobile phase: acetonitrile/water, gradient 10:90→90:10). This gave 34 mg (16% of theory) of the target compound.

LC-MS (method 6): $R_t$=1.73 min; MS (ESIpos): m/z=358 [M+H]$^+$.

$^1$H-NMR (400 MHz, DMSO-$d_6$): δ [ppm]=1.31 (d, 6H), 3.11 (sept, 1H), 3.95 (s, 3H), 7.63 (d, 2H), 8.27 (s, 1H), 8.30 (d, 2H).

Example 70A

Methyl 6-(4-chlorophenyl)-2-ethyl-4-oxo-1,4-dihydropyridine-3-carboxylate

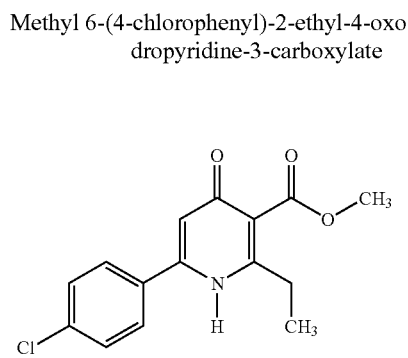

2.00 g (8.82 mmol) of ethyl 3-(4-chlorophenyl)-3-oxopropanoate and 1.25 g (9.71 mmol) of methyl 3-aminopent-2-enoate [Pena et al., *J. Am. Chem. Soc.* 124, 14552-14553 (2002)] were taken up in 12 ml of xylene, 3.50 g molecular sieve (4 Å) which had been dried by heating were added and the mixture was reacted at reflux temperature overnight. The molecular sieve was removed by filtration and washed with methanol/chloroform (1/1). The combined organic phases were concentrated on a rotary evaporator and the crude product was purified by preparative MPLC (Biotage 40M cartridge; mobile phase: isohexane/ethyl acetate 4/1). This gave 550 mg (21% of theory) of the target compound.

LC-MS (method 6): $R_t$=0.91 min; MS (ESIpos): m/z=292 [M+H]$^+$.

Example 71A

Methyl 6-(4-chlorophenyl)-4-ethoxy-2-ethylnicotinate

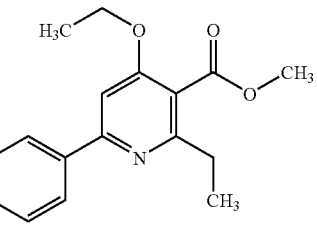

180 mg (0.617 mmol) of Example 70A, 38 µl (0.648 mmol) of ethanol and 170 mg (0.648 mmol) of triphenylphosphine were initially charged in 10 ml of THF. After 20 min, 125 µl (0.648 mmol) of DIAD were added dropwise. The reaction mixture was then reacted at room temperature overnight. Work-up was carried out by preparative HPLC (mobile phase: acetonitrile/water, gradient 10:90→90:10). This gave 78 mg (38% of theory) of the target compound.

LC-MS (method 2): $R_t$=2.41 min; MS (ESIpos): m/z=320 [M+H]$^+$.

¹H-NMR (400 MHz, DMSO-d₆): δ [ppm]=1.23 (t, 3H), 1.32 (t, 3H), 2.67 (q, 2H), 3.85 (s, 3H), 4.30 (q, 2H), 7.53 (s, 1H), 7.57 (d, 2H), 8.19 (d, 2H).

Example 72A

Methyl 6-(4-chlorophenyl)-2-ethyl-4-(1-methylethoxy)nicotinate

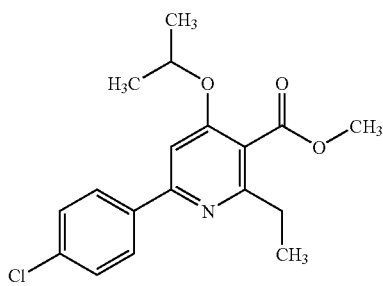

180 mg (0.617 mmol) of Example 70A, 50 µl (0.648 mmol) of isopropanol and 170 mg (0.648 mmol) of triphenylphosphine were initially charged in 10 ml of THF. After 20 min, 125 µl (0.648 mmol) of DIAD were added dropwise. The reaction mixture was then reacted at room temperature overnight. Work-up was carried out by preparative HPLC (mobile phase: acetonitrile/water, gradient 10:90→90:10). This gave 80 mg (39% of theory) of the target compound.

LC-MS (method 2): $R_t$=2.52 min; MS (ESIpos): m/z=334 [M+H]⁺.

¹H-NMR (400 MHz, DMSO-d₆): δ [ppm]=1.23 (t, 3H), 1.29 (d, 6H), 2.66 (q, 2H), 3.84 (s, 3H), 5.02 (sept, 1H), 7.54 (s, 1H), 7.56 (d, 2H), 8.18 (d, 2H).

Example 73A

Methyl 2-ethyl-4-oxo-6-[4-(trifluoromethyl)phenyl]-1,4-dihydropyridine-3-carboxylate

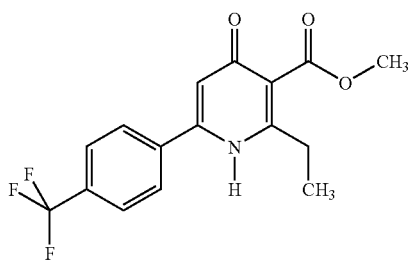

1.00 g (3.84 mmol) of methyl 3-oxo-3-[4-(trifluoromethyl)phenyl]propanoate and 546 mg (4.23 mmol) of methyl 3-aminopent-2-enoate [Pena et al., *J. Am. Chem. Soc.* 124., 14552-14553 (2002)] were taken up in 4 ml of xylene, 1.50 g molecular sieve (4 Å) which had been dried by heating were added and the mixture was reacted at reflux temperature overnight. The molecular sieve was removed by filtration and washed with methanol/chloroform (1/1). The combined organic phases were concentrated on a rotary evaporator and the crude product was purified by preparative HPLC (mobile phase: acetonitrile/water, gradient 10:90→90:10). This gave 270 mg (21% of theory) of the target compound.

LC-MS (method 2): $R_t$=1.55 min; MS (ESIpos): m/z=326 [M+H]⁺.

Example 74A

Methyl 2-ethyl-4-(1-methylethoxy)-6-[4-(trifluoromethyl)phenyl]nicotinate

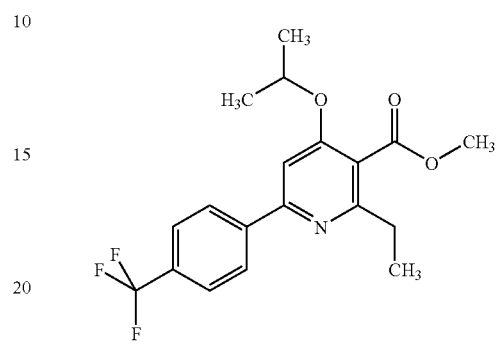

180 mg (0.553 mmol) of Example 73A, 44 µl (0.581 mmol) of 2-propanol and 152 mg (0.581 mmol) of triphenylphosphine were initially charged in 10 ml of THF. After 20 min, 112 µl (0.581 mmol) of DIAD were added dropwise. The reaction mixture was then reacted at room temperature overnight. However, TLC showed incomplete conversion. Thus, another 44 µl (0.581 mmol) of 2-propanol, 152 mg (0.581 mmol) of triphenylphosphine and 112 µl (0.581 mmol) of DIAD were metered in. After 90 min, the reaction mixture was then purified directly by preparative HPLC (mobile phase: acetonitrile/water, gradient 10:90→90:10). This gave 152 mg (70% of theory) of the target compound.

LC-MS (method 6): $R_t$=1.57 min; MS (ESIpos): m/z=368 [M+H]⁺.

¹H-NMR (400 MHz, DMSO-d₆): δ [ppm]=1.24 (t, 3H), 1.29 (d, 6H), 2.68 (q, 2H), 3.85 (s, 3H), 5.05 (sept, 1H), 7.63 (s, 1H), 7.86 (d, 2H), 8.36 (d, 2H).

Example 75A

Methyl 2-ethyl-4-(3-methylbutoxy)-6-[4-(trifluoromethyl)phenyl]nicotinate

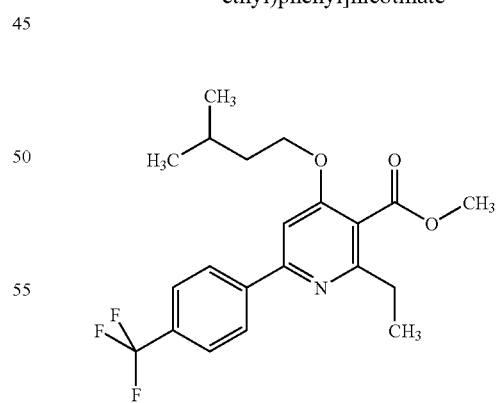

90 mg (0.277 mmol) of Example 73A, 32 µl (0.291 mmol) of 3-methylbutan-1-ol and 76 mg (0.291 mmol) of triphenylphosphine were initially charged in 5 ml of THF. After 20 min, 56 µl (0.291 mmol) of DIAD were added dropwise. The reaction mixture was then reacted at room temperature over a period of 72 h. However, TLC showed incomplete conversion. Thus, another 32 µl (0.291 mmol) of 3-methylbutan-1- ol, 76 mg (0.291 mmol) of triphenylphosphine and 56 µl (0.291 mmol) of DIAD were metered in. After 90 min, the reaction mixture was then purified directly by preparative HPLC (mobile phase: acetonitrile/water, gradient 10:90→90:10). This gave 60 mg (53% of theory) of the target compound.

LC-MS (method 6): $R_t$=1.73 min; MS (ESIpos): m/z=396 [M+H]$^+$.

$^1$H-NMR (400 MHz, DMSO-d$_6$): δ [ppm]=0.94 (d, 6H), 1.25 (t, 3H), 1.62 (mz, 2H), 1.76 (sept, 1H), 2.70 (q, 2H), 3.84 (s, 3H), 4.28 (t, 2H), 7.64 (s, 1H), 7.87 (d, 2H), 8.37 (d, 2H).

WORKING EXAMPLES

Example 1

6-(3-Fluoro-4-methylphenyl)-2-isobutyl-4-(trifluoromethyl)nicotinic acid

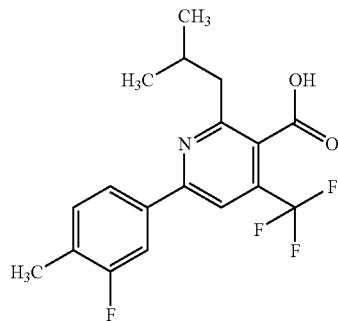

2.92 g (7.91 mmol) of Example 3A were taken up in 50 ml of isopropanol, and 2.21 g (39.5 mmol) of potassium hydroxide were added. The mixture was then stirred at reflux temperature for three days. After cooling, the volatile components were removed by distillation under reduced pressure. The residue was taken up in water and the resulting mixture was acidified with 1N hydrochloric acid. The precipitated product was removed by filtration and then washed with water and with n-pentane. Drying under high vacuum gave 2.39 g (81% of theory) of the target compound.

LC-MS (method 1): $R_t$=3.24 min; MS (ESIpos): m/z=356 [M+H]$^+$.

$^1$H-NMR (400 MHz, DMSO-d$_6$): δ [ppm]=0.93 (d, 6H), 2.23-2.35 (m, 4H), 2.77 (d, 2H), 7.45 (t, 1H), 7.95-8.04 (m, 2H), 14.17 (s, 1H).

Example 2

6-(3-Fluoro-4-methylphenyl)-2-isobutyl-4-(trifluoromethyl)nicotinic acid sodium salt

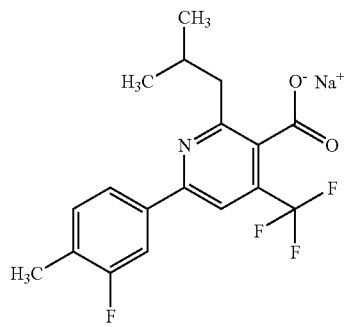

2.15 g (5.81 mmol) of Example 1 were taken up in 20 ml of ethanol, and 5.81 ml (5.81 mmol) of a 1M aqueous sodium hydroxide solution were added. After one hour of stirring at room temperature, the reaction mixture was filtered, the filtrate was concentrated and the residue was dried under high vacuum. This gave 2.17 g (95% of theory) of the target compound.

$^1$H-NMR (400 MHz, DMSO-d$_6$): δ [ppm]=0.91 (d, 6H), 2.28 (s, 3H), 2.35 (mz, 1H), 2.75 (d, 2H), 7.39 (t, 1H), 7.81-7.90 (m, 3H).

Example 3

6-(3-Fluoro-4-methylphenyl)-2-isopropoxy-4-(trifluoromethyl)nicotinic acid

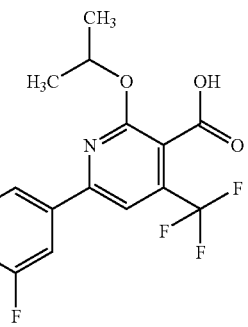

150 mg (0.431 mmol) of Example 4A were taken up in 5 ml of isopropanol, and 1.29 ml (1.29 mmol) of a 1M aqueous sodium hydroxide solution were added. The mixture was then stirred at reflux temperature overnight. After cooling, the volatile components were removed by distillation under reduced pressure. The residue was taken up in water and the resulting mixture was acidified with 1N hydrochloric acid. The mixture was extracted with ethyl acetate, the extract was dried with magnesium sulfate and the volatile components were removed on a rotary evaporator. The crude product was purified by preparative HPLC (mobile phase: acetonitrile/water with 0.1% formic acid, gradient 20:80→95:5). Drying under high vacuum gave 70 mg (45% of theory) of the target compound.

LC-MS (method 1): $R_t$=3.05 min; MS (ESIpos): m/z=358 [M+H]$^+$.

$^1$H-NMR (400 MHz, DMSO-d$_6$): δ [ppm]=1.37 (d, 6H), 2.31 (s, 3H), 5.48 (sept, 1H), 7.45 (t, 1H), 7.89-8.00 (m, 3H), 13.80 (s, 1H).

Example 4

6-(3-Fluoro-4-methylphenyl)-4-isobutyl-2-methylnicotinic acid

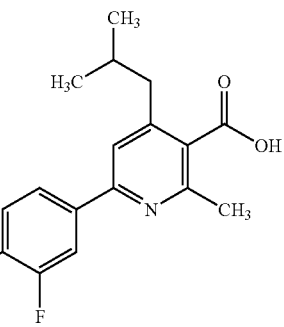

70 mg (5.81 mmol) of Example 7A were taken up in 5 ml of methanol, and 0.637 ml (0.637 mmol) of a 1M aqueous sodium hydroxide solution was added. The mixture was then reacted in a closed vessel at 70° C. overnight. The mixture was concentrated, taken up in 10 ml of water and acidified with 1N hydrochloric acid, and the precipitated product was isolated. Final purification was carried out by preparative HPLC (mobile phase: acetonitrile/water with 0.1% formic acid, gradient 20:80→95:5). Drying under high vacuum gave 47 mg (45% of theory) of the target compound.

LC-MS (method 1): $R_t$=2.24 min; MS (ESIpos): m/z=302 [M+H]$^+$.

$^1$H-NMR (400 MHz, DMSO-d$_6$): δ [ppm]=0.88 (d, 6H), 1.99 (sept, 1H), 2.30 (s, 3H), 2.56 (s, 3H), 2.59 (d, 2H), 7.42 (t, 1H), 7.77 (s, 1H), 7.82-7.91 (m, 2H).

Example 5

6-(3,5-Difluorophenyl)-4-isobutyl-2-methylnicotinic acid

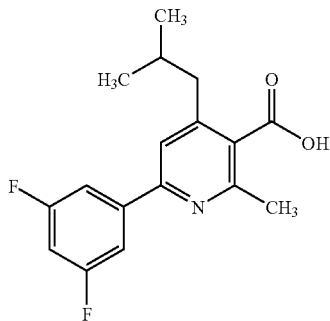

90 mg (0.270 mmol) of Example 8A were taken up in 4 ml of methanol, and 0.810 ml (0.810 mmol) of a 1M aqueous sodium hydroxide solution were added. The mixture was then reacted in a single mode microwave (Emrys Optimizer) at 140° C. for 45 min. The mixture was concentrated, taken up in 10 ml of water and acidified with 1N hydrochloric acid, and the precipitated product was isolated. Drying under high vacuum gave 56 mg (65% of theory) of the target compound.

LC-MS (method 4): $R_t$=2.17 min; MS (ESIpos): m/z=306 [M+H]$^+$.

$^1$H-NMR (400 MHz, DMSO-d$_6$): δ [ppm]=0.88 (d, 6H), 2.01 (sept, 1H), 2.57 (d, 2H), 7.33 (tt, 1H), 7.81-7.91 (m, 3H), 13.60 (s, 1H).

Example 6

6-(3-fluorophenyl)-4-isobutyl-2-methylnicotinic acid

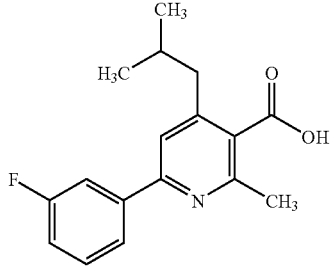

64 mg (0.203 mmol) of Example 9A were taken up in 3 ml of methanol, and 0.609 ml (0.609 mmol) of a 1M aqueous sodium hydroxide solution was added. The mixture was then reacted in a single mode microwave (Emrys Optimizer) at 140° C. for 45 min. The mixture was concentrated, taken up in 10 ml of water and acidified with 1N hydrochloric acid, and the precipitated product was isolated. Drying under high vacuum gave 38 mg (65% of theory) of the target compound.

LC-MS (method 2): $R_t$=1.55 min; MS (ESIpos): m/z=288 [M+H]$^+$.

$^1$H-NMR (400 MHz, DMSO-d$_6$): δ [ppm]=0.88 (d, 6H), 1.99 (sept, 1H), 2.54 (s, 3H), 2.58 (d, 2H), 7.27 (dt, 1H), 7.54 (q, 1H), 7.76 (s, 1H), 7.91 (mz, 1H), 7.96 (d, 1H), 13.49 (s, 1H).

Example 7

6-(3-Fluoro-4-methylphenyl)-2-(isopropylamino)-4-(trifluoromethyl)nicotinic acid

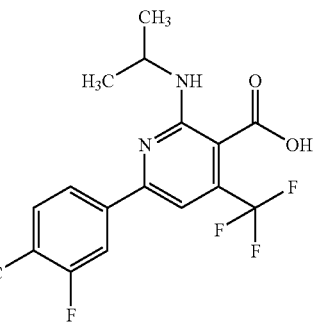

95 mg (0.257 mmol) of Example 10A were taken up in 4 ml of methanol, and 0.770 ml (0.770 mmol) of a 1M aqueous sodium hydroxide solution was added. The mixture was then reacted at 70° C. in a closed vessel overnight. The mixture was concentrated, taken up in 10 ml of water and acidified with 1N hydrochloric acid, and the precipitated product was isolated. Drying under high vacuum gave 63 mg (69% of theory) of the target compound.

LC-MS (method 4): $R_t$=2.79 min; MS (ESIpos): m/z=357 [M+H]$^+$.

$^1$H-NMR (400 MHz, DMSO-d$_6$): δ [ppm]=1.25 (d, 6H), 2.30 (s, 3H), 4.36 (mz, 1H), 6.78 (sbr, 1H), 7.38-7.47 (m, 2H), 7.90 (mz, 1H), 7.92 (s, 1H), 13.92 (sbr, 1H).

Example 8

6-(3-Fluoro-4-methylphenyl)-2-[isopropyl(methyl)amino]-4-(trifluoromethyl)nicotinic acid

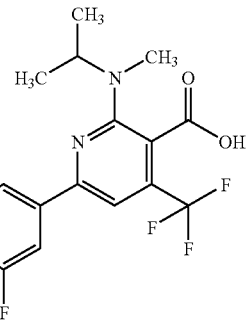

96 mg (0.250 mmol) of Example 11A were taken up in 4 ml of methanol, and 0.749 ml (0.749 mmol) of a 1M aqueous sodium hydroxide solution was added. The mixture was then reacted in a single mode microwave (Emrys Optimizer) at 120° C. for one hour. The mixture was concentrated, taken up in 10 ml of water and acidified with 1N hydrochloric acid. The water was distilled off under reduced pressure. Final work-up was then carried out by preparative HPLC (mobile phase: acetonitrile/water with 0.1% formic acid, gradient 20:80→95:5). Drying under high vacuum gave 16 mg (17% of theory) of the target compound.

LC-MS (method 4): $R_t$=2.64 min; MS (ESIpos): m/z=371 [M+H]⁺.

¹H-NMR (400 MHz, DMSO-d₆): δ [ppm]=1.20 (d, 6H), 2.30 (s, 3H), 2.87 (s, 3H), 4.64 (sept, 1H), 7.42 (t, 1H), 7.53 (s, 1H), 7.86-7.94 (m, 2H), 13.77 (s, 1H).

Example 9

2-Ethyl-6-(3-fluoro-4-methylphenyl)-4-isobutylnicotinic acid

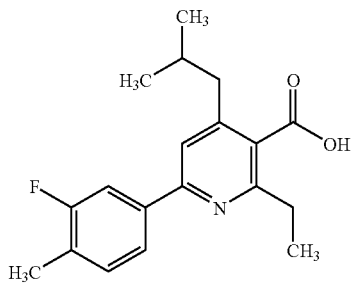

137 mg (0.416 mmol) of Example 14A were taken up in 8 ml of 2-propanol, and 2.00 ml (4.000 mmol) of a 2M aqueous potassium hydroxide solution were added. The mixture was then reacted in a single mode microwave (Emrys Optimizer) at 180° C. for 2 h. The mixture was concentrated, taken up in 10 ml of water and acidified with 2N hydrochloric acid. The mixture was extracted with ethyl acetate (3×20 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 77 mg (58% of theory) of the target compound.

LC-MS (method 1): $R_t$=2.69 min; MS (ESIpos): m/z=316 [M+H]⁺.

¹H-NMR (400 MHz, DMSO-d₆): δ [ppm]=0.88 (d, 6H), 1.28 (t, 3H), 1.99 (sept, 1H), 2.30 (s, 3H), 2.56 (d, 2H), 2.82 (q, 2H), 7.41 (t, 1H), 7.74 (s, 1H), 7.85-7.92 (m, 2H).

Example 10

2-Ethyl-6-(3-fluorophenyl)-4-isobutylnicotinic acid

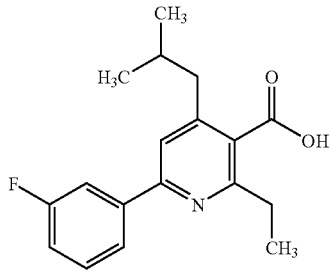

56 mg (0.178 mmol) of Example 15A were taken up in 3 ml of methanol, and 0.533 ml (0.533 mmol) of a 1M aqueous sodium hydroxide solution were added. The mixture was then reacted at 140° C. in a single mode microwave oven (Emrys Optimizer) for 45 min. The reaction was checked, showing incomplete conversion (TLC: silica gel, cyclohexane/ethyl acetate=7/3). The mixture was reacted in a microwave oven at 160° C. for a further 30 min. The mixture was concentrated, taken up in 10 ml of water and acidified with 2N hydrochloric acid. The volatile components were removed by distillation under reduced pressure, and the product was then purified by preparative HPLC (mobile phase: acetonitrile/water with 0.1% formic acid, gradient 20:80→95:5). Drying under high vacuum gave 19 mg (36% of theory) of the target compound.

LC-MS (method 2): $R_t$=2.00 min; MS (ESIpos): m/z=302 [M+H]⁺.

¹H-NMR (400 MHz, DMSO-d₆): δ [ppm]=0.88 (d, 6H), 1.28 (t, 3H), 2.00 (sept, 1H), 2.56 (d, 2H), 2.82 (q, 2H), 7.29 (dt, 1H), 7.54 (mz, 1H), 7.77 (s, 1H), 7.93 (mz, 1H), 7.99 (d, 1H), 13.56 (sbr, 1H).

Example 11

2-Ethyl-6-(3,5-difluorophenyl)-4-isobutylnicotinic acid

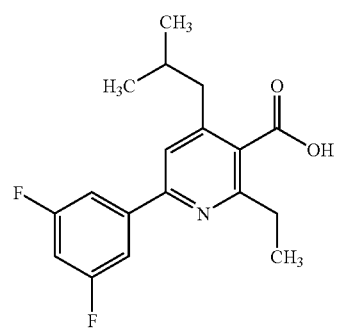

73 mg (0.219 mmol) of Example 16A were taken up in 4 ml of methanol, and 0.657 ml (0.657 mmol) of a 1M aqueous sodium hydroxide solution was added. The mixture was then reacted at 140° C. in a single mode microwave oven (Emrys Optimizer) for 45 min. The reaction was checked, showing incomplete conversion (TLC: silica gel, cyclohexane/ethyl acetate=7/3). The mixture was reacted at 160° C. in a microwave oven for a further 30 min. The mixture was concentrated, taken up in 10 ml of water and acidified with 2N hydrochloric acid. The volatile components were removed by distillation under reduced pressure and the product was then purified by preparative HPLC (mobile phase: acetonitrile/water with 0.1% formic acid, gradient 20:80→95:5). Drying under high vacuum gave 7 mg (10% of theory) of the target compound.

LC-MS (method 2): $R_t$=2.32 min; MS (ESIpos): m/z=320 [M+H]⁺.

¹H-NMR (400 MHz, DMSO-d₆): δ [ppm]=0.88 (d, 6H), 1.28 (t, 3H), 2.02 (sept, 1H), 2.56 (d, 2H), 2.82 (q, 2H), 7.31 (tt, 1H), 7.80-7.90 (m, 3H), 13.55 (s, 1H).

Example 12

6-(3-Fluoro-4-methylphenyl)-4-isobutyl-2-(trifluoromethyl)nicotinic acid

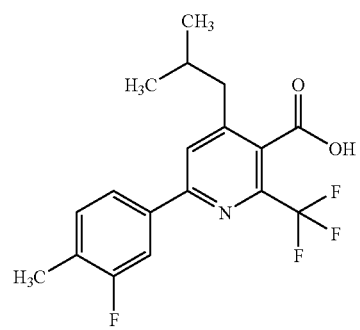

73.0 mg (0.190 mmol) of Example 19A were taken up in 4 ml of ethanol, and 0.286 ml (0.571 mmol) of a 2M aqueous potassium hydroxide solution was added. The mixture was then reacted in a single mode microwave (Emrys Optimizer) at 160° C. for 60 min. Hardly any conversion was detected (TLC). Thus, another 2.00 ml (4.00 mmol) of a 2M aqueous potassium hydroxide solution were added. The mixture was heated in a microwave oven at 180° C. For 30 min. The mixture was then concentrated, taken up in 10 ml of water and acidified with 2N hydrochloric acid. The mixture was extracted with ethyl acetate and dried with magnesium sulfate, and the solvent was removed by distillation under reduced pressure. The product was then purified by preparative HPLC (mobile phase: acetonitrile/water with 0.1% formic acid, gradient 20:80→95:5). This gave 28 mg (39% of theory) of the target compound.

LC-MS (method 6): $R_t$=1.44 min; MS (ESIpos): m/z=356 [M+H]$^+$.

$^1$H-NMR (400 MHz, DMSO-d$_6$): δ [ppm]=0.89 (d, 6H), 2.07 (sept, 1H), 2.31 (s, 3H), 2.64 (d, 2H), 7.47 (t, 1H), 7.92 (mz, 1H), 7.94 (s, 1H), 8.25 (s, 1H), 14.15 (sbr, 1H).

Example 13

6-(3,5-Difluorophenyl)-4-isobutyl-2-(trifluoromethyl)nicotinic acid

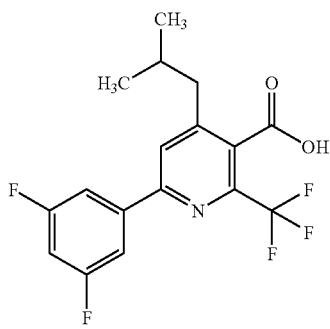

57.0 mg (0.147 mmol) of Example 20A were taken up in 4 ml of ethanol, and 0.221 ml (0.441 mmol) of a 2M potassium hydroxide solution was added. The mixture was then reacted in a single mode microwave (Emrys Optimizer) at 160° C. for 60 min. Hardly any conversion was detected (TLC). Thus, another 2.00 ml (4.00 mmol) of a 2M potassium hydroxide solution were added. The mixture was heated in a microwave oven at 180° C. for 30 min. The mixture was then concentrated, taken up in 10 ml of water and acidified with 2N hydrochloric acid. The mixture was extracted with ethyl acetate and dried with magnesium sulfate, and the solvent was removed by distillation under reduced pressure. The product was then purified by preparative HPLC (mobile phase: acetonitrile/water with 0.1% formic acid, gradient 20:80→95:5). This gave 14 mg (26% of theory) of the target compound.

LC-MS (method 6): $R_t$=1.39 min; MS (ESIpos): m/z=360 [M+H]$^+$.

$^1$H-NMR (400 MHz, DMSO-d$_6$): δ [ppm]=0.89 (d, 6H), 2.09 (sept, 1H), 2.64 (d, 2H), 7.43 (tt, 1H), 7.89 (mz, 2H), 8.36 (s, 1H), 14.23 (sbr, 1H).

Example 14

6-(4-Methylphenyl)-4-isobutyl-2-(trifluoromethyl)nicotinic acid potassium salt

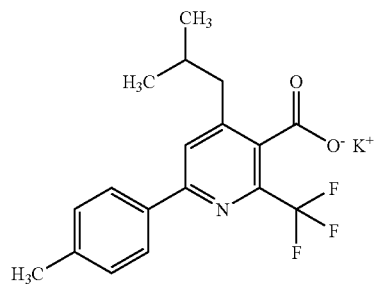

54.0 mg (0.148 mmol) of Example 21A were taken up in 4 ml of ethanol, and 0.222 ml (0.443 mmol) of a 2M potassium hydroxide solution was added. The mixture was then reacted at reflux temperature overnight. Hardly any conversion was detected (TLC). Thus, another 2.00 ml (4.00 mmol) of a 2M potassium hydroxide solution were added. The mixture was then heated in a single mode microwave (Emrys Optimizer) at 180° C. for 30 min. The mixture was concentrated and then purified as an alkaline solution by preparative HPLC (mobile phase: acetonitrile/water, gradient 20:80→95:5). This gave 21 mg (38% of theory) of the target compound.

LC-MS (method 1): $R_t$=3.15 min; MS (ESIneg): m/z=336 [M−K$^+$]$^-$.

$^1$H-NMR (400 MHz, DMSO-d$_6$): δ [ppm]=0.86 (d, 6H), 2.15 (sept, 1H), 2.36 (s, 3H), 2.57 (d, 2H), 7.30 (d, 2H), 7.80 (s, 1H), 7.95 (d, 2H).

Example 15

4-Isobutyl-2-(trifluoromethyl)-6-[4-(trifluoromethyl)phenyl]nicotinic acid potassium salt

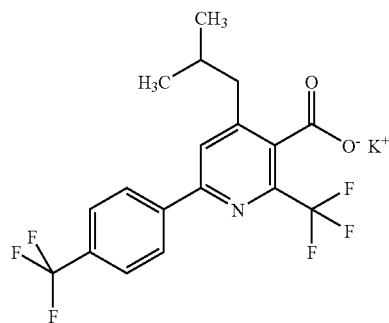

57.0 mg (0.136 mmol) of Example 22A were taken up in 4 ml of ethanol, and 0.204 ml (0.408 mmol) of a 2M aqueous potassium hydroxide solution was added. The mixture was then reacted at reflux temperature overnight. Hardly any conversion was detected (TLC). Thus, another 2.00 ml (4.00 mmol) of a 2M aqueous potassium hydroxide solution were added. The mixture was then heated in a single mode microwave (Emrys Optimizer) at 180° C. for 30 min. The mixture was concentrated and then purified as an alkaline solution by preparative HPLC (mobile phase: acetonitrile/water, gradient 20:80→95:5). This gave 38 mg (65% of theory) of the target compound.

LC-MS (method 1): $R_t$=3.38 min; MS (ESIneg): m/z=390 $[M-K^+]^-$.

$^1$H-NMR (400 MHz, DMSO-$d_6$): δ [ppm]=0.88 (d, 6H), 2.18 (sept, 1H), 2.62 (d, 2H), 7.86 (d, 2H), 7.99 (s, 1H), 8.29 (d, 2H).

Example 16

4-Isobutyl-6-(3-methylphenyl)-2-(trifluoromethyl) nicotinic acid potassium salt

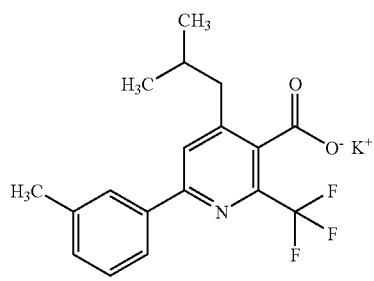

53.0 mg (0.145 mmol) of Example 23A were taken up in 4 ml of ethanol, and 0.218 ml (0.435 mmol) of a 2M aqueous potassium hydroxide solution was added. The mixture was then reacted at reflux temperature overnight. Hardly any conversion was detected (TLC). Thus, another 2.00 ml (4.00 mmol) of a 2M aqueous potassium hydroxide solution were added. The mixture was then heated in a single mode microwave (Emrys Optimizer) at 180° C. for 30 min. The mixture was concentrated and then purified as an alkaline solution by preparative HPLC (mobile phase: acetonitrile/water, gradient 20:80→95:5). This gave 30 mg (55% of theory) of the target compound.

LC-MS (method 1): $R_t$=3.15 min; MS (ESIneg): m/z=336 $[M-K^+]^-$.

$^1$H-NMR (400 MHz, DMSO-$d_6$): δ [ppm]=0.86 (d, 6H), 2.16 (sept, 1H), 2.40 (s, 3H), 2.58 (d, 2H), 7.24 (d, 1H), 7.37 (t, 1H), 7.81 (s, 1H), 7.83 (d, 1H), 7.86 (s, 1H).

Example 17

6-(4-Chlorophenyl)-2-(isopropylamino)-4-(trifluoromethyl)nicotinic acid

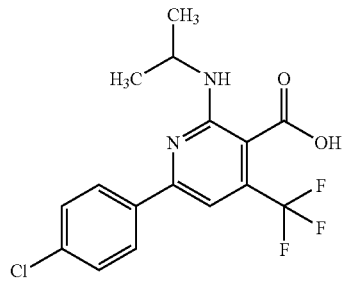

150.0 mg (0.428 mmol) of Example 24A and 0.147 ml (1.714 mmol) of isopropylamine were initially charged in 3 ml of THF. 0.149 ml (1.071 mmol) of triethylamine was added, and the mixture was reacted at room temperature for 5 d. The volatile components were removed on a rotary evaporator. The crude material obtained in this manner was taken up in 4 ml of ethanol, and 1.07 ml (2.14 mmol) of a 2M potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 20 mg (13% of theory) of the target compound.

LC-MS (method 6): $R_t$=1.56 min; MS (ESIpos): m/z=359 $[M+H]^+$.

$^1$H-NMR (400 MHz, DMSO-$d_6$): δ [ppm]=1.25 (d, 6H), 4.36 (m, 1H), 6.81 (mz, 1H), 7.41 (s, 1H), 7.57 (d, 2H), 8.18 (d, 2H), 13.97 (sbr, 1H).

Example 18

6-(4-Chlorophenyl)-2-(isobutylamino)-4-(trifluoromethyl)nicotinic acid

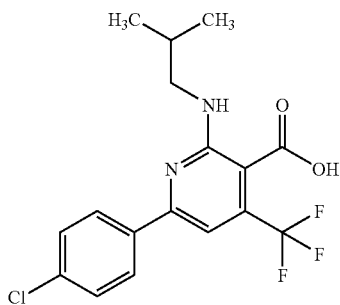

150.0 mg (0.428 mmol) of Example 24A and 0.170 ml (1.714 mmol) of isobutylamine were initially charged in 3 ml of THF. 0.149 ml (1.071 mmol) of triethylamine was added, and the mixture was reacted at room temperature for 5 d. The volatile components were removed on a rotary evaporator. The crude material obtained in this manner was taken up in 4 ml of ethanol, and 1.07 ml (2.14 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 20 mg (13% of theory) of the target compound.

LC-MS (method 2): $R_t$=2.79 min; MS (ESIpos): m/z=372 $[M+H]^+$.

$^1$H-NMR (400 MHz, DMSO-$d_6$): δ [ppm]=0.93 (d, 6H), 1.98 (sept, 1H), 7.17 (mz, 1H), 7.40 (s, 1H), 7.57 (d, 2H), 8.17 (d, 2H), 13.94 (sbr, 1H).

Example 19

2-(Isobutylamino)-6-(4-methylphenyl)-4-(trifluoromethyl)nicotinic acid

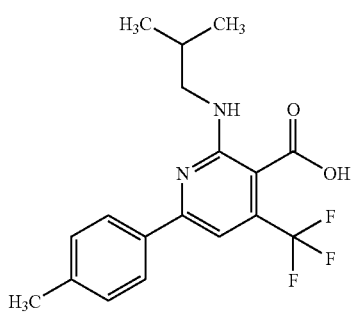

150.0 mg (0.455 mmol) of Example 25A and 0.181 ml (1.820 mmol) of isobutylamine were initially charged in 3 ml of THF. 0.159 ml (1.137 mmol) of triethylamine was added, and the mixture was reacted at room temperature for 5 d. The volatile components were removed on a rotary evaporator. The crude material obtained in this manner was taken up in 4 ml of ethanol, and 1.138 ml (2.28 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 30 mg (19% of theory) of the target compound.

LC-MS (method 2): $R_t$=2.68 min; MS (ESIpos): m/z=353 [M+H]$^+$.

$^1$H-NMR (400 MHz, DMSO-d$_6$): δ [ppm]=0.93 (d, 6H), 1.98 (sept, 1H), 2.37 (s, 3H), 7.19 (mz, 1H), 7.32 (d, 2H), 7.34 (s, 1H), 8.03 (d, 2H), 13.85 (sbr, 1H).

Example 20

2-(Isopropylamino)-6-(4-methylphenyl)-4-(trifluoromethyl)nicotinic acid

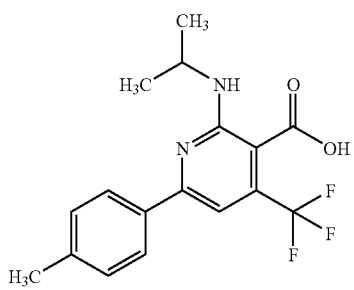

150.0 mg (0.455 mmol) of Example 25A and 0.155 ml (1.820 mmol) of isopropylamine were initially charged in 3 ml of THF. 0.159 ml (1.137 mmol) of triethylamine was added, and the mixture was reacted at room temperature for 5 d. The volatile components were removed on a rotary evaporator. The crude material obtained in this manner was taken up in 4 ml of ethanol, and 1.138 ml (2.28 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 20 mg (13% of theory) of the target compound.

LC-MS (method 6): $R_t$=1.52 min; MS (ESIpos): m/z=339 [M+H]$^+$.

$^1$H-NMR (400 MHz, DMSO-d$_6$): δ [ppm]=1.25 (d, 6H), 2.37 (s, 3H), 4.37 (m, 1H), 6.83 (mz, 1H), 7.32 (d, 2H), 7.36 (s, 1H), 8.04 (d, 2H), 13.87 (sbr, 1H).

Example 21

6-(4-Chlorophenyl)-2-(cyclopropylamino)-4-(trifluoromethyl)nicotinic acid

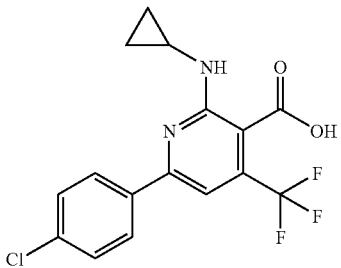

150.0 mg (0.428 mmol) of Example 24A and 0.119 ml (1.714 mmol) of cyclopropylamine were initially charged in 3 ml of THF. 0.149 ml (1.071 mmol) of triethylamine was added, and the mixture was reacted at room temperature for 5 d. The volatile components were removed on a rotary evaporator. The crude material obtained in this manner was taken up in 4 ml of ethanol, and 1.07 ml (2.14 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 22 mg (14% of theory) of the target compound.

LC-MS (method 2): $R_t$=2.51 min; MS (ESIpos): m/z=357 [M+H]$^+$.

$^1$H-NMR (400 MHz, DMSO-d$_6$): δ [ppm]=0.52-0.58 (m, 2H), 0.79 (mz, 2H), 2.89 (mz, 1H), 7.14 (sbr, 1H), 7.50 (s, 1H), 7.57 (d, 2H), 8.24 (d, 2H), 13.88 (sbr, 1H).

Example 22

6-(4-Chlorophenyl)-2-[(cyclopropylmethyl)amino]-4-(trifluoromethyl)nicotinic acid

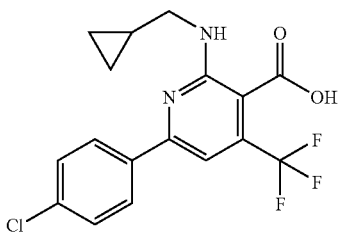

150.0 mg (0.428 mmol) of Example 24A and 0.147 ml (1.714 mmol) of cyclopropylmethanamine were initially charged in 3 ml of THF. 0.149 ml (1.071 mmol) of triethylamine was added, and the mixture was reacted at room temperature for 5 d. The volatile components were removed on a rotary evaporator. The crude material obtained in this manner was taken up in 4 ml of ethanol, and 1.07 ml (2.14 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 62 mg (39% of theory) of the target compound.

LC-MS (method 1): $R_t$=3.51 min; MS (ESIpos): m/z=371 [M+H]$^+$.

$^1$H-NMR (400 MHz, DMSO-d$_6$): δ [ppm]=0.28 (mz, 2H), 0.45 (mz, 2H), 1.19 (mz, 1H), 3.38 (d, 2H), 7.15 (sbr, 1H), 7.42 (s, 1H), 7.57 (d, 2H), 8.18 (d, 2H), 13.96 (sbr, 1H).

Example 23

2-(Cyclopropylamino)-6-(4-methylphenyl)-4-(trifluoromethyl)nicotinic acid

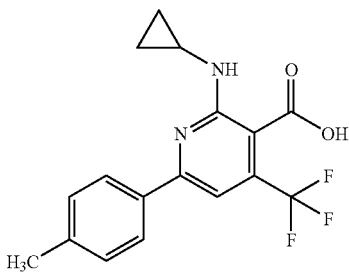

150.0 mg (0.455 mmol) of Example 25A and 0.126 ml (1.820 mmol) of cyclopropylamine were initially charged in 3 ml of THF. 0.159 ml (1.137 mmol) of triethylamine was added, and the mixture was reacted at room temperature for 5 d. The volatile components were removed on a rotary evaporator. The crude material obtained in this manner was taken up in 4 ml of ethanol, and 1.14 ml (2.28 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 5 mg (3% of theory) of the target compound.

LC-MS (method 1): $R_t$=3.23 min; MS (ESIpos): m/z=337 [M+H]$^+$.

$^1$H-NMR (400 MHz, DMSO-d$_6$): δ [ppm]=0.55 (mz, 2H), 0.79 (mz, 2H), 2.38 (s, 3H), 2.91 (mz, 1H), 7.13 (sbr, 1H), 7.32 (d, 2H), 7.42 (s, 1H), 8.11 (d, 2H), 13.82 (sbr, 1H).

Example 24

2-[(Cyclopropylmethyl)amino]-6-(4-methylphenyl)-4-(trifluoromethyl)nicotinic acid

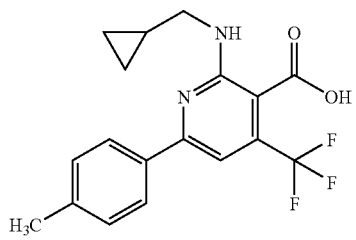

150.0 mg (0.455 mmol) of Example 25A and 0.156 ml (1.820 mmol) of cyclopropylmethanamine were initially charged in 3 ml of THF. 0.159 ml (1.137 mmol) of triethylamine was added, and the mixture was reacted at room temperature for 5 d. The volatile components were removed on a rotary evaporator. The crude material obtained in this manner was taken up in 4 ml of ethanol, and 1.14 ml (2.28 mmol) of a 2M aqueous potassium hydroxide solution were added. The mixture was then heated in a single mode microwave (Emrys Optimizer) at 140° C. for 30 min. The mixture was added to water and acidified with 1N hydrochloric acid. The mixture was extracted with ethyl acetate (2×), the combined organic phases were dried with magnesium sulfate and the solvent was then removed by distillation under reduced pressure. The product was then purified by preparative HPLC (mobile phase: acetonitrile/water, gradient 20:80→95:5). This gave 25 mg (16% of theory) of the target compound.

LC-MS (method 2): $R_t$=2.57 min; MS (ESIpos): m/z=351 [M+H]$^+$.

$^1$H-NMR (400 MHz, DMSO-d$_6$): δ [ppm]=0.28 (mz, 2H), 0.45 (mz, 2H), 1.19 (mz, 1H), 2.37 (s, 3H), 3.39 (d, 2H), 7.16 (sbr, 1H), 7.32 (d, 2H), 7.35 (s, 1H), 8.04 (d, 2H), 13.86 (sbr, 1H).

Example 25

6-(4-Chlorophenyl)-2-isobutyl-4-(trifluoromethyl)nicotinic acid

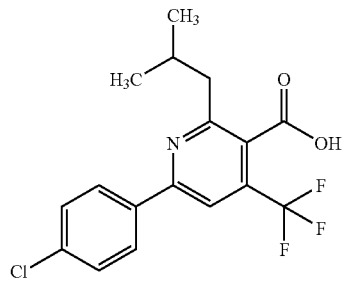

100 mg (0.269 mmol) of Example 26A were taken up in 4 ml of ethanol, and 2.00 ml (4.00 mmol) of a 2M aqueous potassium hydroxide solution were added. The mixture was stirred at 80° C. overnight. However, since only partial conversion was achieved, the mixture was reacted in a single mode microwave (Emrys Optimizer) at 160° C. for another 45 min. The mixture was concentrated, taken up in 10 ml of water and acidified with 1N hydrochloric acid. The mixture was extracted with ethyl acetate (2×10 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 59 mg (61% of theory) of the target compound.

LC-MS (method 6): $R_t$=1.50 min; MS (ESIpos): m/z=358 [M+H]$^+$.

$^1$H-NMR (400 MHz, DMSO-d$_6$): δ [ppm]=0.93 (d, 6H), 2.29 (sept, 1H), 2.78 (d, 2H), 7.61 (d, 2H), 8.21 (s, 1H), 8.25 (d, 2H), 14.18 (sbr, 1H).

Example 26

2-Isobutyl-6-(4-methylphenyl)-4-(trifluoromethyl)nicotinic acid

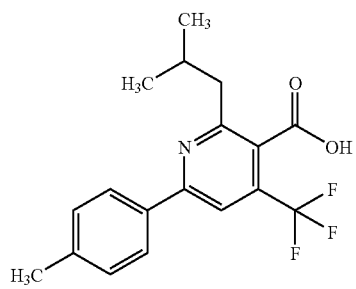

60 mg (0.171 mmol) of Example 27A were taken up in 2.4 ml of ethanol, and 2.00 ml (4.00 mmol) of a 2M aqueous potassium hydroxide solution were added. The mixture was stirred at 80° C. overnight. However, since only partial conversion was achieved, the mixture was reacted in a single mode microwave (Emrys Optimizer) at 160° C. for another 45 min. The mixture was concentrated, taken up in 10 ml of water and acidified with 1N hydrochloric acid. The mixture was extracted with ethyl acetate (2×10 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 45 mg (43% of theory) of the target compound.

LC-MS (method 6): $R_t$=1.47 min; MS (ESIpos): m/z=338 [M+H]$^+$.

$^1$H-NMR (400 MHz, DMSO-d$_6$): δ [ppm]=0.93 (d, 6H), 2.29 (sept, 1H), 2.38 (s, 3H), 2.77 (d, 2H), 7.35 (d, 2H), 8.08-8.16 (m, 3H), 14.10 (sbr, 1H).

Example 27

2-Isobutoxy-6-(4-methylphenyl)-4-(trifluoromethyl)nicotinic acid

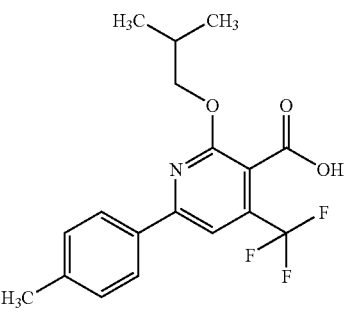

29 mg (0.079 mmol) of Example 28A were taken up in 1.0 ml of ethanol, and 0.50 ml (1.00 mmol) of a 2M aqueous potassium hydroxide solution was added. The mixture was stirred at 80° C. overnight. However, since only partial conversion was achieved, the mixture was reacted in a single mode microwave (Emrys Optimizer) at 160° C. for another 45 min. The mixture was concentrated, taken up in 10 ml of water and acidified with 1N hydrochloric acid. The mixture was extracted with ethyl acetate (2×10 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 14 mg (50% of theory) of the target compound.

LC-MS (method 6): $R_t$=1.50 min; MS (ESIpos): m/z=354 [M+H]$^+$.

$^1$H-NMR (400 MHz, DMSO-d$_6$): δ [ppm]=0.99 (d, 6H), 2.07 (sept, 1H), 2.38 (s, 3H), 4.27 (d, 2H), 7.35 (d, 2H), 7.83 (s, 1H), 8.09 (d, 2H), 13.82 (sbr, 1H).

Example 28

6-(4-Chlorophenyl)-2-isopropoxy-4-(trifluoromethyl)nicotinic acid

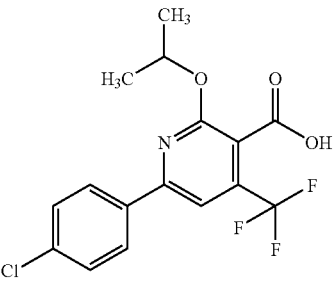

49 mg (0.131 mmol) of Example 29A were taken up in 2.0 ml of ethanol, and 0.50 ml (1.00 mmol) of a 2M aqueous potassium hydroxide solution was added. The mixture was stirred at 80° C. overnight. The mixture was concentrated, taken up in 10 ml of water and acidified with 1N hydrochloric acid. The mixture was extracted with ethyl acetate (2×10 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 14 mg (50% of theory) of the target compound.

LC-MS (method 6): $R_t$=1.45 min; MS (ESIpos): m/z=360 [M+H]$^+$.

$^1$H-NMR (400 MHz, DMSO-d$_a$): δ [ppm]=1.36 (d, 6H), 5.48 (sept, 1H), 7.60 (d, 2H), 7.90 (s, 1H), 8.22 (d, 2H), 13.82 (sbr, 1H).

Example 29

6-(4-Chlorophenyl)-2-isobutoxy-4-(trifluoromethyl)nicotinic acid

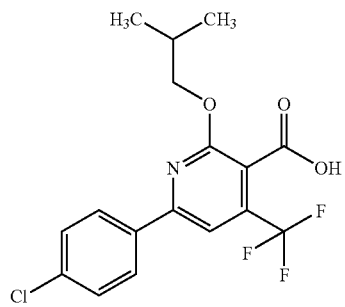

52 mg (0.134 mmol) of Example 30A were taken up in 2.0 ml of ethanol, and 0.50 ml (1.00 mmol) of a 2M aqueous potassium hydroxide solution was added. The mixture was stirred at 80° C. overnight. The mixture was concentrated, taken up in 10 ml of water and acidified with 1N hydrochloric acid. The mixture was extracted with ethyl acetate (2×10 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 28 mg (56% of theory) of the target compound.

LC-MS (method 2): $R_t$=2.61 min; MS (ESIneg): m/z=372 [M+H]$^+$.

$^1$H-NMR (400 MHz, DMSO-d$_6$): δ [ppm]=0.99 (d, 6H), 2.07 (sept, 1H), 4.28 (d, 2H), 7.60 (d, 2H), 7.93 (s, 1H), 8.23 (d, 2H), 13.90 (sbr, 1H).

Example 30

6-(3-Fluoro-4-methylphenyl)-2-[(2-methylcyclopropyl)methoxy]-4-(trifluoromethyl)nicotinic acid

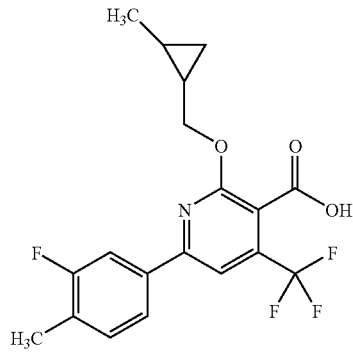

37 mg (0.431 mmol) of (2-methylcyclopropyl)methanol and 17 mg (0.431 mmol) of sodium hydride (60% strength dispersion in mineral oil) were initially charged in 5 ml of tetrahydrofuran. The reaction mixture was stirred at room temperature for 60 minutes. 100 mg (0.288 mol) of methyl 2-chloro-6-(3-fluoro-4-methylphenyl)-4-(trifluoromethyl)nicotinate (Example 2A) in 2 ml of tetrahydrofuran were then added. The mixture was stirred at reflux temperature for 3 h and then at room temperature overnight. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 20 mg (18% of theory) of the target compound.

LC-MS (method 1): $R_t$=3.25 min; MS (ESIpos): m/z=384 [M+H]$^+$.

$^1$H-NMR (400 MHz, DMSO-d$_6$): δ [ppm]=0.31-0.36 (m, 1H), 0.53-0.57 (m, 1H), 0.79-0.85 (m, 1H), 1.03 (d, 3H), 1.09 (d, 1H), 2.31 (s, 3H), 4.42 (dd, 1H), 4.41 (dd, 1H), 7.44 (t, 1H), 7.91 (s, 1H), 7.95-7.99 (2H). 13.86 (sbr, 1H).

Example 31

6-(3,5-Difluorophenyl)-2-(3,3-dimethylbutoxy)-4-(trifluoromethyl)nicotinic acid

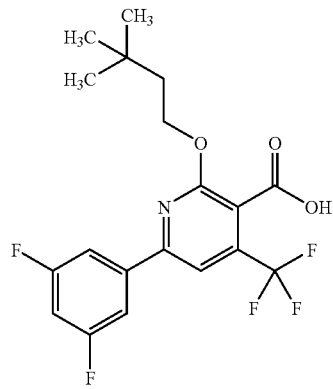

35 mg (0.341 mmol) of 3,3-dimethylbutan-1-ol and 14 mg (0.341 mmol) of sodium hydride (60% strength dispersion in mineral oil) were initially charged in 5 ml of tetrahydrofuran. The reaction mixture was stirred at room temperature for 60 minutes. 100 mg (0.288 mol) of Example 46A were then added as a solution in 2 ml of tetrahydrofuran. The reaction mixture was then stirred at reflux temperature for 3 h and at room temperature overnight. For work-up, water was added, the reaction mixture was made basic with a 2M aqueous sodium hydroxide solution and extracted with ethyl acetate and the aqueous phase was adjusted to pH 1 using 1N hydrochloric acid. After removal of the volatile components on a rotary evaporator, the product was purified by preparative HPLC (mobile phase: acetonitrile/water, gradient 10:90→90:10). This gave 12 mg (11% of theory) of the target compound.

LC-MS (method 1): $R_t$=3.42 min; MS (ESIpos): m/z=404 [M+H]$^+$.

$^1$H-NMR (400 MHz, DMSO-d$_6$): δ [ppm]=0.98 (s, 9H), 1.68 (t, 2H), 4.58 (t, 2H), 7.42 (t, 1H), 7.96 (s, 1H), 7.98 (s, 1H), 8.05 (s, 1H), 13.96 (sbr, 1H).

Example 32

6-(3-Fluoro-4-methylphenyl)-2-isobutoxy-4-(trifluoromethyl)nicotinic acid

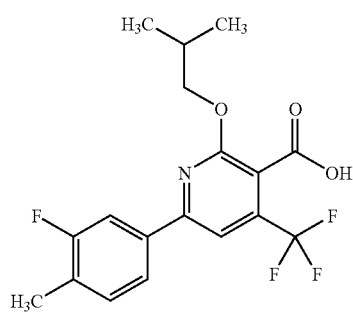

114 mg (2.854 mmol) of sodium hydroxide were added to 55 mg (0.14 mmol) of Example 37A as a solution in 2 ml of ethanol and 1 ml of water, and the mixture was stirred at reflux temperature overnight. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 20 mg (38% of theory) of the target compound.

LC-MS (method 2): $R_t$=2.55 min; MS (ESIpos): m/z=372 [M+H]$^+$.

$^1$H-NMR (400 MHz, DMSO-d$_6$): δ [ppm]=1.00 (d, 6H), 2.30 (s, 3H), 4.28 (d, 2H), 7.45 (t, 1H), 7.92 (s, 1H), 7.93-7.95 (m, 3H), 13.87 (sbr, 1H).

Example 33

6-(3-Fluoro-4-methylphenyl)-2-(3-methylbutoxy)-4-(trifluoromethyl)nicotinic acid

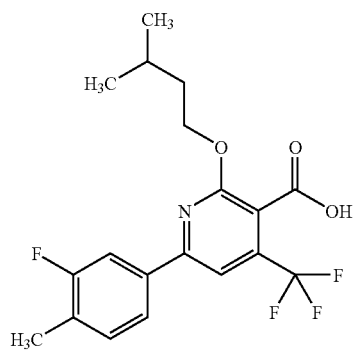

38 mg (0.431 mmol) of 3-methyl-1-butanol and 17 mg (0.431 mmol) of sodium hydride (60% strength dispersion in mineral oil) were initially charged in 3 ml of tetrahydrofuran. The reaction mixture was stirred at room temperature for 60 minutes. 100 mg (0.288 mol) of Example 2A were then added as a solution in 2 ml of tetrahydrofuran. The mixture was then stirred at reflux for 7 h and at room temperature overnight. For work-up, the reaction mixture was adjusted to pH 1 using 1N hydrochloric acid. After removal of the volatile components on a rotary evaporator, the mixture was purified by preparative HPLC (mobile phase: acetonitrile/water, gradient 10:90→90:10). This gave 16 mg (15% of theory) of the target compound.

LC-MS (method 1): $R_t$=3.35 min; MS (ESIpos): m/z=386 [M+H]$^+$.

$^1$H-NMR (400 MHz, DMSO-d$_6$): δ [ppm]=0.94 (d, 6H), 1.66 (m, 2H), 1.78 (m, 1H), 2.30 (s, 3H), 4.54 (t, 2H), 7.45 (t, 1H), 7.92 (s, 1H), 7.96-8.00 (m, 2H), 13.86 (sbr, 1H).

Example 34

2-Ethoxy-6-(3-fluoro-4-methylphenyl)-4-(trifluoromethyl)nicotinic acid

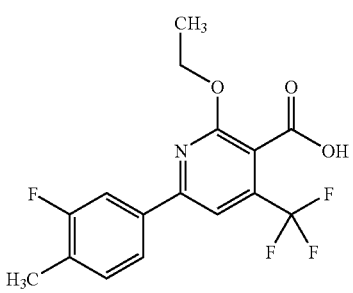

60 mg (1.511 mmol) of sodium hydroxide were added to 27 mg (0.076 mmol) of Example 38A in 2 ml of ethanol and 1 ml of water, and the mixture was stirred at 90° C. for 4 h. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 13 mg (78% of theory) of the target compound.

LC-MS (method 1): $R_t$=2.99 min; MS (ESIpos): m/z=344 [M+H]$^+$.

$^1$H-NMR (400 MHz, DMSO-d$_6$): δ [ppm]=1.37 (t, 3H), 2.30 (s, 1H), 4.55 (q, 2H), 7.44 (t, 1H), 7.92-7.99 (3H), 13.85 (sbr, 1H).

Example 35

2-(Cyclopentylamino)-6-(3-fluoro-4-methylphenyl)-4-(trifluoromethyl)nicotinic acid hydrochloride

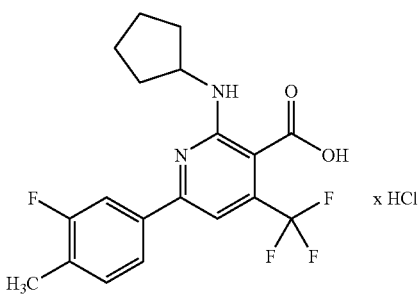

85 mg (2.12 mmol) of sodium hydroxide were added to 42 mg (0.106 mmol) of Example 39A in 2 ml of ethanol and 1 ml of water, and the mixture was stirred at 80° C. for 4 h. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 35 mg (78% of theory) of the target compound.

LC-MS (method 2): R$_t$=2.76 min; MS (ESIpos): m/z=383 [M+H−HCl]$^+$.

$^1$H-NMR (400 MHz, DMSO-d$_6$): δ [ppm]=1.47-1.73 (m, 6H), 2.04-2.08 (m, 2H), 2.29 (s, 3H), 4.42 (m, 1H), 6.96 (sbr, 1H), 7.40-7.43 (m, 2H), 7.90-7.93 (m, 2H), 13.95 (sbr, 1H).

Example 36

2-(Diethylamino)-6-(3-fluoro-4-methylphenyl)-4-(trifluoromethyl)nicotinic acid

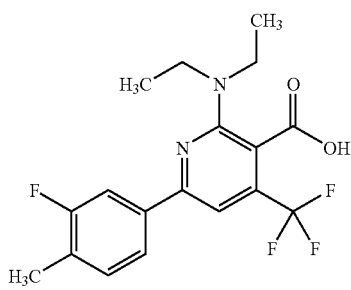

65 mg (1.64 mmol) of sodium hydroxide were added to 31 mg (0.082 mmol) of Example 40A in 2 ml of ethanol and 1 ml of water, and the mixture was stirred at 80° C. for 3 days. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 6 mg (20% of theory) of the target compound.

LC-MS (method 6): R$_t$=1.42 min; MS (ESIpos): m/z=371 [M+H]$^+$.

$^1$H-NMR (400 MHz, DMSO-d$_6$): δ [ppm]=1.71 (t, 6H), 2.29 (s, 3H), 3.53 (q, 4H), 7.42 (t, 1H), 7.53 (s, 1H), 7.87-7.91 (m, 2H), 13.85 (sbr, 1H).

Example 37

6-(3-Fluoro-4-methylphenyl)-2-(3-methylbutyl)-4-(trifluoromethyl)nicotinic acid

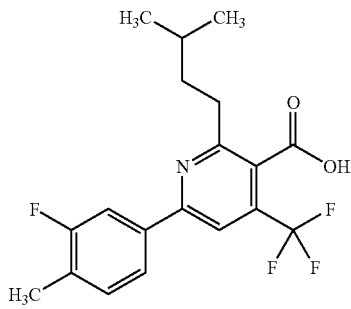

62 mg (1.56 mmol) of sodium hydroxide were added to 30 mg (0.078 mmol) of Example 41A in 2 ml of ethanol and 1 ml of water. The mixture was then stirred at 80° C. overnight. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 14 mg (48% of theory) of the target compound.

LC-MS (method 6): R$_t$=1.59 min; MS (ESIpos): m/z=370 [M+H]$^+$.

$^1$H-NMR (400 MHz, DMSO-d$_6$): δ [ppm]=0.92 (d, 6H), 1.58-1.69 (m, 3H), 2.31 (s, 3H), 2.89 (dd, 2H), 7.45 (t, 1H), 7.97-8.01 (m, 2H), 8.17 (s, 1H), 14.19 (sbr, 1H).

Example 38

2-Butyl-6-(3-fluoro-4-methylphenyl)-4-(trifluoromethyl)nicotinic acid

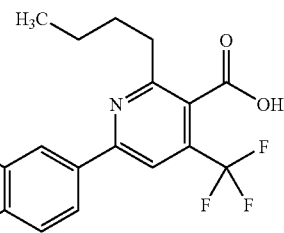

0.68 ml of a 2M aqueous sodium hydroxide solution was added to 25 mg (0.068 mmol) of Example 42A in 1.5 ml of ethanol. The mixture was stirred of reflux temperature overnight. For work-up, the reaction mixture was adjusted to pH 1 using 1N hydrochloric acid. After removal of the volatile components on a rotary evaporator, the product was purified by preparative HPLC (mobile phase: acetonitrile/water, gradient 10:90→90:10). This gave 8 mg (35% of theory) of the target compound.

LC-MS (method 1): R$_t$=3.36 min: MS (ESIpos): m/z=356 [M+H]$^+$.

$^1$H-NMR (400 MHz, DMSO-d$_6$): δ [ppm]=0.92 (t, 3H), 1.37 (m, 2H), 1.76 (m, 2H), 2.31 (s, 3H), 2.88 (t. 2H), 7.45 (t, 1H), 7.97 (s, 1H), 7.99 (d, 1H), 8.17 (s, 1H), 14.26 (sbr, 1H).

Example 39

2-(Cyclopentyloxy)-6-(3-fluoro-4-methylphenyl)-4-(trifluoromethyl)nicotinic acid

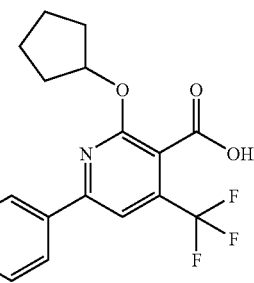

37 mg (0.431 mmol) of cyclopentanol and 17 mg (0.431 mmol) of sodium hydride (60% strength dispersion in mineral oil) were initially charged in 3 ml of tetrahydrofuran. The reaction mixture was stirred at room temperature for 60 minutes. 100 mg (0.288 mol) of Example 2A were then added as a solution in 2 ml of tetrahydrofuran. The mixture was then stirred at reflux for 3 h and at room temperature overnight. For work-up, the reaction mixture was adjusted to pH 1 using 1N hydrochloric acid. After removal of the volatile components on a rotary evaporator, the crude product was purified by preparative HPLC (mobile phase: acetonitrile/water, gradient 10:90→90:10). This gave 25 mg (23% of theory) of the target compound.

LC-MS (method 1): $R_t$=3.23 min; MS (ESIpos): m/z=382 [M–H]$^+$.

$^1$H-NMR (400 MHz, DMSO-d$_6$): δ [ppm]=1.60-1.80 (m, 6H), 1.99-2.02 (m, 2H), 2.31 (s, 3H), 5.59-5.63 (m, 1H), 7.45 (t, 1H), 7.96 (s, 1H), 7.98 (d, 1H), 13.79 (sbr, 1H).

Example 40

2-(Cyclopentylmethoxy)-6-(3-fluoro-4-methylphenyl)-4-(trifluoromethyl)nicotinic acid

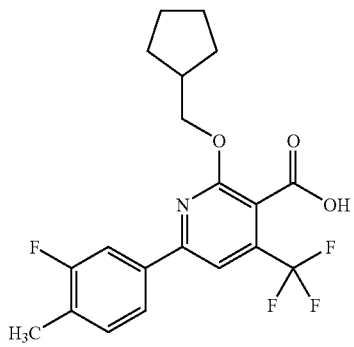

43 mg (0.431 mmol) of cyclopentylmethanol and 17 mg (0.431 mmol) of sodium hydride (60% strength dispersion in mineral oil) were initially charged in 3 ml of tetrahydrofuran. The reaction mixture was stirred at room temperature for 60 minutes. 100 mg (0.288 mol) of Example 2A were then added as a solution in 2 ml of tetrahydrofuran. The mixture was stirred at reflux for 3 h and then at room temperature overnight. For work-up, the reaction mixture was adjusted to pH 1 using 1N hydrochloric acid. After removal of the volatile components on a rotary evaporator, the mixture was purified by preparative HPLC (mobile phase: acetonitrile/water, gradient 10:90→90:10). This gave 22 mg (29% of theory) of the target compound.

LC-MS (method 1): $R_t$=3.36 min; MS (ESIpos): m/z=398 [M+H]$^+$.

$^1$H-NMR (400 MHz, DMSO-d$_6$): δ [ppm]=1.33-1.42 (m, 1.53-1.63 (m, 4H). 1.71-1.78 (m, 2H), 2.31 (s, 3H), 2.28-2.36 (m, 1H), 4.38 (d, 2H), 7.45 (t, 1H), 7.92 (s, 1H), 7.95-7.99 (m, 2H), 13.84 (shr, 1H).

Example 41

2-(Cyclopentylmethoxy)-6-(3-fluoro-4-methylphenyl)-4-(trifluoromethyl)nicotinic acid

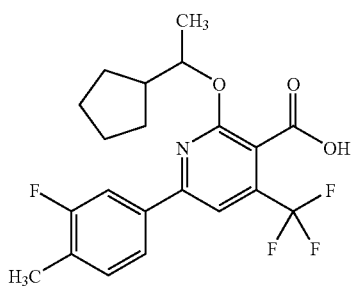

49 mg (0.431 mmol) of 1-cyclopentylethanol and 17 mg (0.431 mmol) of sodium hydride (60% strength dispersion in mineral oil) were initially charged in 3 ml of tetrahydrofuran. The reaction mixture was stirred at room temperature for 60 minutes. 100 mg (0.288 mol) of Example 2A in 2 ml of tetrahydrofuran were then added. The mixture was stirred at reflux for 3 h and then at room temperature overnight. For work-up, the reaction mixture was adjusted to pH 1 using 1N hydrochloric acid. After removal of the volatile components on a rotary evaporator, the crude product was purified by preparative HPLC (mobile phase: acetonitrile/water, gradient 10:90→90:10). This gave 16 mg (14% of theory) of the target compound.

LC-MS (method 1): $R_t$=3.39 min; MS (ESIpos): m/z=412 [M+H]$^+$.

$^1$H-NMR (400 MHz, DMSO-d$_6$): δ [ppm] 1.30-1.73 (m, 11H), 2.10-2.17 (m, 1H), 2.31 (s, 3H), 5.22-5.27 (m, 1H), 7.45 (t, 1H), 7.89 (s, 1H), 7.94 (s, 1H), 7.96 (d, 1H), 13.78 (sbr, 1H).

Example 42

2-(1-Cyclohexylethoxy)-6-(3-fluoro-4-methylphenyl)-4-(trifluoromethyl)nicotinic acid

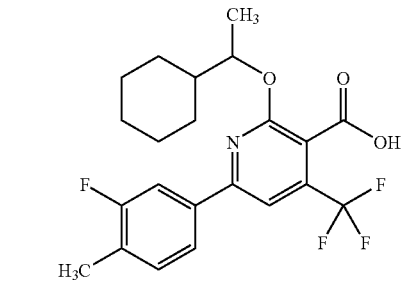

55 mg (0.431 mmol) of 1-cyclohexylethanol and 17 mg (0.431 mmol) of sodium hydride (60% strength dispersion in mineral oil) were initially charged in 3 ml of tetrahydrofuran. The reaction mixture was stirred at room temperature for 60 minutes. 100 mg (0.288 mol) of Example 2A were then added as a solution in 2 ml of tetrahydrofuran. The mixture was stirred at reflux for 3 h and then at room temperature overnight. For work-up, the reaction mixture was adjusted to pH 1 using 1N hydrochloric acid. After removal of the volatile components on a rotary evaporator, the crude product was purified by preparative HPLC (mobile phase: acetonitrile/water, gradient 10:90→90:10). This gave 13 mg (11% of theory) of the target compound.

LC-MS (method 1): $R_t$=3.47 min; MS (ESIpos): m/z=426 [M+H]$^+$.

$^1$H-NMR (400 MHz, DMSO-d$_6$): δ [ppm]=1.01-1.23 (m, 5H); 1.32 (d, 3H), 1.53-1.79 (m, 5H), 1.85 (dm, 1H), 2.31 (s, 3H), 5.17-5.23 (m, 1H), 7.45 (t, 1H), 7.88 (s, 1H), 7.92 (s, 1H), 7.95 (d, 1H), 13.81 (sbr, 1H).

Example 43

2-(Cyclopropylmethoxy)-6-(3-fluoro-4-methylphenyl)-4-(trifluoromethyl)nicotinic acid

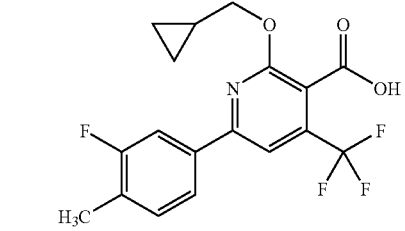

77 mg (1.930 mmol) of sodium hydroxide were added to 37 mg (0.097 mmol) of Example 43A in 1 ml of ethanol and 0.5 ml of water. The mixture was then stirred at reflux temperature overnight. For work-up, the reaction mixture was adjusted to pH 1 using 1N hydrochloric acid. After removal of the volatile components on a rotary evaporator, the crude product was purified by preparative HPLC (mobile phase: acetonitrile/water, gradient 10:90→90:10). This gave 8 mg (22% of theory) of the target compound.

LC-MS (method 5): $R_t$=4.07 min; MS (ESIpos): m/z=370 [M+H]$^+$.

$^1$H-NMR (400 MHz, DMSO-d$_6$): δ [ppm]=0.37-0.41 (m, 2H), 0.54-0.59 (m, 2H), 1.25-1.34 (m, 1H), 2.31 (s, 3H), 4.35 (d, 2H), 7.45 (t, 1H), 7.92 (s, 1H), 7.95-7.99 (m, 2H), 13.88 (sbr, 1H).

Example 44

2-[(Cyclopropylmethyl)amino]-6-(3-fluoro-4-methylphenyl)-4-(trifluoromethyl)nicotinic acid hydrochloride

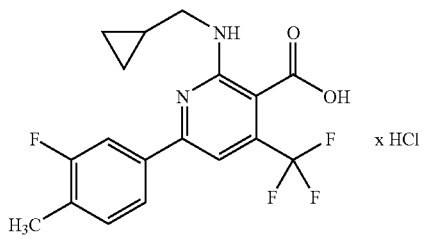

1.33 ml of a 2M sodium hydroxide solution were added to 84 mg (0.201 mmol) of Example 44A in 2.6 ml of ethanol. The mixture was stirred at 80° C. overnight. For work-up, the reaction mixture was adjusted to pH 1 using 1N hydrochloric acid. After removal of the volatile components on a rotary evaporator, the crude product was purified by preparative HPLC (mobile phase: acetonitrile/water, gradient 10:90→90:10). This gave 14 mg (17% of theory) of the target compound.

LC-MS (method 6): $R_t$=1.53 min; MS (ESIpos): m/z=369 [M+H]$^+$.

$^1$H-NMR (400 MHz, DMSO-d$_6$): δ [ppm]=0.26-0.30 (m, 2H), 0.43-0.48 (m, 2H), 1.16-1.20 (m, 1H), 2.30 (s, 3H), 3.37 (d, 2H), 7.14 (s, 1H), 7.39-7.43 (m, 2H), 7.90 (s, 1H), 7.90 (s, 1H), 7.92 (2, 1H), 13.92 (sbr, 1H).

Example 45

6-(3,5-Difluorophenyl)-2-ethoxy-4-(trifluoromethyl)nicotinic acid

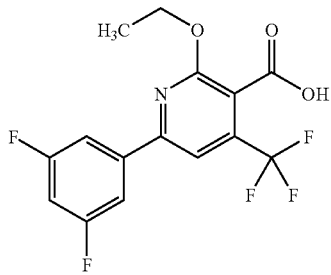

20 mg (0.427 mmol) of ethanol and 34 mg (0.853 mmol) of sodium hydride (60% strength dispersion in mineral oil) were initially charged in 3 ml of tetrahydrofuran. The reaction mixture was stirred at room temperature for 30 minutes. 100 mg (0.284 mol) of Example 46A in 2 ml of tetrahydrofuran were then added. The mixture was stirred at reflux overnight. For work-up, the reaction mixture was adjusted to pH 1 using 1N hydrochloric acid and the product was purified by preparative HPLC (mobile phase: acetonitrile/water, gradient 10:90→90:10). This gave 22 mg (22% of theory) of the target compound.

LC-MS (method 2): $R_t$=2.24 min; MS (ESIpos): m/z=348 [M+H]$^+$.

$^1$H-NMR (400 MHz, DMSO-d$_6$): δ [ppm]=1.38 (t, 3H), 4.56 (q, 2H), 7.42 (t, 1H), 7.96-7.99 (m, 2H), 8.05 (s, 1H), 13.98 (sbr, 1H).

Example 46

2-(Cyclopentylthio)-6-(3,5-difluorophenyl)-4-(trifluoromethyl)nicotinic acid

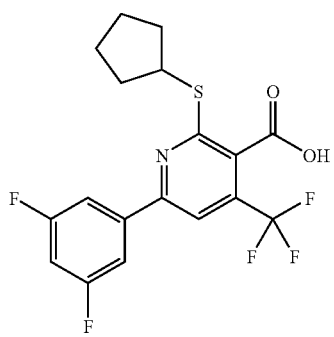

44 mg (0.424 mmol) of cyclopentylmercaptan and 17 mg (0.427 mmol) of sodium hydride (60% strength dispersion in mineral oil) were initially charged in 5 ml of tetrahydrofuran. The reaction mixture was stirred at room temperature for 60 minutes. 100 mg (0.284 mol) of Example 46A were then added as a solution in 2 ml of tetrahydrofuran. The mixture was stirred at reflux overnight. For work-up, the volatile components were removed on a rotary evaporator, the crude product was taken up in ethyl acetate/water and the mixture was adjusted to pH 1 using 1N hydrochloric acid and extracted with ethyl acetate. The combined organic phases were washed successively with saturated aqueous sodium chloride solution, dried over magnesium sulfate and concentrated under reduced pressure. The crude product was purified by preparative HPLC (mobile phase: acetonitrile/water, gradient 10:90→90:10). This gave 33 mg (29% of theory) of the target compound.

LC-MS (method 2): $R_t$=2.58 min; MS (ESIpos): m/z=404 [M+H]$^+$.

$^1$H-NMR (400 MHz, DMSO-d$_6$): δ [ppm]=1.55-1.72 (m, 6H), 2.17-2.22 (m, 2H), 4.04-4.11 (m, 1H), 7.32 (t, 1H), 7.84 (s, 1H), 7.86-7.88 (m, 2H).

Example 47

6-(3-Fluoro-4-methylphenyl)-2-[(2-methoxyethyl)(methyl)amino]-4-(trifluoromethyl)nicotinic acid hydrochloride

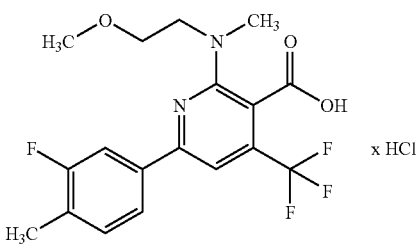

0.75 ml (1.499 mmol) of a 2M aqueous sodium hydroxide solution was added to a solution of 30 mg (0.075 mmol) of Example 45A in 1.5 ml of ethanol. The reaction mixture was stirred at 80° C. liar 30 h. The reaction was checked, showing incomplete conversion. Thus, another 0.75 ml (1.499 mmol) of a 2M aqueous potassium carbonate solution was added. The mixture was stirred at 90° C. overnight. For work-up, the ethanol was distilled off under reduced pressure and the reaction mixture was adjusted to pH 1 using 1N hydrochloric acid. The crystals formed were removed by filtration, washed with water and dried under high vacuum. This gave 21 mg (66% of theory) of the target compound.

LC-MS (method 7): $R_t$=2.55 min; MS (ESIpos): m/z=387 [M+H]$^+$–HCl.

$^1$H-NMR (400 MHz, DMSO-d$_6$): δ [ppm]=2.30 (s, 3H), 3.12 (s, 3H), 3.26 (s, 3H), 3.61 (t, 2H), 3.78 (t, 3H), 7.42 (t, 1H), 7.53 (s, 1H), 7.87 (s, 1H), 7.90 (s, 1H), 13.86 (sbr, 1H).

Example 48

2-(Cyclopentylamino)-6-(3,5-difluorophenyl)-4-(trifluoromethyl)nicotinic acid hydrochloride

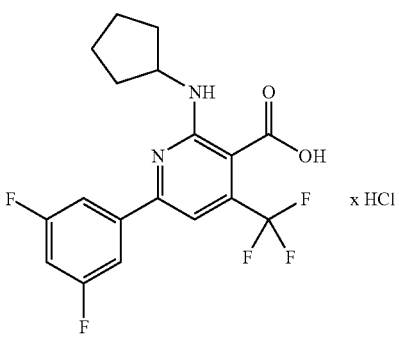

2.65 ml (5.30 mmol) of a 2M aqueous sodium hydroxide solution were added to a solution of 53 mg (0.132 mmol) of Example 47A in 2.6 ml of ethanol. The reaction mixture was stirred at 90° C. for 4 h and at room temperature for 72 h. The reaction was checked, showing only incomplete conversion. Thus, another 1.3 ml (2.60 mmol) of a 2M aqueous sodium hydroxide solution were added. The mixture was stirred at 90° C. for 2 h. For work-up, the reaction mixture was adjusted to pH 1 using 1N hydrochloric acid. After removal of the volatile components on a rotary evaporator, the crude product was purified by preparative HPLC (mobile phase: acetonitrile/water, gradient 90:10). This gave 31 mg (55% of theory) of the target compound.

LC-MS (method 6): $R_t$=1.57 min; MS (ESIpos): m/z=387 [M+H]$^+$–HCl.

$^1$H-NMR (400 MHz, DMSO-d$_6$): δ [ppm]=1.48-1.72 (m, 6H), 2.01-2.07 (m, 2H), 4.43 (m, 1H), 6.91 (sbr, 1H), 7.38 (t, 1H), 7.54 (s, 1H), 7.88-7.92 (m, 2H), 14.06 (sbr, 1H).

Example 49

6-(3,5-Difluorophenyl)-2-(3-methylbutoxy)-4-(trifluoromethyl)nicotinic acid

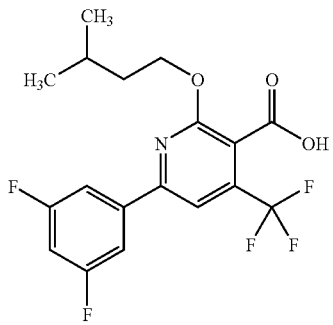

37 mg (0.427 mmol) of 3-methylbutanol and 37 mg (0.427 mmol) of sodium hydride (60% strength dispersion in mineral oil) were initially charged in 3 ml of tetrahydrofuran. The reaction mixture was stirred at room temperature for 30 minutes. 100 mg (0.284 mol) of Example 47A were then added as a solution in 2 ml of tetrahydrofuran. The mixture was stirred at reflux temperature overnight. For work-up, the reaction mixture was adjusted to pH 1 using 1N hydrochloric acid and the product was purified by preparative HPLC (mobile phase: acetonitrile/water, gradient 10:90→90:10). This gave 4 mg (4% of theory) of the target compound.

LC-MS (method 2): $R_t$=2.60 min; MS (ESIpos): m/z=390 [M+H]$^+$ $^1$H-NMR (400 MHz, DMSO-d$_6$): δ [ppm]=0.94 (d, 6H), 1.65 (dd, 2H), 1.75-1.82 (m, 1H), 4.55 (t, 1H), 7.41 (t, 1H), 7.95-7.98 (m, 2H), 8.05 (s, 1H), 13.96 (sbr, 1H).

Example 50

2-Ethyl-4-isobutyl-6-(4-methylphenyl)nicotinic acid

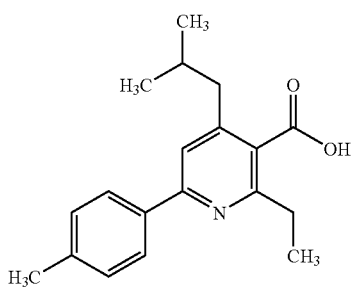

83 mg (0.267 mmol) of Example 31A were taken up in 4.0 ml of ethanol, and 2.00 ml (4.00 mmol) of a 2M aqueous potassium hydroxide solution were added. The mixture was then reacted at 170° C. (pressure-controlled at 18 bar) in a single mode microwave oven (Emrys Optimizer) for 45 min. The mixture was concentrated, taken up in 10 ml of water and acidified with 1N hydrochloric acid. The mixture was extracted with ethyl acetate (3×10 ml), the combined organic phases were dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 45 mg (57% of theory) of the target compound.

LC-MS (method 1): $R_t$=1.95 min; MS (ESIpos): m/z=298 [M+H]$^+$.

$^1$H-NMR (400 MHz, DMSO-d$_6$): δ [ppm]=0.88 (d, 6H), 1.27 (t, 3H), 1.97 (sept, 1H), 2.36 (s, 3H), 2.80 (q, 2H), 7.30 (d, 2H), 7.63 (s, 1H), 8.01 (d, 2H), 13.45 (sbr, 1H).

Example 51

6-(4-Chlorophenyl)-2-ethyl-4-isobutyl-nicotinic acid

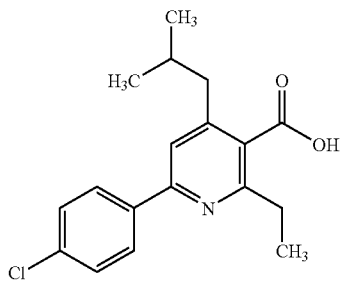

146 mg (0.440 mmol) of Example 32A were taken up in 4.8 ml of ethanol, and 2.40 ml (4.80 mmol) of a 2M aqueous potassium hydroxide solution were added. The mixture was then reacted at 170° C. (pressure-controlled at 18 bar) in a single mode microwave oven (Emrys Optimizer) for 45 min. The mixture was concentrated, taken up in 10 ml of water and acidified with 1N hydrochloric acid. The mixture was extracted with ethyl acetate (3×10 ml). The combined organic phases were then dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 62 mg (44% of theory) of the target compound.

LC-MS (method 1): $R_t$=2.52 min; MS (ESIpos): m/z=318 [M+H]$^+$.

$^1$H-NMR (400 MHz, DMSO-d$_6$): δ [ppm]=0.88 (d, 6H), 1.28 (t, 3H), 1.98 (sept, 1H), 2.56 (d, 2H), 2.81 (q, 2H), 7.56 (d, 2H), 7.73 (s, 1H), 8.15 (d, 2H), 13.53 (sbr, 1H).

Example 52

6-(4-Chlorophenyl)-4-isobutyl-5-methyl-2-(trifluoromethyl)nicotinic acid

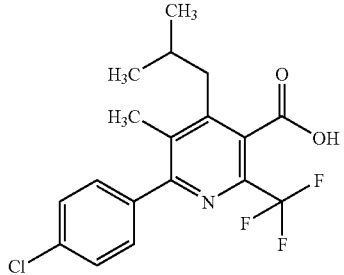

52 mg (0.124 mmol) of Example 36A were taken up in 1.8 ml of ethanol, and 0.31 ml (0.618 mmol) of a 2M aqueous potassium hydroxide solution was added. The mixture was then reacted at 160-180° C. in a single mode microwave oven (Emrys Optimizer) for 90 min. The mixture was concentrated, taken up in 10 ml of water and acidified with 1N hydrochloric acid. The mixture was extracted with ethyl acetate (3×10 ml). The combined organic phases were then dried with magnesium sulfate and the solvent was removed on a rotary evaporator. The crude product was purified by preparative HPLC (mobile phase: acetonitrile/water with 0.1% formic acid, gradient 20:80→95:5). Drying under high vacuum gave 6 mg (13% of theory) of the target compound.

LC-MS (method 1): $R_t$=2.98 min; MS (ESIpos): m/z=372 [M+H]$^+$.

$^1$H-NMR (400 MHz, CDCl$_3$): δ [ppm]=0.97 (d, 6H), 2.05 (sept, 1H), 2.36 (s, 3H), 2.76 (d, 2H), 7.45 (s, 4H).

Example 53

2-(Diethylamino)-6-(3,5-difluorophenyl)-4-(trifluoromethyl)nicotinic acid hydrochloride

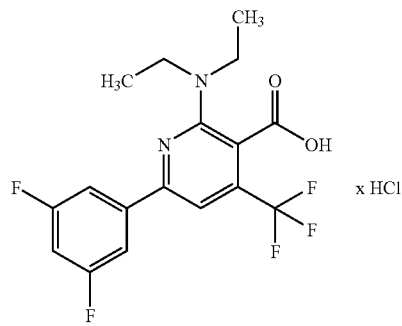

20 mg (0.052 mmol) of Example 50A were taken up in 1 ml of ethanol, and 0.51 ml (1.030 mmol) of a 2M aqueous sodium hydroxide solution was added. The mixture was stirred at 90° C. overnight. 42 mg (1.040 mmol) of sodium hydroxide were then added. The reaction mixture was then heated at 90° C. for 4 h. The mixture was then reacted at 150° C. in a single mode microwave oven (Emrys Optimizer) for 55 min. The mixture was acidified with 1N hydrochloric acid, concentrated and taken up in ethyl acetate. The mixture was then washed with water and saturated aqueous sodium chloride solution. After drying with magnesium sulfate the solvent was removed on a rotary evaporator. The residue was dried under high vacuum. This gave 15 mg (70% of theory) of the target compound.

LC-MS (method 1): $R_t$=2.81 min; MS (ESIpos): m/z=375 [M+H]$^+$–HCl.

$^1$H-NMR (400 MHz, CDCl$_3$): δ [ppm]=1.19 (t, 6H), 3.53 (q, 4H), 7.39 (t, 1H), 7.64 (s, 1H), 7.85-7.89 (m, 2H), 13.98 (sbr, 1H).

Example 54

6-(4-Chloro-3-fluorophenyl)-2-(3,3-dimethylbutoxy)-4-(trifluoromethyl)nicotinic acid

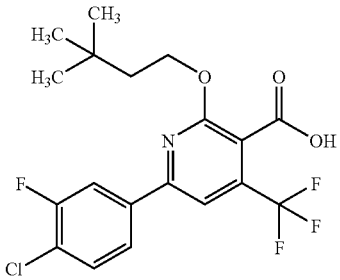

37 mg (0.357 mmol) of 3,3-dimethyl-1-butanol and 29 mg (0.713 mmol) of sodium hydride (60% strength dispersion in mineral oil) were initially charged in 4 ml of tetrahydrofuran. The reaction mixture was stirred at room temperature for 45 minutes. 100 mg (0.238 mol) of Example 49A were then added as a solution in 2 ml of tetrahydrofuran. The mixture was stirred at reflux overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 8 mg (7% of theory) of the target compound.

LC-MS (method 2): $R_t$=2.77 min; MS (ESIpos): m/z=420 [M+H]$^+$–HCl.

$^1$H-NMR (400 MHz, CDCl$_3$): δ [ppm]=0.98 (s, 9H), 1.68 (t, 2H), 4.57 (t, 2H), 7.76 (t, 1H), 8.01 (s, 1H), 8.10 (d, 1H), 8.26 (d, 1H), 13.92 (sbr, 1H).

Example 55

6-(3,4-Dichlorophenyl)-2-(3-methylbutoxy)-4-(trifluoromethyl)nicotinic acid

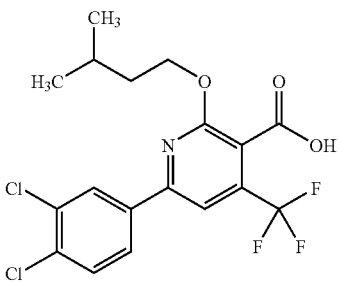

29 mg (0.221 mmol) of 3-methylbutanol and 27 mg (0.663 mmol) of sodium hydride (60% strength dispersion in mineral oil) were initially charged in 4 ml of tetrahydrofuran. The reaction mixture was stirred at room temperature for 45 minutes. 100 mg (0.221 mol) of Example 48A were then added as a solution in 2 ml of tetrahydrofuran. The mixture was stirred at reflux overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 47 mg (51% of theory) of the target compound.

LC-MS (method 2): $R_t$=2.80 min; MS (ESIpos): m/z=424 [M+H]$^+$.

$^1$H-NMR (400 MHz, CDCl$_3$): δ [ppm]=0.94 (d, 6H), 1.65 (m, 2H), 1.75-1.82 (m, 1H), 4.54 (t, 2H), 7.80 (d, 1H), 8.04 (s, 1H), 8.21 (d, 1H), 8.47 (s, 1H), 13.93 (sbr, 1H).

Example 56

6-(4-Chloro-3-fluorophenyl)-2-(3-methylbutoxy)-4-(trifluoromethyl)nicotinic acid

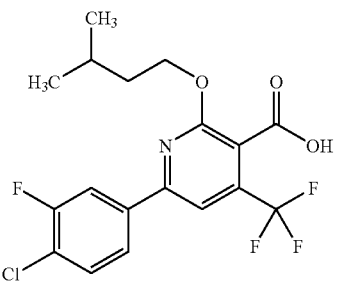

32 mg (0.357 mmol) of 3-methylbutanol and 29 mg (0.713 mmol) of sodium hydride (60% strength dispersion in mineral oil) were initially charged in 3 ml of tetrahydrofuran. The reaction mixture was stirred at room temperature for 45 minutes. 100 mg (0.238 mol) of Example 49A were then added as a solution in 2 ml of tetrahydrofuran. The mixture was stirred at reflux overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 8 mg (8% of theory) of the target compound.

LC-MS (method 2): $R_t$=2.70 min; MS (ESIpos): m/z=406 [M+H]$^+$.

$^1$H-NMR (400 MHz, CDCl$_3$): δ [ppm]=0.94 (d, 6H), 1.65 (m, 2H), 1.75-1.82 (m, 1H), 4.54 (t, 2H), 7.76 (t, 1H), 8.00 (s, 1H), 8.10 (d, 1H), 8.26 (d, 1H), 13.89 (sbr, 1H).

Example 57

6-(3,4-Dichlorophenyl)-2-(3,3-dimethylbutoxy)-4-(trifluoromethyl)nicotinic acid

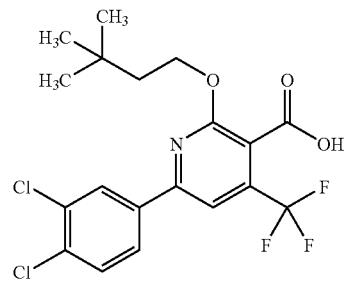

34 mg (0.332 mmol) of 3,3-dimethylbutanol and 27 mg (0.663 mmol) of sodium hydride (60% strength dispersion in mineral oil) were initially charged in 3 ml of tetrahydrofuran. The reaction mixture was stirred at room temperature for 45 minutes. 100 mg (0.221 mol) of Example 48A were then added as a solution in 2 ml of tetrahydrofuran. The mixture was stirred at reflux overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 20 mg (21% of theory) of the target compound.

LC-MS (method 2): $R_t$=2.93 min; MS (ESIpos): m/z=338 [M+H]$^+$.

$^1$H-NMR (400 MHz, CDCl$_3$): δ [ppm]=0.99 (s, 9H), 1.60 (t, 2H), 4.43 (t, 2H), 7.65 (s, 1H), 7.72 (d, 1H), 8.09 (dd, 1H), 8.35 (s, 1H).

Example 58

6-(3,4-Dichlorophenyl)-2-ethoxy-4-(trifluoromethyl)nicotinic acid

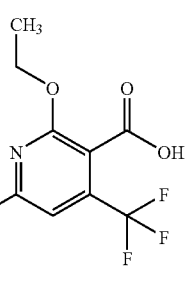

15 mg (0.332 mmol) of ethanol and 26 mg (0.663 mmol) of sodium hydride (60% strength dispersion in mineral oil) were initially charged in 4 ml of tetrahydrofuran. The reaction mixture was stirred at room temperature for 45 minutes. 100 mg (0.221 mol) of Example 48A were then added as a solution in 2 ml of tetrahydrofuran. The mixture was stirred at 80° C. overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 18 mg (22% of theory) of the target compound.

LC-MS (method 1): $R_t$=3.12 min; MS (ESIpos): m/z=380 [M+H]$^+$.

$^1$H-NMR (400 MHz, CDCl$_3$): δ [ppm]=1.37 (t, 3H), 4.55 (q, 2H), 7.80 (d, 1H), 8.05 (s, 1H), 8.21 (d, 1H), 8.47 (s, 1H), 13.97 (sbr, 1H).

Example 59

2-(3-Methylbutoxy)-4-(trifluoromethyl)-6-[4-(trifluoromethyl)phenyl]nicotinic acid

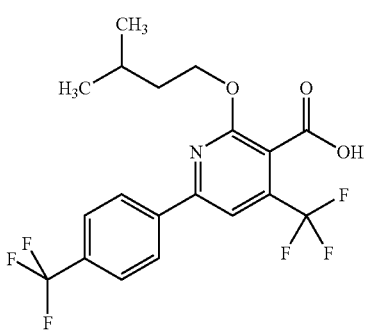

39 mg (0.440 mmol) of 3-methyl-1-butanol and 36 mg (0.880 mmol) of sodium hydride (60% strength dispersion in mineral oil) were initially charged in 5 ml of tetrahydrofuran. The reaction mixture was stirred at room temperature for 45 minutes. 150 mg (0.293 mol) of Example 51A were then added as a solution in 2 ml of tetrahydrofuran. The mixture was stirred at 80° C. overnight and reacted at room temperature over the weekend. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 51 mg (41% of theory) of the target compound.

LC-MS (method 1): $R_t$=3.27 min; MS (ESIpos): m/z=422 [M+H]$^+$.

$^1$H-NMR (400 MHz, CDCl$_3$): δ [ppm]=0.94 (d, 1H), 1.66 (dd, 1H), 1.74-1.83 (m, 1H), 4.56 (t, 1H), 7.90 (d, 2H), 8.02 (s, 1H), 8.41 (d, 2H), 13.95 (sbr, 1H)

Example 60

2-Ethoxy-4-(trifluoromethyl)-6-[4-(trifluoromethyl)phenyl]nicotinic acid

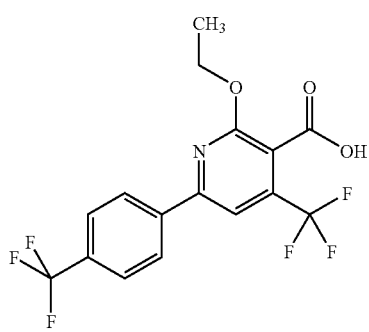

20 mg (0.440 mmol) of ethanol and 36 mg (0.880 mmol) of sodium hydride (60% strength dispersion in mineral oil) were initially charged in 5 ml of tetrahydrofuran. The reaction mixture was stirred at room temperature for 45 minutes. 150 mg (0.293 mol) of Example 51A were then added as a solution in 2 ml of tetrahydrofuran. The mixture was stirred at 80° C. overnight and reacted at room temperature over the weekend. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 32 mg (29% of theory) of the target compound.

LC-MS (method 7): $R_t$=2.63 min; MS (ESIpos): m/z=380 [M+H]$^+$.

$^1$H-NMR (400 MHz, CDCl$_3$): δ [ppm]=1.38 (t, 3H), 4.57 (q, 2H), 7.90 (d, 2H), 8.03 (s, 1H), 8.42 (d, 2H), 13.98 (sbr, 1H).

Example 61

2-(3,3-Dimethylbutoxy)-4-(trifluoromethyl)-6-[4-(trifluoromethyl)phenyl]nicotinic acid

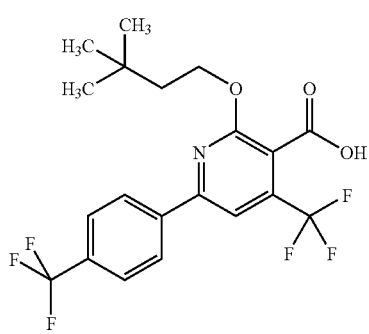

45 mg (0.440 mmol) of 3,3-dimethyl-1-butanol and 35 mg (0.880 mmol) of sodium hydride (60% strength dispersion in mineral oil) were initially charged in 5 ml of tetrahydrofuran. The reaction mixture was stirred at room temperature for 45 minutes. 150 mg (0.293 mol) of Example 51A were theft added as a solution in 2 ml of tetrahydrofuran. The mixture was stirred at 80° C. overnight and reacted at room temperature over the weekend. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 34 mg (26% of theory) of the target compound.

LC-MS (method 1): $R_t$=3.35 min; MS (ESIpos): m/z=436 [M+H]$^+$.

$^1$H-NMR (400 MHz, CDCl$_3$): δ [ppm]=0.98 (s, 9H), 1.70 (t, 2H), 4.59 (t, 2H), 7.90 (d, 2H), 8.02 (s, 1H), 8.42 (d, 2H), 13.95 (sbr, 1H).

Example 62

6-(4-Chlorophenyl)-2-(3-methoxy-1-methylpropoxy)-4-(trifluoromethyl)nicotinic acid

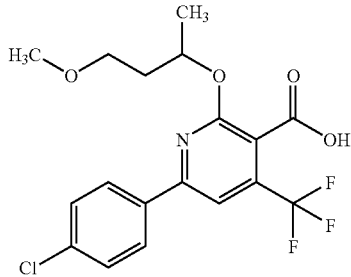

0.846 ml (1.728 mmol) of a 2M aqueous sodium hydroxide solution were added to a solution of 44 mg (0.428 mmol) of Example 52A in 2 ml of ethanol. The reaction mixture was stirred at 80° C. for 4 h. For work-up, the ethanol was distilled off under reduced pressure and the reaction mixture was adjusted to pH 1 using 1N hydrochloric acid and extracted repeatedly with dichloromethane. The organic phase was dried over sodium sulfate. Removal of the volatile components on a rotary evaporator gave 24 mg (68% of theory) of the target compound.

LC-MS (method 1): $R_t$=2.94 min; MS (ESIpos): m/z=404 [M+H]$^+$.

$^1$H-NMR (400 MHz, CDCl$_3$): δ [ppm]=1.38 (d, 3H), 1.86-1.96 (m, 2H), 3.19 (s, 3H), 3.43 (t, 2H), 5.42-5.48 (m, 1H), 7.60 (d, 2H), 7.92 (s, 1H), 8.22 (d, 2H), 13.82 (sbr, 1H).

Example 63

6-(4-Chlorophenyl)-2-[(1,4-dimethylpentyl)oxy]-4-(trifluoromethyl)nicotinic acid

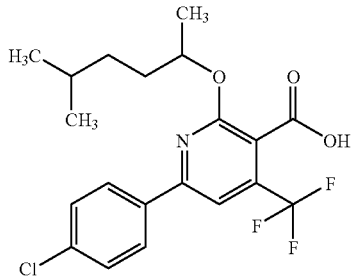

50 mg (0.428 mmol) of 5-methyl-2-hexanol and 35 mg (0.857 mmol) of sodium hydride (60% strength dispersion in mineral oil) were initially charged in 3 ml of tetrahydrofuran. The reaction mixture was stirred at room temperature for 30 minutes. 100 mg (0.286 mol) of Example 24A were then added as a solution in 2 ml of tetrahydrofuran. The mixture was stirred at 80° C. overnight. The solvent was removed on a rotary evaporator and the mixture was purified by preparative HPLC (mobile phase: acetonitrile/water, gradient 10:90→90:10). This gave 55 mg (46% of theory) of the target compound.

LC-MS (method 1): $R_t$=3.41 min; MS (ESIpos): m/z=416 [M+H]$^+$.

$^1$H-NMR (400 MHz, CDCl$_3$): δ [ppm]=0.85 (d, 3H), 0.86 (d, 3H), 1.16-1.38 (m, 5H), 1.48-1.59 (m, 2H), 1.66-1.75 (m, 1H), 5.19-5.25 (m, 1H), 7.52-7.54 (m, 3H), 8.09 (d, 1H).

Example 64

6-(4-Chlorophenyl)-2-(3,3-dimethylbutoxy)-4-(trifluoromethyl)nicotinic acid

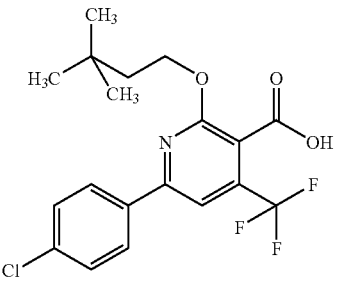

43 mg (0.428 mmol) of 3,3-dimethyl-1-butanol and 35 mg (0.857 mmol) of sodium hydride (60% strength dispersion in mineral oil) were initially charged in 3 ml of tetrahydrofuran. The reaction mixture was stirred at room temperature for 30 minutes. 100 mg (0.286 mol) of Example 24A were then added as a solution in 2 ml of tetrahydrofuran. The mixture was stirred at 80° C. overnight. The solvent was removed on a rotary evaporator and the mixture was purified by preparative HPLC (mobile phase: acetonitrile/water, gradient 10:90→90:10). This gave 30 mg (26% of theory) of the target compound.

LC-MS (method 1): $R_t$=3.38 min; MS (ESIpos): m/z=402 [M+H]$^+$.

$^1$H-NMR (400 MHz, CDCl$_3$): δ [ppm]=0.98 (s, 9H), 1.65 (t, 2H), 4.42 (t, 2H), 7.52-7.55 (m, 3H), 8.11 (d, 1H).

Example 65

6-(4-Chlorophenyl)-4-(1-methylethoxy)-2-(1-methylethyl)nicotinic acid

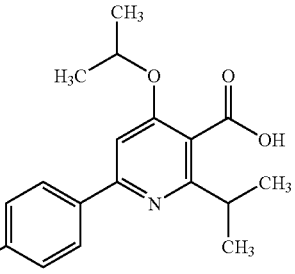

67 mg (0.158 mmol) of Example 58A, 11.0 mg (0.174 mmol) of ammonium formate and 16.8 mg of palladium (10% on carbon) were taken up in 4 ml methanol, 0.1 ml of water was added and the mixture was stirred at room temperature overnight. The reaction mixture was filtered through kieselguhr and the filtrate was concentrated on a rotary evaporator. The residue was purified by preparative HPLC (mobile phase: acetonitrile/water, gradient 10:90→90:10). After concentration of the product fractions, water and ethyl acetate were added, the mixture was adjusted with 1N hydrochloric acid to pH 2 and the organic phase was separated off. The mixture was washed with water and saturated aqueous sodium chloride solution, dried over magnesium sulfate and concentrated, and the residue was dried under high vacuum. This gave 8 mg (15% of theory) of the target compound.

LC-MS (method 2): $R_t$=2.02 min; MS (ESIpos): m/z=334 [M+H]$^+$.

$^1$H-NMR (400 MHz, DMSO-d$_6$): δ [ppm]=1.24 (d, 6H), 1.30 (d, 6H), 3.03 (sept, 1H), 5.00 (sept, 1H), 7.48 (s, 1H), 7.56 (d, 2H), 8.18 (d, 2H).

Example 66

6-(4-Bromophenyl)-2-(1-methylethoxy)-4-(trifluoromethyl)nicotinic acid

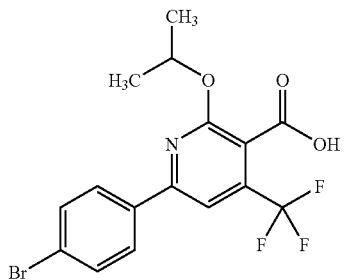

21 mg (0.342 mmol) of 2-propanol and 28 mg (0.684 mmol) of sodium hydride (60% strength dispersion in mineral oil) were initially charged in 2 ml of tetrahydrofuran. The reaction mixture was stirred at room temperature for 45 minutes. 90 mg (0.228 mol) of Example 59A were then added as a solution in 2 ml of tetrahydrofuran. The mixture was stirred at 80° C. overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 24 mg (25% of theory) of the target compound.

LC-MS (method 1): $R_t$=3.04 min; MS (ESIpos): m/z=404 [M+H]$^+$.

$^1$H-NMR (400 MHz, CDCl$_3$): δ [ppm]=1.36 (d, 6H), 5.43-5.51 (m, 1H), 7.74 (d, 2H), 7.90 (s, 1H), 8.14 (d, 2H).

Example 67

6-(4-Bromophenyl)-2-(3,3-dimethylbutoxy)-4-(trifluoromethyl)nicotinic acid

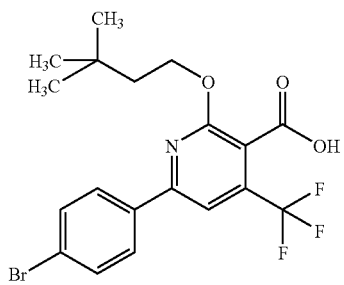

35 mg (0.342 mmol) of 3,3-dimethylbutanol and 28 mg (0.684 mmol) of sodium hydride (60% strength dispersion in mineral oil) were initially charged in 2 ml of tetrahydrofuran. The reaction mixture was stirred at room temperature for 45 minutes. 90 mg (0.228 mol) of Example 59A were then added as a solution in 2 ml of tetrahydrofuran. The mixture was stirred at 80° C. overnight. For work-up, the reaction mixture was adjusted to pH 1 using 1N hydrochloric acid, the solvent was removed on a rotary evaporator and the product was purified by preparative HPLC (mobile phase: acetonitrile/water, gradient 10:90→90:10). This gave 36 mg (36% of theory) of the target compound.

LC-MS (method 1): $R_t$=3.364 min; MS (ESIpos): m/z=446 [M+H]$^+$.

$^1$H-NMR (400 MHz, CDCl$_3$): δ [ppm]=0.98 (s, 9H), 1.68 (t, 2H), 4.56 (t, 2H), 7.74 (d, 2H), 7.92 (s, 1H), 8.16 (d, 2H), 13.88 (sbr, 1H).

Example 68

6-(4-Chlorophenyl)-2-ethoxy-4-(trifluoromethyl)nicotinic acid

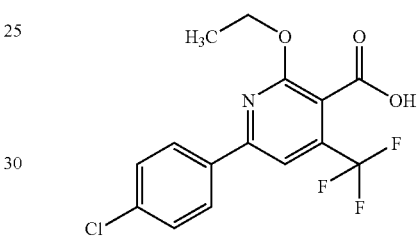

20 mg (0.428 mmol) of ethanol and 34 mg (0.817 mmol) of sodium hydride (60% strength dispersion in mineral oil) were initially charged in 2 ml of tetrahydrofuran. The reaction mixture was stirred at room temperature for 30 minutes. 100 mg (0.286 mol) of Example 24A were then added as a solution in 2 ml of tetrahydrofuran. The mixture was stirred at 80° C. overnight. The reaction mixture was purified directly by preparative HPLC (mobile phase: acetonitrile/water, gradient 10:90→90:10). This gave 7 mg (8% of theory) of the target compound.

LC-MS (method 2): $R_t$=2.31 min; MS (ESIpos): m/z=346 [M+H]$^+$.

$^1$H-NMR (400 MHz, CDCl$_3$): δ [ppm]=1.34 (t, 3H), 1.92 (q, 2H), 7.55 (d, 2H), 7.70 (sbr, 1H), 8.16 (d, 2H).

Example 69

6-(4-Chlorophenyl)-4-[(1-methylethyl)amino]-2-(trifluoromethyl)nicotinic acid

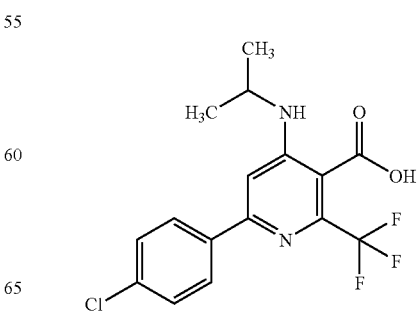

56 mg (0.145 mmol) of Example 64A and 725 µl (1.448 mmol) of a 2N aqueous potassium hydroxide solution were initially charged in 3 ml of ethanol and reacted at 160° C. in a single mode microwave oven (Emrys Optimizer) for 30 min. The volatile components were removed on a rotary evaporator. The crude product was then purified by preparative HPLC (mobile phase: acetonitrile/water, gradient 10:90→90:10). This gave 20 mg (39% of theory) of the target compound.

LC-MS (method 1): $R_t$=3.04 min; MS (ESIpos): m/z=359 [M+H]$^+$.

$^1$H-NMR (400 MHz, DMSO-d$_6$): δ [ppm]=1.22 (d, 6H), 4.09 (mz, 1H), 6.52 (d, 1H), 7.38 (s, 1H), 7.57 (d, 2H), 8.15 (d, 2H), 13.92 (sbr, 1H).

Example 70

6-(4-(Chlorophenyl)-4-ethoxy-2-(1-methylethyl)nicotinic acid

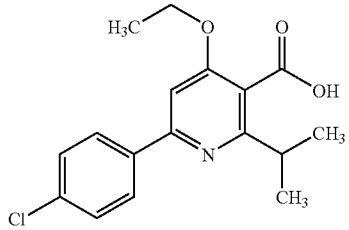

1.77 g (5.31 mmol) of Example 68A were dissolved in 50 ml of dioxane. 1.49 g (26.5 mmol) of powdered potassium hydroxide were then added, and the mixture was then stirred at reflux temperature for 2 h. The volatile components were removed on a rotary evaporator. The residue was then taken up in water and acidified with 1N hydrochloric acid, and the aqueous phase was extracted with ethyl acetate (2×). The combined organic phases were dried with magnesium sulfate, the solvent was removed on a rotary evaporator and the product was crystallized from n-pentane. The crude product obtained in this manner still contained impurities. Thus, it was finally purified by preparative HPLC (mobile phase: acetonitrile/water, gradient 10:90→90:10). This gave 1.46 g (86% of theory) of the target compound.

LC-MS (method 6): $R_t$=1.21 min; MS (ESIpos): m/z=320 [M+H]$^+$.

$^1$H-NMR (400 MHz, DMSO-d$_6$): δ [ppm]=1.25 (d, 6H), 1.38 (t, 3H), 3.05 (sept, 1H), 4.29 (q, 2H), 7.48 (s, 1H), 7.57 (d. 2H), 8.19 (d, 2H), 13.23 (sbr, 1H).

Example 71

6-(4-Chlorophenyl)-4-ethoxy-2-(1-methylethyl)nicotinic acid sodium salt

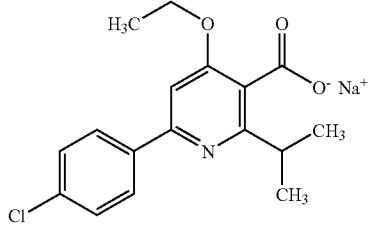

885 mg (2.77 mmol) of Example 68A were taken up in 25 ml of ethanol, and 2.67 ml (2.77 mmol) of a 1M aqueous sodium hydroxide solution were added. After two hours of stirring at room temperature, the volatile components were removed on a rotary evaporator. The residue was then taken up in 20 ml toluene/methanol (1/1) and concentrated again. This operation was repeated two more times. The residue was then dried under high vacuum overnight. This gave 924 mg (98% of theory) of the target compound as a solid.

$^1$H-NMR (400 MHz, DMSO-d$_6$): δ [ppm]=1.19 (d, 6H), 1.30 (t, 3H), 3.24 (sept, 1H), 4.13 (q, 2H), 7.22 (s, 1H), 7.50 (d, 2H), 8.11 (d, 2H).

Example 72

6-(4-Chlorophenyl)-2-(1-methylethyl)-4-(trifluoromethyl)nicotinic acid

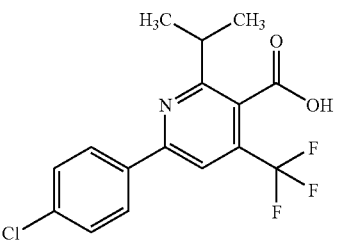

34 mg (0.095 mmol) of Example 69A were dissolved in 2 ml of dioxane, 37 mg (0.67 mmol) of potassium hydroxide were added and the mixture was reacted at reflux temperature overnight. The volatile components were then removed on a rotary evaporator. The mixture was taken up in 5 ml of water and acidified with 5 ml of 1N hydrochloric acid. After extraction with ethyl acetate (2×), the combined organic phases were dried with magnesium sulfate. The solvent was removed on a rotary evaporator. The product was then crystallized from n-pentane and isolated by filtration. This gave 25 mg (77% of theory) of the target compound.

LC-MS (method 2): $R_t$=2.46 min; MS (ESIpos): m/z=344 [M+H]$^+$.

$^1$H-NMR (400 MHz, DMSO-d$_6$): δ [ppm]=1.32 (d, 6H), 3.25 (sept, 1H), 7.62 (d, 2H), 8.20 (s, 1H), 8.28 (d, 2H).

Example 73

6-(4-Chlorophenyl)-4-ethoxy-2-ethylnicotinic acid sodium salt

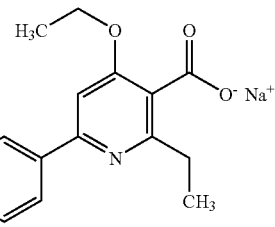

78 mg (0.244 mmol) of Example 71A were dissolved in 5 ml of dioxane, 68 mg (1.22 mmol) of potassium hydroxide were added and the mixture was reacted at reflux temperature overnight. The volatile components were then removed on a rotary evaporator. The mixture was taken up in 5 ml of water and acidified with 5 ml of 1N hydrochloric acid. After extraction with ethyl acetate (2×), the combined organic phases were dried with magnesium sulfate. The solvent was removed on a rotary evaporator. The product was then crystallized from n-pentane. Since the precipitate still contained impurities, it was dissolved as a salt by addition of 1N aqueous sodium hydroxide solution and finally purified by preparative HPLC (mobile phase: acetonitrile/water, gradient 10:90→90:10). This gave 5 mg (6% of theory) of the target compound.

LC-MS (method 1): R$_t$=1.41 min; MS (ESIpos): m/z=306 [M−Na+2H]$^+$ $^1$H-NMR (400 MHz, DMSO-d$_6$): δ [ppm]=1.22 (t, 3H), 1.32 (t, 3H), 2.65-2.68 (2H), 4.22 (q, 2H), 7.37 (s, 1H). 7.53 (d, 2H), 8.14 (d, 2H).

Example 74

6-(4-Chlorophenyl)-2-ethyl-4-(1-methylethoxy)nicotinic acid

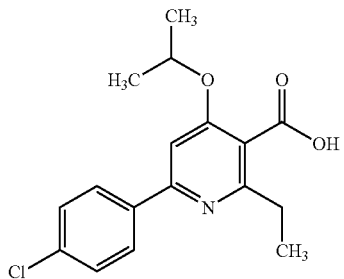

80 mg (0.240 mmol) of Example 72A were dissolved in 5 ml of dioxane, 67 mg (1.20 mmol) of potassium hydroxide were added and the mixture was reacted at reflux temperature overnight. The volatile components were then removed on a rotary evaporator. The mixture was taken up in 5 ml of water and acidified with 5 ml of 1N hydrochloric acid. After extraction with ethyl acetate (2×), the combined organic phases were dried with magnesium sulfate. The solvent was removed on a rotary evaporator. The product was then crystallized from n-pentane. Since the precipitate still contained impurities, the product was purified by preparative HPLC (mobile phase: acetonitrile/water, gradient 10:90→90:10). This gave 7 mg (9% of theory) of the target compound.

LC-MS (method 1): R$_t$=1.53 min; MS (ESIpos): m/z=320 [M+H]$^+$ $^1$H-NMR (400 MHz, DMSO-d$_6$): δ [ppm]=1.24 (t, 3H), 1.30 (d, 6H), 2.70 (q, 2H), 5.01 (sept, 1H), 7.49 (s, 1H), 7.55 (d, 2H), 8.16 (d, 2H), 13.16 (sbr, 1H).

Example 75

2-Ethyl-4-(1-methylethoxy)-6-[4-(trifluoromethyl)phenyl]nicotinic acid

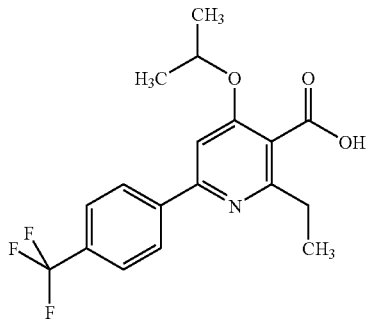

152 mg (0.414 mmol) of Example 74A were dissolved in 5 ml of dioxane, 116 mg (2.07 mmol) of potassium hydroxide were added and the mixture was reacted at reflux temperature overnight. The volatile components were then removed on a rotary evaporator. The mixture was taken up in 5 ml of water and acidified with 5 ml of 1N hydrochloric acid. After extraction with ethyl acetate (2×), the combined organic phases were dried with magnesium sulfate. The solvent was removed on a rotary evaporator. The product was then crystallized from n-pentane. Since the precipitate still contained impurities, the product was finally purified by preparative HPLC (mobile phase: acetonitrile/water, gradient 10:90→90:10). This gave 76 mg (48% of theory) of the target compound.

LC-MS (method 6): R$_t$=1.05 min; MS (ESIpos): m/z=354 [M+H]$^+$.

$^1$H-NMR (400 MHz, DMSO-d$_6$): δ [ppm]=1.26 (t, 3H), 1.31 (d, 6H), 2.73 (q, 2H), 5.04 (sept, 1H), 7.60 (s, 1H), 7.86 (d, 2H), 8.35 (d, 2H), 13.22 (sbr, 1H).

Example 76

2-Ethyl-4-(3-methylbutoxy)-6-[4-(trifluoromethyl)phenyl]nicotinic acid

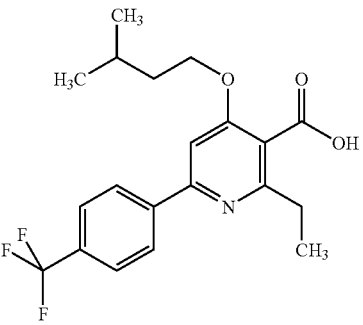

60 mg (0.152 mmol) of Example 75A were dissolved in 3 ml of dioxane, 43 mg (0.759 mmol) of potassium hydroxide were added and the mixture was reacted at reflux temperature overnight. The volatile components were then removed on a rotary evaporator. The mixture was taken up in 5 ml of water and acidified with 5 ml of 1N hydrochloric acid. After extraction with ethyl acetate (2×), the combined organic phases were dried with magnesium sulfate. The solvent was removed on a rotary evaporator. The product was then crystallized from n-pentane. Since the precipitate still contained impurities, the product was finally purified by preparative HPLC (mobile phase: acetonitrile/water, gradient 10:90→90:10). This gave 39 mg (65% of theory) of the target compound.

LC-MS (method 6): R$_t$=1.32 min; MS (ESIpos): m/z=382 [M+H]$^+$.

$^1$H-NMR (400 MHz, DMSO-d$_6$): δ [ppm]=0.94 (d, 6H), 1.26 (t, 3H), 1.63 (mz, 2H), 1.79 (sept, 1H), 2.74 (q, 2H), 4.27 (t, 2H), 7.61 (s, 1H), 7.86 (d, 2H), 8.36 (d, 2H), 13.27 (sbr, 1H).

Example 77

6-(4-Chlorophenyl)-2-isobutyl-4-(trifluoromethyl)nicotinic acid sodium salt

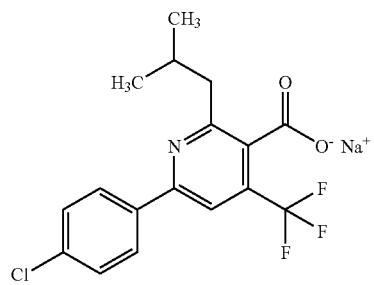

1.15 g (3.14 mmol) of Example 25 were taken up in 15 ml of ethanol, and 3.14 ml (3.14 mmol) of a 1M aqueous sodium hydroxide solution were added. After two hours of stirring at room temperature, the volatile components were removed on a rotary evaporator. The residue was then crystallized from 20 ml toluene/methanol (1/1). The product was then recrystallized from acetone and dried under high vacuum overnight. This gave 940 mg (77% of theory) of the target compound as a solid.

$^1$H-NMR (400 MHz, DMSO-$d_6$): δ [ppm]=0.91 (d, 6H), 2.36 (sept, 1H), 2.76 (d, 2H), 7.54 (d, 2H), 7.83 (s, 1H), 8.14 (d, 2H).

B. Assessment of the Pharmacological Activity

The pharmacological activity of the compounds according to the invention can be demonstrated by the following assays:

B-1: Cellular Transactivation Assay:

a) Test Principle:

A cellular assay is used to identify activators of the peroxisome proliferator-activated receptor alpha (PPAR-alpha).

Since mammalian cells contain different endogenous nuclear receptors which may complicate an unambiguous interpretation of the results, an established chimera system is used in which the ligand binding domain of the human PPARα receptor is fused to the DNA binding domain of the yeast transcription factor GAL4. The resulting GAL4-PPARα chimera is co-transfected and stably expressed in CHO cells having a reporter construct.

b) Cloning:

The GAL4-PPARα expression construct contains the ligand binding domain of PPARα (amino acids 167-468) which is PCR-amplified and cloned into the vector pcDNA3.1. This vector already contains the GAL4 DNA binding domain (amino acids 1-147) of the vector pFC2-dbd (Stratagene). The reporter construct, which contains five copies of the GAL4 binding site upstream of a thymidine kinase promoter, expresses firefly luciferase (*Photinus pyralis*) following activation and binding of GAL4-PPARα.

c) Practice of the Test:

The day before the test, CHO (Chinese hamster ovary) cells which stably express the GAL4-PPARα chimera described above and the luciferase reporter gene construct are plated in medium (Optimem, GIBCO), 2% activated carbon-purified fetal calf serum (Hyclone), 1.35 mM sodium pyruvate (GIBCO), 0.2% sodium bicarbonate (GIBCO) with $1\times10^3$ cells in 96-well microtiter plates and kept in a cell incubator (96% atmospheric humidity, 5% v/v $CO_2$, 37° C.). On the day of the test, the substances to be tested are taken up in the medium mentioned above but without added calf serum) and added to the cells. After a stimulation period of 6 h, the luciferase activity is measured using a video camera. The relative light units measured give, as a function of the substance concentration, a sigmoidal stimulation curve. The $EC_{50}$ values are calculated using the computer programme GraphPad PRISM (Version 3.02).

The $EC_{50}$ values of representative exemplary compounds are listed in the table below:

TABLE

| Example No. | $EC_{50}$ [nM] |
|---|---|
| 2 | 11 |
| 7 | 83 |
| 22 | 100 |
| 34 | 95 |

TABLE-continued

| Example No. | $EC_{50}$ [nM] |
|---|---|
| 42 | 120 |
| 47 | 180 |
| 49 | 42 |
| 51 | 24 |
| 67 | 182 |
| 71 | 86 |
| 77 | 13 |

B-2: Fibrinogen Determination:

To determine the effect on the plasma fibrinogen concentration, male Wistar rats or NMRI mice are treated with the substance to be examined by stomach tube administration or by addition to the feed for a period of 4-9 days. Under terminal anaesthesia, citrate blood is then obtained by heart puncture. The plasma fibrinogen concentrations are determined according to the Clauss method [A. Clauss, *Acta Haematol.* 17, 237-46 (1957)] by measuring the thrombin time using human fibrinogen as standard.

B-3: Description of a Test for Finding Pharmacologically Active Substances which Increase Apoprotein A1 (ApoA1) and HDL Cholesterol (HDL-C) Concentrations in the Serum of Transgenic Mice Transfected with the Human ApoA1 Gene (hApoA1) and/or Lower Serum Triglycerides (TG):

The substances to be examined in vivo for their HDL-C-increasing activity are administered orally to male transgenic hApoA1 mice. One day prior to the start of the experiment, the animals are randomized into groups with the same number of animals, generally n=7-10. Throughout the experiment, the animals have drinking water and feed ad libitum. The substances are administered orally once a day for 7 days. To this end, the test substances are dissolved in a solution of Solutol HS15+ethanol+saline (0.9%) in a ratio of 1+1+8 or in a solution of Solutol HS15+saline (0.9%) in a ratio of 2+8. The dissolved substances are administered in a volume of 10 ml/kg of body weight using a stomach tube. Animals which have been treated in exactly the same manner but have only been given the solvent (10 ml/kg of body weight), without test substance, serve as control group.

Prior to the first administration of substance, a blood sample from each of the mice is taken by puncture of the retroorbital venous plexus, to determine ApoA1, serum cholesterol, HDL-C and serum triglycerides (TG) (zero value). Subsequently, using a stomach tube, the test substance is administered for the first time to the animals. 24 hours after the final administration of substance (on the $8^{th}$ day after the beginning of treatment), a blood sample from each of the animals is again taken by puncture of the retroorbital venous plexus, to determine the same parameters. The blood samples are centrifuged and, after the serum has been obtained, TG, cholesterol, HDL-C and human ApoA1 are determined using a Cobas Integra 400 plus instrument (Cobas Integra, Roche Diagnostics GmbH, Mannheim, Germany) using the respective cassettes (TRIGL, CHOL2, HDL-C and APOAT). HDL-C is determined by gel filtration and post-column derivatization with MEGA cholesterol reagent (Merck KGaA) analogously to the method of Garber et al. [*J. Lipid Res.* 41, 1020-1026 (2000)].

The effect of the test substances on HDL-C, hApoA1 and TG concentrations is determined by subtracting the value measured for the first blood sample (zero value) from the value measured for the second blood sample (after the treatment). The means of the differences of all HDL-C, hApoA1 and TG values of a group are determined and compared with the mean of the differences of the control group. Statistical evaluation is carried out using Student's t-Test, after the variances have been checked for homogeneity.

Substances which increase the HDL-C of the treated animals, compared to that of the control group, in a statistically significant manner ($p<0.05$) by at least 20% or which lower TG in a statistically significant manner ($p<0.05$) by at least 25% are considered to be pharmacologically effective.

B-4: DOCA/Salt Model:

In rats, administration of deoxycorticosterone acetate (DOCA) in combination with a diet high in salt and unilateral removal of a kidney induces hypertension which is characterized by relatively low rennin levels. As a result of this endocrine hypertension (DOCA is a direct precursor of aldosterone), there is, depending on the chosen DOCA concentration, hypertrophy of the heart and further end-organ damage, for example of the kidney, characterized inter alia by proteinuria and glomerulosclerosis. In this rat model, it is thus possible to examine test substances for any antihypertrophic and end-organ-protective action.

The left kidneys of male Sprague Dawley (SD) rats of an age of about 8 weeks (body weight between 250 and 300 grams) are removed. To this end, the rats are anesthetized with 1.5-2% strength isoflurane in a mixture of 66% $N_2O$ and 33% $O_2$, and the kidney is removed via a lateral incision. Sham-operated animals, where no kidney is removed, serve as later control animals.

SD rats whose kidney has been removed receive 1% sodium chloride in their drinking water, and, once a week, a subcutaneous injection of deoxycorticosterone acetate (dissolved in sesame oil; from Sigma) injected between the shoulder blades (high dose: 100 mg/kg/week s.c.; normal dose: 30 mg/kg/week s.c.).

The substances to be examined for their protective action in vivo are administered via stomach tube or via the feed (from Ssniff) or drinking water. One day before the start of the test, the animals are randomized into groups of the same number of animals, generally n=10. During the entire experiment, the animals receive drinking water and feed ad libitum. The substances are administered once per day for 4 to 6 weeks via stomach tube, feed or drinking water. The placebo group consists of animals treated in an identical manner, but which only receive the solvent or feed or drinking water without test substance.

The activity of the test substances is determined by measuring hemodynamic parameters [blood pressure, pulse, inotropy (dp/dt), relaxation time (tau), maximum left ventricular pressure, left ventricular end-diastolic pressure (LVEDP)], determining the weight of heart, kidney and lung, measuring protein excretion and also by measuring the gene expression of biomarkers (for example ANP, atrial natriuretic peptide, and BNP, brain natriuretic peptide) by RT/TaqMan-PCR following RNA isolation from cardial tissue.

Statistical evaluation is carried out using Student's t-Test, after checking the variances for homogeneity.

B-5: Determination of the Metabolic Stability

To determine the metabolic stability of test compounds, the latter are incubated in vitro with liver microsomes or, preferably, with primary fresh hepatocytes of various animal species (for example from rat and dog) and also of human origin to obtain and to compare metabolite profiles of a hepatic phase I and phase II metabolism which is as complete as possible.

The test compounds are incubated at a concentration of 10-20 μM. To this end, stock solutions of the substances at a concentration of 1-2 mM in acetonitrile are prepared and then pipetted at a dilution of 1:100 into the incubation mixture. The liver microsomes are incubated at 37° C. in 50 mM potassium phosphate buffer (pH 7.4) with and without NADPH-generating system consisting of 1 mM $NADP^1$, 10 mM glucose 6-phosphate and 1 unit of glucose 6-phosphate dehydrogenase. Primary hepatocytes are also incubated at 37° C. in suspension in Williams E medium. After an incubation time of 0-4 hours, the incubation mixtures are quenched with acetonitrile (final concentration about 30%) and the protein is centrifuged off at about 15 000×g. The samples quenched in this manner are either analyzed directly or stored at −20° C. until analysis.

Analysis is carried out using high-performance liquid chromatography with ultraviolet and mass-spectrometric detection (HPLC-UV-MS/MS). To this end, the supernatants of the incubation samples are chromatographed using suitable C18 reversed-phase columns and variable mobile phase mixtures of acetonitrile and 10 mM aqueous ammonium formate solution. The UV chromatograms in combination with mass-spectrometric MS/MS data serve to identify the metabolites and to elucidate their structures.

C. Working Examples of Pharmaceutical Compositions

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed using a conventional tablet press (see above for the dimensions of the tablet). A compressive force of 15 kN is used as a guideline for the compression.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:

Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. Stirring is continued until the compound according to the invention has dissolved completely.

i.v. Solution:

The compound according to the invention is, at a concentration below saturation solubility, dissolved in a physiologically acceptable solvent (for example isotonic saline, glucose solution 5% and/or PEG 400 solution 30%). The solution is subjected to sterile filtration and tilled into sterile and pyrogen-free injection containers.

The invention claimed is:

1. A compound of the formula (I)

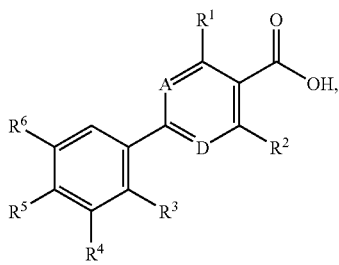

(I)

in which
A represents N and D represents CH,
$R^1$ isobutyl,
$R^2$ represents trifluoromethyl,
$R^3$ represents hydrogen,
$R^4$ represents hydrogen,
$R^5$ represents chlorine,
$R^6$ represents hydrogen,
and its salts.

2. A process for preparing compounds of the formula (I) as defined in claim 1, characterized in that a compound of the formula (II)

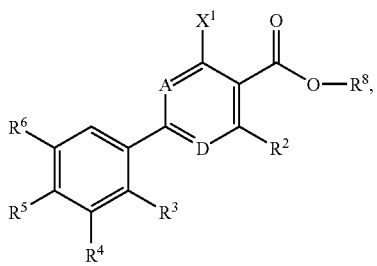

(II)

in which A,D, $R^2$, $R^3$, $R^4$, $R^5$ and $R^6$ have the meanings given in claim 1,
$X^1$ represents a suitable leaving group, such as, for example, halogen, in particular chlorine
and
$R^8$ represents $(C_1\text{-}C_4)$-alkyl,
is either
[A] reacted in an inert solvent in the presence of a base and a suitable palladium catalyst with a compound of the formula (III-A)

$R^{1A}$—$X^2$ (III-A), in which
$R^{1A}$ represents isobutyl,
and
$X^2$ represents a group of the formula —$B(OR^9)_2$ or -Zn-Hal, where
Hal represents halogen, in particular chlorine, bromine or iodine,
and
$R^9$ represents hydrogen or $(C_1\text{-}C_4)$-alkyl
or
both radicals $R^9$ together form a —$C(CH_3)_2$—$C(CH_3)_2$ bridge,
to give compounds of the formula (IV-A)

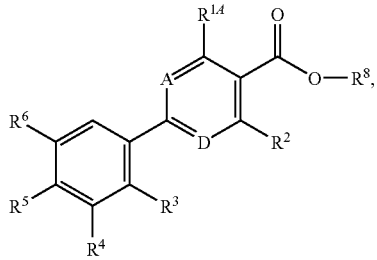

(IV-A)

in which A, D, $R^{1A}$, $R^2$, $R^3$, $R^4$, $R^5$, $R^6$ and $R^8$ each have the meanings given above,
and these are converted by basic or acidic hydrolysis into the carboxylic acids of the formula (I-A)

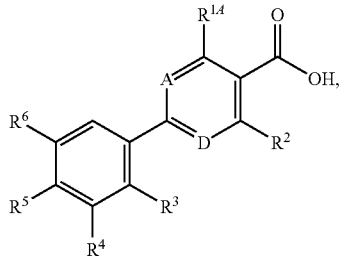

(I-A)

in which A,D, $R^{1A}$, $R^2$, $R^3$, $R^4$, $R^5$ and $R^6$ have the meanings given above,
or
[B] reacted in an inert solvent in the presence of a base with a compound of the formula (III-B)

$R^{1B}$—H (III-B), in which
claim 1,
to give compounds of the formula (IV-B)

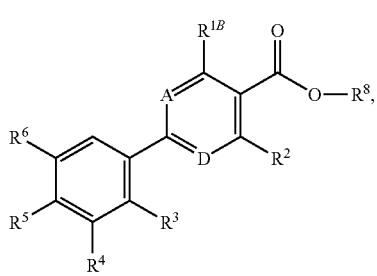

(IV-B)

in which A, D, $R^{1B}$, $R^2$, $R^3$, $R^4$, $R^5$, $R^6$ and $R^8$ each have the meanings given above, and these are converted by basic or acidic hydrolysis into the carboxylic acids of the formula (I-B)

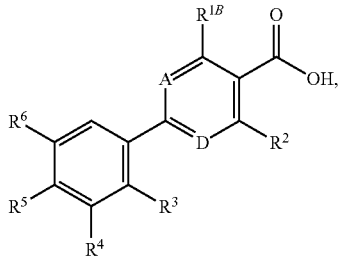
(I-B)

in which A, D, $R^{1B}$, $R^2$, $R^3$, $R^4$, $R^5$ and $R^6$ have the meanings given above.

3. A process for preparing compounds of the formula (I) as defined in claim 1 and in which A represents CH and D represents N, characterized in that a compound of the formula (XI)

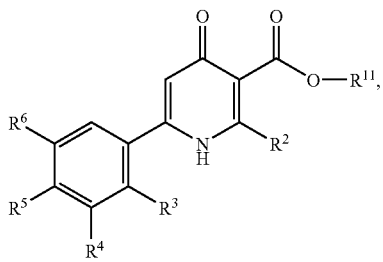
(XI)

in which $R^2$, $R^3$, $R^4$, $R^5$, and $R^6$ have the meaning given in claim 1
and
$R^{11}$ represents $(C_1$-$C_4)$-alkyl or benzyl,
is reacted in an inert solvent under Mitsunobu conditions with a compound of the formula (III-C)

$R^{1C}$—H (III-C), in which
where $R^c$ has the meaning given in claim 1

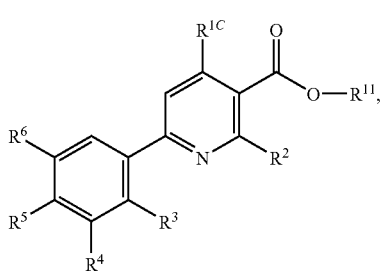
(IV-C)

in which $R^{1C}$, $R^2$, $R^3$, $R^4$, $R^5$, $R^6$ and $R^{11}$ each have the meanings given above, and these are converted by basic or acidic hydrolysis into the carboxylic acids of the formula (I-C)

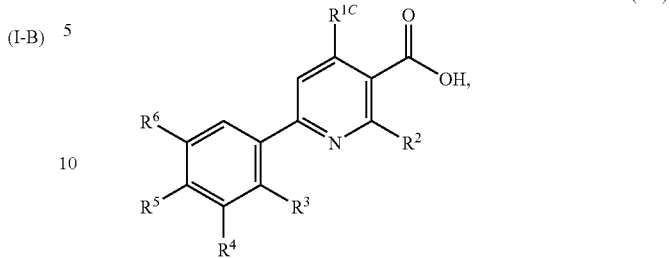
(I-C)

in which $R^{1C}$, $R^2$, $R^3$, $R^4$, $R^5$ and $R^6$ have the meanings given above.

4. A process for preparing the compounds of the formula (I) as defined in claim 1 and in which A represents $CR^7$ and D represents N, characterized in that a compound of the formula (XIV)

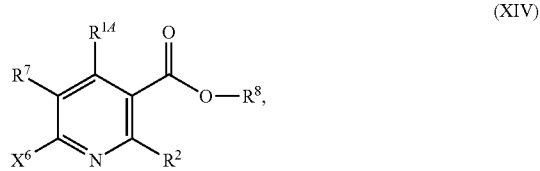
(XIV)

in which $R^2$ and $R^7$ have the meaning given in claim 1,
$R^{14}$ represents isobutyl
$R^8$ represents $(C_1$-$C_4)$-alkyl,
and
$X^6$ represents a suitable leaving group, such as, for example, halogen, in particular chlorine,
is, in an inert solvent in the presence of a suitable transition metal catalyst and, if appropriate, a base, coupled with a compound of the formula (VI)

(VI)

in which $R^3$, $R^4$, $R^5$ and $R^6$ have the meanings given above,
$X^4$ represents the group —$B(OR^9)_2$, -ZnHal or -MgHal,
where
Hal represents halogen, in particular chlorine, bromine or iodine,
and
$R^9$ represents hydrogen or $(C_1$-$C_4)$-alkyl
or
both radicals $R^9$ together form a —$C(CH_3)_2$—$C(CH_3)_2$ bridge,
to give compounds of the formula (IV-D)

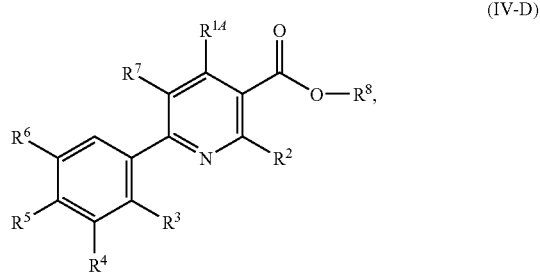
(IV-D)

in which $R^{14}$, $R^2$, $R^3$, $R^4$, $R^5$, $R^6$, $R^7$ and $R^8$ each have the meanings given above, and these are converted by basic or acidic hydrolysis into the carboxylic acids of the formula (I-D)

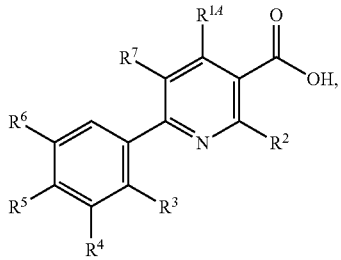

(I-D)

in which $R^{14}$, $R^2$, $R^3$, $R^4$, $R^5$, $R^6$, and $R^7$ have the meanings given above.

5. A medicament, comprising a compound of the formula (I) as defined in claim 1 in combination with an inert nontoxic pharmaceutically suitable auxiliary.

6. A medicament, comprising a compound of the formula (I) as defined in claim 1 in combination with one or more further active compounds selected from the group consisting of HMG-CoA reductase inhibitors, diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants.

7. The compound of claim 1, wherein the salt is a sodium salt.

* * * * *